US008951527B2

(12) United States Patent
Isenberg et al.

(10) Patent No.: US 8,951,527 B2
(45) Date of Patent: Feb. 10, 2015

(54) RADIOPROTECTANTS TARGETING THROMBOSPONDIN-1 AND CD47

(75) Inventors: Jeffrey S. Isenberg, Mt. Lebanon, PA (US); David D. Roberts, Bethesda, MD (US); Justin Maxhimer, Elkridge, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 684 days.

(21) Appl. No.: 13/057,447

(22) PCT Filed: Aug. 5, 2009

(86) PCT No.: PCT/US2009/052902

§ 371 (c)(1), (2), (4) Date: Feb. 3, 2011

(87) PCT Pub. No.: WO2010/017332

PCT Pub. Date: Feb. 11, 2010

(65) Prior Publication Data

US 2011/0135641 A1 Jun. 9, 2011

Related U.S. Application Data

(60) Provisional application No. 61/086,991, filed on Aug. 7, 2008.

(51) Int. Cl.

| | |
|---|---|
| ***A61K 38/08*** | (2006.01) |
| ***A61K 38/10*** | (2006.01) |
| ***A61K 38/36*** | (2006.01) |
| ***C12N 15/11*** | (2006.01) |
| ***A61K 38/39*** | (2006.01) |
| ***C07K 14/705*** | (2006.01) |
| ***C07K 14/78*** | (2006.01) |
| ***C07K 16/18*** | (2006.01) |
| ***C12N 15/113*** | (2010.01) |
| ***C07K 16/28*** | (2006.01) |
| *A61K 39/00* | (2006.01) |
| *A61N 5/10* | (2006.01) |

(52) U.S. Cl.

CPC ........... *A61K 38/39* (2013.01); *C07K 14/70596* (2013.01); *C07K 14/78* (2013.01); *C07K 16/18* (2013.01); *C12N 15/1138* (2013.01); *C07K 16/2803* (2013.01); *A61K 2039/505* (2013.01); *C07K 2316/96* (2013.01); *C12N 2310/11* (2013.01); *C12N 2310/3233* (2013.01); *A61N 2005/1094* (2013.01)

USPC ..... 424/172.1; 514/14.7; 514/21.5; 514/21.6; 514/44 A

(58) Field of Classification Search

None

See application file for complete search history.

(56) References Cited

U.S. PATENT DOCUMENTS

| | | | | |
|---|---|---|---|---|
| 5,357,041 | A | 10/1994 | Roberts et al. | |
| 5,399,667 | A | 3/1995 | Frazier et al. | |
| 5,491,130 | A | 2/1996 | Roberts et al. | |
| 5,627,265 | A | 5/1997 | Frazier et al. | |
| 5,770,563 | A | 6/1998 | Roberts et al. | |
| 5,814,667 | A | 9/1998 | Mitchell et al. | |
| 5,840,759 | A | 11/1998 | Mitchell et al. | |
| 5,849,701 | A | 12/1998 | Roberts et al. | |
| 6,051,549 | A | 4/2000 | Roberts et al. | |
| 6,384,189 | B1 | 5/2002 | Murphy-Ullrich et al. | |
| 6,458,767 | B1 | 10/2002 | Murphy-Ullrich et al. | |
| 6,469,138 | B1 | 10/2002 | Frazier et al. | |
| 7,129,052 | B1 | 10/2006 | Roberts et al. | |
| 7,282,556 | B2 | 10/2007 | Parkos et al. | |
| 8,394,757 | B2 * | 3/2013 | Gulati et al. | 514/1.1 |
| 2003/0026803 | A1 | 2/2003 | Barclay | |
| 2005/0281761 | A1 * | 12/2005 | Detmar et al. | 424/59 |
| 2008/0107654 | A1 | 5/2008 | Kikuchi et al. | |
| 2008/0131431 | A1 | 6/2008 | Smith et al. | |
| 2009/0191202 | A1 | 7/2009 | Jamieson et al. | |
| 2010/0092467 | A1 | 4/2010 | Isenberg et al. | |

FOREIGN PATENT DOCUMENTS

| | | |
|---|---|---|
| WO | WO 00/47622 | 7/2000 |
| WO | WO 01/05812 | 1/2001 |
| WO | WO 01/91781 | 12/2001 |
| WO | WO 01/97806 | 12/2001 |
| WO | WO 2004/062659 | 7/2004 |
| WO | WO 2007/133811 | 11/2007 |
| WO | WO 2008/060785 | 5/2008 |

OTHER PUBLICATIONS

K. Prasad, "Handbook of Radiobiology", 2nd Edition, 1995, pp. 153-192, and pp. 225-238.*

Bleuel et al (PNAS, 1999, vol. 96, pp. 2065-2070).*

Allen et al (Endocrinology, 2009, vol. 150, pp. 1321-1329).*

Abstract of Glantz et al (Neurology, 1994, vol. 44, pp. 2020-2027).*

Taraboletti et al (FASEB Journal, 2000, vol. 10).*

Borek, The Journal of Nutrition, 2004, vol. 134, pp. 3207S-3209S.*

Yano et al, Journal of Investigative Dermatology, 2002, vol. 118, pp. 800-805).*

Lawler et al., "Thrombospondin-1 is Required for Normal Murine Pulmonary Homeostasis and its Absence Causes Pneumonia," *J Clin Invest*, 101: 982-992, 1998.

(Continued)

*Primary Examiner* — Karen Canella

(74) *Attorney, Agent, or Firm* — Klarquist Sparkman, LLP

(57) ABSTRACT

Described herein is the discovery that cell and tissue survival can be dramatically increased following radiation exposure through inhibition of the interaction between TSP-1 and CD47. This effect is shown using antisense molecules, peptides, and antibodies, which can now be used as radioprotectant agents. These agents find application in minimizing, reducing and/or preventing tissue damage following intentional and accidental radiation exposure, as well as increasing the therapeutic efficacy of radiation therapies by protecting non-target tissue from incidental radiation damage and by increasing tumor ablation following radiation treatment.

21 Claims, 19 Drawing Sheets

(56) References Cited

OTHER PUBLICATIONS

Lawler, "The functions of thrombospondin-1 and -2," *Curr Opin Cell Biol*, 12(5): 634-640, 2000.
Leach et al., "Activation of constitutive nitric-oxide synthase activity is an early signaling event induced by ionizing radiation," *J Biol Chem*, 277(18): 15400-15406, 2002.
Li et al., "Interactions of thrombospondins with α4β1 integrin and CD47 differentially modulate T cell behavior," *J Cell Biol*, 157(3): 509-519, 2002.
Li et al., "Thrombospondin-1 inhibits TCR-mediated T lymphocyte early activation," *J Immunol*, 166(4): 2427-2436, 2001.
Liebmann et al., "In vivo radiation protection by nitric oxide modulation," *Cancer Res*, 54(13): 3365-3368, 1994.
Lindberg et al., "Decreased resistance to bacterial infection and granulocyte defects in IAP-deficient mice," *Science*, 274: 795-798, 1996.
Manna and Frazier, "CD47 Mediates Killing of Breast Tumor Cells via GiDependent Inhibition of Protein Kinase A," *Cancer Res*, 64: 1026-1036, 2004.
Manna and Frazier, "The mechanism of CD47-dependent killing of T cells: heterotrimeric Gi-dependent inhibition of protein kinase A," *J Immunol*, 170(7): 3544-3553, 2003.
Manna et al., "CD47 Augments Fas/CD95-mediated Apoptosis," *J Biol Chem*, 280(33): 29637-29644, 2005.
Rebres et al., "Membrane Raft Association of CD47 is Necessary for Actin Polymerization and Protein Kinase C Theta Translocation in its Synergistic Activation of T Cells" *J Biol Chem*, 276(10): 7672-7680, 2001.
Rebres et al., "Normal Ligand Binding and Signaling by CD47 (Integrinassociated Protein) Requires a Long Range Disulfide Bond between the Extracellular and Membrane-spanning Domains," *J Biol Chem*, 276(37): 34607-34616, 2001.
Ridnour et al., "Nitric oxide regulates angiogenesis through a functional switch involving thrombospondin-1," *Proc Natl Acad Sci USA*, 102: 13147-13152, 2005.
Rofstad et al., "Antiangiogenic treatment with thrombospondin-1 enhances primary tumor radiation response and prevents growth of dormant pulmonary micrometastases after curative radiation therapy in human melanoma xenografts," *Cancer Res*, 63: 4055-4061, 2003.
Rusk et al., "Cooperative activity of cytotoxic chemotherapy with antiangiogenic thrombospondin-I peptides, ABT-526 in pet dogs with relapsed lymphoma," *Clin Cancer Res*, 12(24): 7456-7464, 2006.
Sarifakioglu et al., "The influence of sildenafil on random skin flap survival in rats: an experimental study," *B J Plast Surg*, 57: 769-772, 2004.
Shafiee et al., "Inhibition of retinal angiogenesis by peptides derived from thrombospondin-1," *Invest Ophthalmol Vis Sci*, 41(8): 2378-2388, 2000.
Short et al., "Inhibition of endothelial cell migration by thrombospondin-1 type-1 repeats is mediated by β1 integrins," *J Cell Biol*, 168: 643-653, 2005.
Song et al., The protective action of taurine and L-arginine in radiation pulmonary fibrosis. *J Environ Pathol Toxicol Oncol*, 17: 151-157, 1998.
Speilberger et al., "Use of Recombinant Human Keratinocyte Growth Factor (Palifermin) Can Reduce Severe Oral Mucositis in Patients With Hematologic Malignancies Undergoing Autologous Peripheral Blood Progenitor Cell Transplantation After Radiation-Based Conditioning," *J Support Oncol*, 2 (Supp. 2): 73-74, 2004.
Streit et al., Thrombospondin-1 suppresses wound healing and granulation tissue formation in the skin of transgenic mice, *EMBO J*, 19(13): 3272-3282, 2000.
Sugihara et al., "Preferential impairment of nitric oxide-mediated endothelium-dependent relaxation in human cervical arteries after irradiation," *Circulation*, 100: 635-641, 1999.
Takai et al., "Chk2-deficient mice exhibit radioresistance and defective p53-mediated transcription," *EMBO J*, 21(19): 5195-5205, 2002.
Ticchioni et al., "Integrin-associated protein (CD47) is a comitogen c molecule on CD3-activated human T cells," *J Immunol*, 158(2): 677-684, 1997.
Tolsma et al., "Peptides derived from two separate domains of the matrix protein thrombospondin-1 have anti-angiogenic activity," *J Cell Biol*, 122: 497-511, 1993.
Tsoutsou et al., "Radiation pneumonitis and fibrosis: mechanism underlying its pathogenesis and implications for future research," *Int J Radial Oncol Biol Phys*, 66: 1281-1293, 2006.
van Beek et al., "Signal regulatory proteins in the immune system," *J Immunol*, 175: 7781-7787, 2005.
Vogel et al., "Modulation of endothelial cell proliferation, adhesion, and motility by recombinant heparin-binding domain and synthetic peptides from the type I repeats of thrombospondin," *J Cell Biochem*, 53: 74-84, 1993.
Waclavicek et al., "T cell stimulation via CD47: agonistic and antagonistic effects of CD47 monoclonal antibody 1/1A4," *J Immunol*, 159(11): 5345-5354, 1997.
Weinstat-Saslow et al., "Transfection of thrombospondin 1 complementary DNA into a human breast carcinoma cell line reduces primary tumor growth, metastatic potential, and angiogenesis," *Cancer Res*, 54(24): 6504-6511, 1994.
Wink et al., "Nitric oxide protects against cellular damage and cytotoxicity from reactive oxygen species," *Proc Natl Acad Sci USA*, 90(21): 9813-9817, 1993.
Yee et al., "Expression of the type-1 repeats of thrombospondin-1 inhibits tumor growth through activation of transforming growth factor-beta," *Am J Pathol*, 165(2): 541-552, 2004.
Zhang et al., "Role of the L-arginine/nitric oxide pathway in ischaemic/reoxygenation injury of the human myocardium," *Clin Sci*, 99: 497-504, 2000.
Zhong et al., "Cobalt-60 gamma radiation increased the nitric oxide generation in cultured rat vascular smooth muscle cells," *Life Sci*, 74(25): 3055-3063, 2004.
Barazi et al., "Regulation of Integrin Function by CD47 Ligands," *The Journal of Biological Chemistry*, 244(45): 42859-42866, 2002.
Isenberg et al., "Thrombospondin-1 and CD47 Cell and Tissue Survival of Radiation Injury," *The American Journal of Pathology*, 173(4): 1100-1112, 2008.
Armstrong and Bornstein, "Thrombospondins 1 and 2 function as inhibitors of angiogenesis," *Mat Biol*, 22(1): 63-71, 2003.
Barazi et al., "Regulation of Integrin Function by CD47 Ligands: Differential Effects on αvβ3 and α4β1 Integrin-Mediated Adhesion," *J Biol Chem*, 277(45): 42859-42866, 2002.
Belmadani et al., "A thrombospondin-1 antagonist of transforming growth factor-β activation blocks cardiomyopathy in rats with diabetes and elevated angiotensin II," *Am J Pathol*, 171: 777-789, 2007.
Bornstein et al., "The role of thrombospondins 1 and 2 in the regulation of cell-matrix interactions, collagen fibril formation, and the response to injury," *Int J Biochem. Cell Biol*, 36(6): 1115-1125, 2004.
Bornstein, "Thrombospondins as matricellular modulators of cell function," *J Clin Invest*, 107(8): 929-934, 2001.
Bras et al., "Drp1 mediates caspase-independent type III cell death in normal and leukemic cells," *Mol Cell Biol*, 27: 7073-7088, 2007.
Brizel, "Pharmacologic approaches to radiation protection," *J Clin Oncol*, 25: 4084-4089, 2007.
Brown and Frazier, "Integrin-associated protein (CD47) and its ligands," *Trends Cell Biol*, 11(3): 130-135, 2001.
Carlson et al., "Structures of thrombospondins," *Cell Mol Life Sci*, 65: 672-686, 2008.
Cook et al., "Nitric oxide and ionizing radiation synergistically promote apoptosis and growth inhibition of cancer by activating p53," *Cancer Res*, 64: 8015-8021, 2004.
Cotrim et al., "Differential radiation protection of salivary glands versus tumor by Tempol with accompanying tissue assessment of Tempol by magnetic resonance imaging," *Clin Cancer Res*, 13(16): 4928-4933, 2007.
Culp et al., "Interference of macrophage migration inhibitory factor expression in a mouse melanoma inhibits tumor establishment by up-regulating thrombospondin-1," *Mol Cancer Res*, 5: 1225-1231, 2007.
de Fraipont et al., "Thrombospondins and tumor angiogenesis," *Trends Mol Med*, 7(9): 401-407, 2001.

(56) References Cited

OTHER PUBLICATIONS

DiPietro et al., "Thrombospondin 1 Synthesis and Function in Wound Repair," *Am J Pathol*, 148(6): 1851-1860, 1996.
Epperly et al., "Increased longevity of hematopoiesis in continuous bone marrow cultures derived from NOS1 (nNOS, mtNOS) homozygous recombinant negative mice correlates with radioresistance of hematopoietic and marrow stromal cells," *Exp Hernatol*, 35: 137-145, 2007.
Epperly et al., "Increased radioresistance, g2/M checkpoint inhibition, and impaired migration of bone marrow stromal cell lines derived from Smad3$^{-/-}$ mice.," *Radiat Res*, 165: 671-677, 2006.
Favier et al., "Critical overexpression of thrombospondin-1 in chronic leg Ischaemia," *J Pathol*, 207(3): 358-366, 2005.
Flanders et al., "Mice lacking Smad3 are protected against cutaneous injury induced by ionizing radiation," *Am J Pathol*, 160: 1057-1068, 2002.
Frazier et al., "The Thrombospondin Receptor Integrin-associated Protein (CD47) Functionally Couples to Heterotrimeric Gi," *J Biol Chem*, 274: 8554-8560, 1999.
Freeman et al., "Nitric oxide inhibitable isoforms of adenylate cyclase mediate epithelial secretory dysfunction following exposure to ionising radiation," *Gut*, 53: 214-221, 2004.
Gao et al., "Integrin-associated Protein is a Receptor for the C-terminal Domain of Thrombospondin," *J Biol Chem*, 271: 21-24, 1996.
Gao et al., "Thrombospondin modulates $\alpha_v$ $\beta_3$ function through integrin-associated protein," *J Cell Biol*, 135(2): 533-544, 1996.
Guo et al., "Antiproliferative and antitumor activities of D-reverse peptides derived from the second type-1 repeat of thrombospondin-1," *J Peptide Res*, 50: 210-221, 1997.
Hatoum et al., "Radiation induces endothelial dysfunction in murine intestinal arterioles via enhanced production of reactive oxygen species," *Arterioscler Thromb Vasc Biol*, 26: 287-294, 2006.
Isenberg et al., "Blocking thrombospondin-1/CD47 signaling alleviates deleterious effects of aging on tissue responses to ischemia," *Arterioscler Thromb Vasc Biol*, 27(12): 2585-2588, 2007.
Isenberg et al., "CD47 is Necessary for Inhibition of Nitric Oxide-stimulated Vascular Cell Responses by Thrombospondin-1," *J Biol Chem*, 281(36): 26069-26080, 2006.
Isenberg et al., "CD47: A New Target in Cardiovascular Therapy," *Arterioscler Thromb Vasc Biol*, 28: 615-621, 2008.
Isenberg et al., "Endogenous thrombospondin-1 is not necessary for proliferation but is permissive for vascular smooth muscle cell responses to platelet-derived growth factor," *Matrix Biol*, 24: 110-123, 2005.
Isenberg et al., "Increasing survival of ischemic tissue by targeting CD47," *Circ Res*, 100(5): 712-720, 2007.
Isenberg et al., "Gene silencing of CD47 and antibody ligation of thrombospondin-1 enhance ischemic tissue survival in a porcine model: Implications for human disease," *Ann Surg*, 247(5):860-868, 2008.
Isenberg et al., "Thrombospondin 1 and vasoactive agents indirectly alter tumor blood flow," *Neoplasia*, 10(8): 886-896, 2008.
Isenberg et al., "Thrombospondin-1 antagonizes nitric oxide-stimulated vascular smooth muscle cell responses," *Cardiovasc Res*, 71(4): 785-793, 2006.
Isenberg et al., "Thrombospondin-1 inhibits endothelial cell responses to nitric oxide in a cGMP-dependent manner," *Proc Nall Acad Sci USA*, 102(37): 13141-13146, 2005.
Isenberg et al., "Thrombospondin-1 limits ischemic tissue survival by inhibiting nitric oxide-mediated vascular smooth muscle relaxation," *Blood*, 109(5): 1945-1952, 2007.
Jimenez et al., "Signals leading to apoptosis-dependent inhibition of neovascularization by thrombospondin-1," *Nat Med*, 6(1): 41-48, 2000.
Kanda et al., "Role of thrombospondin-1-derived peptide, 4N1K, in FGF-2-induced angiogenesis," *Exp Cell Res*, 252: 262-272, 1999.
Karagiannis et al., "Modulation of cellular radiation responses by histone deacetylase inhibitors," *Oncogene*, 25: 3885-3893, 2006.
Khiabani and Kerrigan, "The effects of the nitric oxide donor SIN-1 on ischemia-reperfused cutaneous and myocutaneous flaps," *Plast Reconstr Surg*, 110: 169-176, 2002.
King et al., "Delayed complications of radiotherapy treatments for nasopharyngeal carcinoma: imaging findings," *Clin Radiol*, 62(3): 195-203, 2007.
Komarova et al., "Dual effect of p53 on radiation sensitivity in vivo: p53 promotes hematopoietic injury, but protects from gastro-intestinal syndrome in mice," *Oncogene*, 23: 3265-3271, 2004.
Kopp et al., "Thrombospondins deployed by thrombopoietic cells determine angiogenic switch and extent of revascularization," *J Clin Invest*, 116(12): 3277-3291, 2006.
Kouvaris et al., "Amifostine: The First Selective-Target and Broad-Spectrum Radioprotector," *The Oncologist*, 12: 738-747, 2007.
Kuntscher et al., "Role of nitric oxide in the mechanism of preclamping and remote ischemic preconditioning of adipocutaneous flaps in a rat model," *J Reconstr Microsurg*, 19: 55-60, 2003.
Kuo et al., "Nitrosoglutathione improves blood perfusion and flap survival by suppression iNOS but protecting eNOS expression in the flap vessels after ischemia/reperfusion injury," *Surgery*, 135: 437-446, 2004.
Kuo et al., "Nitrosoglutathione modulation of platelet activation and nitric oxide synthase expression in promotion of flap survival after ischemia/reperfusion injury," *J Surg Res*, 119: 92-99, 2004.
Kuo et al., "Nitrosoglutathione promotes flap survival via suppression of reperfusion injury-induced superoxide and inducible nitric oxide synthase induction," *J Trauma*, 57: 1025-1031, 2004.
Lamy et al., "Interactions between CD47 and thrombospondin reduce inflammation," *J Immunol*, 178(9): 5930-5939, 2007.
Lawler et al., "Thrombospondin-1 gene expression affects survival and tumor spectrum of p53-deficient mice," *Am J Pathol*, 159(5): 1949-1956, 2001.

* cited by examiner

SCC VII Murine Tumor Growth Model IP vs. SQ injection

Figure 21A
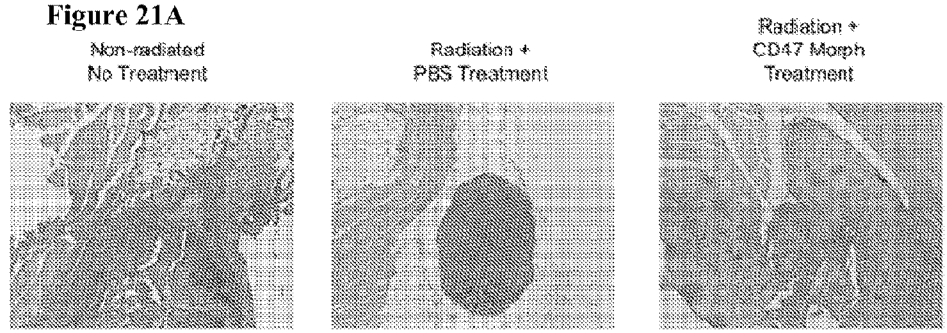
Figure 21B
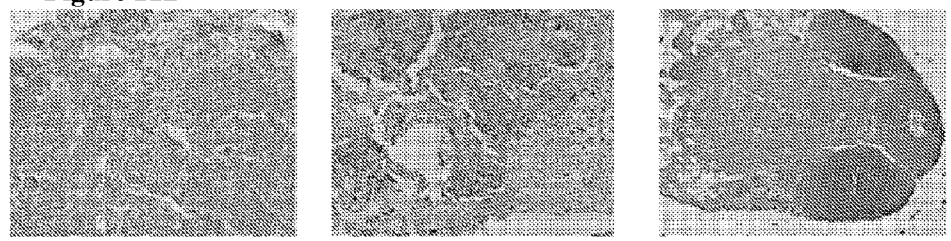
Figure 21C

RADIOPROTECTANTS TARGETING THROMBOSPONDIN-1 AND CD47

CROSS REFERENCE TO RELATED APPLICATIONS

This is the U.S. National Stage of International Application No. PCT/US2009/052902, filed Aug. 5, 2009, which was published in English under PCT Article 21(2), which in turn claims the benefit of U.S. Provisional Application 61/086,991, filed Aug. 7, 2008, which is incorporated herein by reference in its entirety.

FIELD

The present disclosure relates to compounds capable of reducing adverse effects of radiation exposure and/or increasing tumor ablation, as well as methods of using such compounds to reduce or ameliorate or block one or more of the adverse effects of radiation exposure or to increase tumor ablation.

BACKGROUND

Radiation has long been known to damage biological tissues and cells. Initial deposition of energy in irradiated cells occurs in the form of ionized and excited atoms or molecules distributed at random throughout the cells. The ionizations cause chemical changes in the exposed area, producing highly unstable charged or "ionized" molecules. These rapidly undergo chemical changes, producing free radicals that react with cellular components and lead to permanent damage.

As an immediate consequence of radiation damage, cells can undergo apoptosis, dying in interphase within a few hours of irradiation. Typical morphologic changes include loss of normal nuclear structure and degradation of DNA. DNA damage is important in triggering programmed cell death; membrane damage and signaling pathways are also thought to be involved.

A sufficiently high dose of radiation will inhibit mitosis. The inhibition of cellular proliferation is a primary mechanism by which radiation kills most cells. As radiation kills cells by inhibiting their ability to divide, its effects in living organisms occur primarily in tissues with high cell turnover or division rates, characterized by high proliferative activity. These include tissues such as the hone marrow and the mucosal lining of the stomach and small intestine. Another major target of radiation injury is the vascular system. Normal tissues experiences progressive and unremitting fibrosis, and occlusion of nutrient arteries and capillaries to soft tissues, following therapeutic radiation treatment for cancer. The secondary morbidity of this includes tissue necrosis and non-healing wounds.

The development of effective radioprotectant molecules is of great importance to populations potentially subjected to accidental, intentional or military exposure to radiation, including ionizing radiation.

In addition, the ability to prevent radiotherapy-induced toxicity without affecting antitumor therapeutic efficacy has the potential to enhance the therapeutic benefit for cancer patients without increasing their risk of serious adverse effects. Thus, another benefit to be realized from developing new cytoprotective therapies is to improve the therapeutic ratio by reducing the acute and chronic toxicities associated with more intensive and more effective anticancer therapies.

SUMMARY

It has been surprisingly discovered that cell and tissue survival can be dramatically increased following radiation exposure through inhibition of the interaction between TSP-1 and CD47, and/or the function of one or both of these proteins. This effect is demonstrated herein using antisense molecules, peptides, and antibodies, all of which can now be used as radioprotectant agents. These agents find application in minimizing, reducing and/or preventing tissue damage following intentional and accidental radiation exposure, as well as increasing the therapeutic efficacy of radiation therapies by protecting non-target tissue from incidental radiation damage. This effect is shown to be specific to non-target tissue. Moreover, it has been surprisingly discovered that inhibition of the TSP-1/CD47 interaction increases tumor ablation in a subject undergoing radiotherapy.

Provided herein are methods of protecting animal tissue from damage caused by radiation exposure, comprising contacting the tissue with a therapeutically effective amount of an agent that inhibits interaction between thrombospondin-1 (TSP1) and CD47, thereby protecting the tissue from radiation damage.

Also provided herein are methods of increasing tumor ablation in a subject undergoing radiotherapy, comprising contacting tissue of the subject with a therapeutically effective amount of an agent that inhibits interaction between TSP1 and CD47, prior to the radiotherapy, thereby increasing tumor ablation.

In various embodiments, the agent that inhibits interaction between TSP1 and CD47 comprises a synthetic peptide having specific binding affinity for CD47; an oligonucleotide or stable analog comprising at least about 15 contiguous bases and that hybridizes to the mRNA of CD47 under high stringency conditions; an isolated or recombinant CD47 or TSP1 molecule or soluble fragment thereof, or molecule that binds thereto; an agent that decreases the expression of CD47 or TSP1; a CD47 antagonist; an antibody that specifically binds TSP-1; an antibody that specifically binds CD47; or a mixture of two or more thereof.

Also described herein are uses of agents to reduce, prevent, or treat cell damage from radiation, where the agent is selected from the group consisting of isolated or recombinant CD47 or TSP1 molecules or soluble fragment thereof, molecules that disrupts the interaction between CD47 and TSP1, molecules that decrease the expression of CD47 or TSP1, CD47 antagonists, antibodies that specifically bind CD47, and antibodies that specifically bind to TSP1.

Methods of identifying radioprotectant agents are also described.

The foregoing and other features and advantages will become more apparent from the following detailed description of several embodiments, which proceeds with reference to the accompanying figures.

Figure 22A:
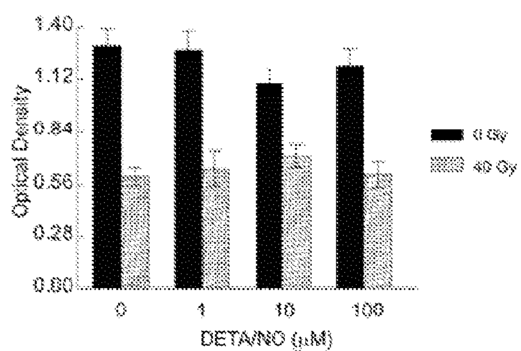
Figure 22B:
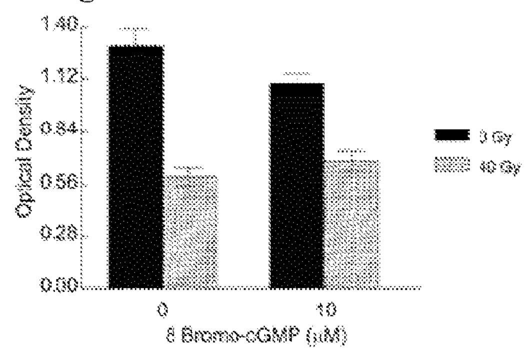
Figure 22C:
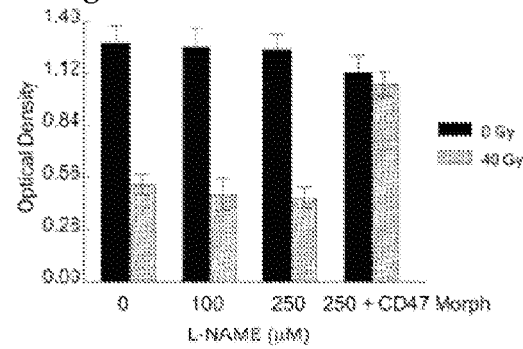

FIG. 22. The radioprotective effect of CD47 suppression is independent of cGMP/NO signaling. IIUVEC plated in 96 well plates were treated with the indicated doses of a slow releasing NO donor DETA/NO (FIG. 22A) or membrane permeable cGMP analog, 8-Bromo cGMP (FIG. 22B). Cells were subjected to either high dose (40 Gy) radiation or no radiation. Cell viability was measured by an MTT assay 48 hours post radiation. An NO inhibitor, L-NAME (FIG. 22C), was also incubated with HUVEC prior to radiation and cell viability was again measured by MTT assay. HUVEC viability was also examined after co-incubation of L-NAME and CD47 morpholino±radiation.

SEQUENCE LISTING

The disclosed nucleic and amino acid sequences referenced herein are shown using standard letter abbreviations for nucleotide bases, and three letter code for amino acids, as defined in 37 C.F.R. 1.822. In the accompanying sequence listing:

SEQ ID NO: 1 is peptide C6d.

SEQ ID NO: 2 is peptide p7N3.

SEQ ID NO: 3 is peptide p604,

SEQ ID NO: 4 is a CD47 targeting morpholino.

SEQ ID NO: 5 is a CD47 control morpholino.

SEQ ID NOs: 6 and 7 are oligonucleotides used to amplify PKD1 polycystin 1 NT_039649.6 (nuclear).

SEQ ID NO: 8 and 9 are oligonucleotides used to amplify GTF2IRD1 General transcription factor, NT_039314 (nuclear).

SEQ ID NOs: 10 and 11 are oligonucleotides used to amplify Osteocalcin NM_001032298.2 (nuclear).

SEQ ID NOs: 12 and 13 are oligonucleotides used to amplify NADH6 NC_005089.1 (mitochondrial).

SEQ ID NOs: 14 and 15 are oligonucleotides used to amplify 6S rRNA NC_005089.1 (mitochondrial).

SEQ ID NO: 16 is a CD36 targeting morpholino.

DETAILED DESCRIPTION

I. Abbreviations

3TSR type 1 repeats of TSP1
8-Br-cGMP 8-Bromo cyclic guanine monophosphate
ANOVA analysis of variance
BOLD MRI blood oxygen level dependent magnetic resonance imaging
cGMP cyclic guanine monophosphate
E3CaG1 C-terminal regions of TSP1
eNOS endothelial NO synthase
FTSG full thickness skin graft
Gy Gray
HASMC human aortic smooth muscle cells (equivalent to HAVSMC)
IIAVSMC human aortic vascular smooth muscle cells
HUVEC human umbilical vein endothelial cells
I/R ischemia-reperfusion
IR ionizing radiation
L-NAME N-nitro-L-arginine methyl ester
NO nitric oxide
NoC1 N-terminal domains of TSP1
NOS nitric oxide synthase
PAD peripheral artery disease
PBS phosphate buffered saline
PVD peripheral vascular disease
SD standard deviation
sGC soluble guanylyl cyclase
TSP1 thrombospondin-1
VSMC vascular smooth muscle cells

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Administration: Administration of an active compound or composition can be by any route known to one of skill in the art. Administration can be local or systemic. Examples of local administration include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, which release the active agents and compounds over extended time intervals for sustained treatment effects.

Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Altered expression: Expression of a biological molecule (for example, mRNA or protein) in a subject or biological sample from a subject that deviates from expression if the same biological molecule in a subject or biological sample from a subject having normal or unaltered characteristics for the biological condition associated with the molecule. Normal expression can be found in a control, a standard for a population, etc. Altered expression of a biological molecule may be associated with a disease. The term associated with includes an increased risk of developing the disease as well as the disease itself. Expression may be altered in such a manner as to be increased or decreased. The directed alteration in expression of mRNA or protein may be associated with therapeutic benefits.

Altered protein expression refers to expression of a protein that is in some manner different from expression of the protein in a normal (wild type) situation. This includes but is not necessarily limited to: (1) a mutation in the protein such that one or more of the amino acid residues is different; (2) a short deletion or addition of one or a few amino acid residues to the sequence of the protein; (3) a longer deletion or addition of amino acid residues, such that an entire protein domain or sub-domain is removed or added; (4) expression of an increased amount of the protein, compared to a control or standard amount; (5) expression of an decreased amount of the protein, compared to a control or standard amount; (6) alteration of the subcellular localization or targeting of the protein; (7) alteration of the temporally regulated expression of the protein (such that the protein is expressed when it normally would not be, or alternatively is not expressed when it normally would be); and (8) alteration of the localized (for example, organ or tissue specific) expression of the protein (such that the protein is not expressed where it would normally be expressed or is expressed where it normally would not be expressed), each compared to a control or standard.

Controls or standards appropriate for comparison to a sample, for the determination of altered expression, include samples believed to express normally as well as laboratory values, even though possibly arbitrarily set, keeping in mind that such values may vary from laboratory to laboratory. Laboratory standards and values may be set based on a known or determined population value and may be supplied in the format of a graph or table that permits easy comparison of measured, experimentally determined values.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in *Remington* (*The Science and Practice of Pharmacology, 19th Edition* (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound. It is acknowledged that these terms may overlap in some circumstances.

Animal: Living multi-cellular vertebrate organisms, a category that includes, for example, mammals and birds. The term mammal includes both human and non-human mammals. Similarly, the term subject includes both human and veterinary subjects, for example, humans, non-human primates, dogs, cats, horses, and cows.

Angiogenesis: Biological process leading to the generation of new blood vessels through sprouting or growth from preexisting blood vessels. The process involves the migration and proliferation of endothelial and vascular smooth muscle cells from preexisting vessels. Angiogenesis occurs during pre-natal development, post-natal development, and in the adult. In the adult, angiogenesis occurs during the normal cycle of the female reproductive system, wound healing, and during pathological processes such as cancer (for a review see Battegay, *J. Molec. Med.* 73(7): 333-346, 1995).

Antagonist: A molecule or compound that tends to nullify the action of another, or in some instances that blocks the ability of a given chemical to bind to its receptor or other interacting molecule, preventing a biological response. Antagonists are not limited to a specific type of compound, and may include in various embodiments peptides, antibodies and fragments thereof, and other organic or inorganic compounds (for example, peptidomimetics and small molecules).

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one light (about 25 kD) and one heavy chain (about 50-70 kD). The N-terminus of each chain defines a variable region of about 100 to 110 or more amino acids primarily responsible for antigen recognition. The terms variable light chain ($V_L$) and variable heavy chain ($V_H$) refer, respectively, to these light and heavy chains.

As used herein, the term antibody includes intact immunoglobulins as well as a number of well-characterized fragments produced by digestion with various peptidases, or genetically engineered artificial antibodies. Thus, for example, pepsin digests an antibody below the disulfide linkages in the hinge region to produce $F(ab)'_2$, a dimer of Fab which itself is a light chain joined to $V_H$—$C_H$ 1 by a disulfide bond. The $F(ab)'_2$ may be reduced under mild conditions to break the disulfide linkage in the hinge region thereby converting the $F(ab)'_2$ dimer into an Fab' monomer. The Fab' monomer is essentially a Fab with part of the hinge region (see, *Fundamental Immunology*, W. E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antibodies for use in the methods, compositions, and systems of this disclosure can be monoclonal or polyclonal. Merely by way of example, monoclonal antibodies can be prepared from murine hybridomas according to the classical method of Kohler and Milstein (*Nature* 256:495-497, 1975) or derivative methods thereof. Detailed procedures for monoclonal antibody production are described in Harlow and Lane (*Antibodies, A Laboratory Manual*, CSHL, New York, 1988).

The terms bind specifically and specific binding refer to the ability of a specific binding agent (such as, an antibody) to bind to a target molecular species in preference to binding to other molecular species with which the specific binding agent and target molecular species are admixed. A specific binding agent is said specifically to recognize a target molecular species when it can bind specifically to that target.

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science,* 242:423-426, 1988; Huston et al., *Proc. Natl. Acad. Sci.,* 85:5879-5883, 1988). Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.,* 90:6444-6448, 1993; Poljak et al., *Structure,* 2:1121-1123, 1994). One or more CDRs may be incorporated into a molecule either covalently or noncovalently to make the resultant molecule an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest. A chimeric antibody is an antibody that contains one or more regions from one antibody and one or more regions from one or more other antibodies.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

A neutralizing antibody or an inhibitory antibody is an antibody that inhibits at least one activity of a target—usually a polypeptide—such as by blocking the binding of the polypeptide to a ligand to which it normally binds, or by disrupting or otherwise interfering with a protein-protein interaction of the polypeptide with a second polypeptide. An activating antibody is an antibody that increases an activity of a polypeptide. Antibodies may function as mimics of a target protein activity, or as blockers of the target protein activity, with therapeutic effect derived therein.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Antisense, Sense, and Antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or plus strand DNA. Sense molecules are molecules that are specifically hybridizable or specifically complementary to the minus strand of DNA. Antigene molecules are either antisense or sense molecules complimentary to a dsDNA target. In one embodiment, an antisense molecule specifically hybridizes to a target mRNA and inhibits transcription of the target mRNA.

Aptamer: A single-stranded nucleic acid molecule (such as DNA or RNA) that assumes a specific, sequence-dependent shape and binds to a target protein with high affinity and specificity. Aptamers generally comprise fewer than 100 nucleotides, fewer than 75 nucleotides, or fewer than 50 nucleotides. Mirror-image aptamer(s) (also called Spiegelmers™) are high-affinity L-enantiomeric nucleic acids (for example, L-ribose or L-2'-deoxyribose units) that display high resistance to enzymatic degradation compared with D-oligonucleotides (such as aptamers). The target binding properties of mirror-image aptamers are designed by an in vitro-selection process starting from a random pool of oligonucleotides, as described for example, in Wlotzka et al., *Proc. Natl. Acad. Sci.* 99(13):8898-8902, 2002. Applying this method, high affinity mirror-image aptamers specific for a polypeptide can be generated.

Binding affinity: A term that refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules, but it is not critical to the methods herein that these constants be measured or determined Rather, affinities as used herein to describe interactions between molecules of the described methods are generally apparent affinities (unless otherwise specified) observed in empirical studies, which can be used to compare the relative strength with which one molecule (e.g., an antibody or other specific binding partner) will bind two other molecules (e.g., two versions or variants of a peptide). The concepts of binding affinity, association constant, and dissociation constant are well known.

Binding domain: The molecular structure associated with that portion of a receptor that binds ligand. More particularly, the binding domain may refer to a polypeptide, natural or synthetic, or nucleic acid encoding such a polypeptide, the amino acid sequence of which represents a specific region (binding domain) of a protein, which either alone or in combination with other domains, exhibits binding characteristics. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited.

Binding partner: Any molecule or composition capable of recognizing and binding to a specific structural aspect of another molecule or composition. Examples of such binding partners and corresponding molecule or composition include antigen/antibody, hapten/antibody, lectin/carbohydrate, apoprotein/cofactor and biotin/(strept) avidin.

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

DNA (deoxyribonucleic acid): A long chain polymer that comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Deletion: The removal of a sequence of DNA (which may be as short as a single nucleotide), the regions on either side being joined together.

Effective amount of a compound: A quantity of compound sufficient to achieve a desired effect in a subject being treated. An effective amount of a compound can be administered in a single dose, or in several doses, for example daily, during a course of treatment. However, the effective amount of the compound will be dependent on the compound applied, the subject being treated, the severity and type of the affliction, and the manner of administration of the compound.

Encode: A polynucleotide is said to encode a polypeptide if, in its native state or when manipulated by methods well known to those skilled in the art, it can be transcribed and/or translated to produce the mRNA for and/or the polypeptide or a fragment thereof.

Epitope: An antigenic determinant. These are particular chemical groups or peptide sequences on a molecule that are antigenic, for instance, that elicit a specific immune response. An antibody binds a particular antigenic epitope, based on a 3-D structure of the antibody and the matching or cognate epitope. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8 to 10 amino acids in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology, Vol.* 66, Glenn E. Morris, Ed (1996). In one embodiment, an epitope binds an MHC molecule, such an HLA molecule or a DR molecule. These molecules bind polypeptides having the correct anchor amino acids separated by about eight to about ten amino acids, such as nine amino acids.

Functionally equivalent sequence variant: Sequence alterations that yield the same results as described herein. Such sequence alterations can include, but are not limited to, deletions, base modifications, mutations, labeling, and insertions.

Fusion protein: A protein comprising two amino acid sequences that are not found joined together in nature.

Gene expression: The process by which the coded information of a nucleic acid transcriptional unit (including, for example, genomic DNA or cDNA) is converted into an operational, non-operational, or structural part of a cell, often including the synthesis of a protein. Gene expression can be influenced by external signals; for instance, exposure of a subject to an agent that inhibits gene expression. Expression of a gene also may be regulated anywhere in the pathway from DNA to RNA to protein. Regulation of gene expression occurs, for instance, through controls acting on transcription, translation. RNA transport and processing, degradation of intermediary molecules such as mRNA, or through activation, inactivation, compartmentalization or degradation of specific protein molecules after they have been made, or by combinations thereof. Gene expression may be measured at the RNA level or the protein level and by any method known in the art, including Northern blot, RT-PCR, Western blot, or in vitro, in situ, or in vivo protein activity assay(s).

The expression of a nucleic acid may be modulated compared to a control state, such as at a control time (for example, prior to administration of a substance or agent that affects regulation of the nucleic acid under observation) or in a control cell or subject, or as compared to another nucleic acid. Such modulation includes but is not necessarily limited to overexpression, underexpression, or suppression of expression. In addition, it is understood that modulation of nucleic acid expression may be associated with, and in fact may result in, a modulation in the expression of an encoded protein or even a protein that is not encoded by that nucleic acid.

Interfering with or inhibiting gene expression refers to the ability of an agent to measurably reduce the expression of a target gene. Expression of a target gene may be measured by any method known to those of skill in the art, including for example measuring mRNA or protein levels. It is understood that interfering with or inhibiting gene expression is relative, and does not require absolute suppression of the gene. Thus, in certain embodiments, interfering with or inhibiting gene expression of a target gene requires that, following application of an agent, the gene is expressed at least 5% less than prior to application, at least 10% less, at least 15% less, at least 20% less, at least 25% less, or even more reduced. Thus, in some particular embodiments, application of an agent reduces expression of the target gene by about 30%, about 40%, about 50%, about 60%, or more. In specific examples, where the agent is particularly effective, expression is reduced by 70%, 80%, 85%, 90%, 95%, or even more. Gene expression is substantially eliminated when expression of the gene is reduced by 90%, 95%, 98%, 99% or even 100%.

Heterologous: A type of sequence that is not normally (for example, in the wild-type sequence) found adjacent to a second sequence. In one embodiment, the sequence is from a different genetic source, such as a virus or other organism, than the second sequence.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. Complementary refers to the base pairing that occurs between to distinct nucleic acid sequences or two distinct regions of the same nucleic acid sequence.

Increasing tumor ablation: The increased killing of cancerous or tumor cells in a subject undergoing radiotherapy. In some examples, increasing tumor ablation is evidenced by an increased delay in tumor regrowth following exposure to radiation as part of radiotherapy in a subject. Increasing tumor ablation encompasses, but is not restricted to, an enhanced anti-tumor immune response resulting from the protection of immune cells from the deleterious affects of radiotherapy by exposure of the immune cells to an agent that inhibits the interaction between TSP1 and CD47.

Inhibiting protein activity: To decrease, limit, or block an action, function or expression of a protein. The phrase inhibit protein activity is not intended to be an absolute term. Instead, the phrase is intended to convey a wide-range of inhibitory effects that various agents may have on the normal (for example, uninhibited or control) protein activity Inhibition of protein activity may, but need not, result in an increase in the level or activity of an indicator of the protein's activity. By way of example, this can happen when the protein of interest is acting as an inhibitor or suppressor of a downstream indicator. Thus, protein activity may be inhibited when the level or activity of any direct or indirect indicator of the protein's activity is changed (for example, increased or decreased) by at least 10%, at least 20%, at least 30%, at least 50%, at least 80%, at least 100% or at least 250% or more as compared to control measurements of the same indicator.

Inhibition of protein activity may also be effected, for example, by inhibiting expression of the gene encoding the protein or by decreasing the half-life of the mRNA encoding the protein.

Inhibits (or inhibiting) interaction: An agent inhibits an interaction between two or more molecules when the presence of the agent prevents one or more of the molecules from contacting, and thus interacting with, the other. In one example, the agent may decrease the presence or availability of one (or more) of the molecules. Thus, a CD47 antisense morpholino that suppresses the expression of CD47 will decrease the amount of CD47 that is available to interact with TSP1, and therefor inhibit interaction between CD47 and TSP1. Likewise, an agent that enhances proteolysis of CD47 or TSP1, or enhance removal of CD47 from the cell surface, will inhibit interaction between CD47 and TSP1.

In another example, the agent may physically blockade n interaction between the two (or more) molecules. Thus, a CD47-reactive monoclonal antibody that prevents TSP1 from binding to CD47 is an agent that inhibits interaction between CD47 and TSP1.

Injectable composition: A pharmaceutically acceptable fluid composition comprising at least one active ingredient, for example, a protein, peptide, or antibody. The active ingredient is usually dissolved or suspended in a physiologically acceptable carrier, and the composition can additionally comprise minor amounts of one or more non-toxic auxiliary substances, such as emulsifying agents, preservatives, pH buffering agents and the like. Such injectable compositions that are useful for use with the compositions of this disclosure are conventional; appropriate formulations are well known in the art.

Isolated: An isolated biological component (such as a nucleic acid, peptide or protein) has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been isolated thus include nucleic acids and proteins purified by standard purification methods. The term also embraces nucleic acids, peptides and proteins prepared by recombinant expression in a host cell as well as chemically synthesized nucleic acids. The terms isolated and purified do not require absolute purity; rather, it is intended as a relative term. Thus, for example, an isolated peptide preparation is one in which the peptide or protein is more enriched than the peptide or protein is in its natural environment within a cell. Preferably, a preparation is purified such that the protein or peptide represents at least 50% of the total peptide or protein content of the preparation.

Label: A detectable compound or composition that is conjugated directly or indirectly to another molecule to facilitate detection of that molecule. Specific, non-limiting examples of labels include fluorescent tags, enzymatic linkages, and radioactive isotopes.

Mammal: This term includes both human and non-human mammals. Similarly, the term subject includes both human and veterinary subjects, for example, humans, non-human primates, mice, rats, dogs, cats, horses, and cows.

Modulator: An agent that increases or decreases (modulates) the activity of a protein or other bio-active compound, as measured by the change in an experimental biological parameter. A modulator can be essentially any compound or mixture (for example, two or more proteins), such as a NO donor, a polypeptide, a hormone, a nucleic acid, a sugar, a lipid and the like.

Morpholino: A morpholino oligo is structurally different from natural nucleic acids, with morpholino rings replacing the ribose or deoxyribose sugar moieties and non-ionic phosphorodiamidate linkages replacing the anionic phosphates of DNA and RNA. Each morpholino ring suitably positions one of the standard bases (A, G, C, T/U), so that a 25-base morpholino oligo strongly and specifically binds to its complementary 25-base target site in a strand of RNA via Watson-Crick pairing. Because the backbone of the morpholino oligo is not recognized by cellular enzymes of signaling proteins, it is stable to nucleases and does not trigger an innate immune response through the toll-like receptors. This avoids loss of oligo, inflammation or interferon induction. Morpholinos can be delivered by a number of techniques, including direct injection to tissues or via infusion pump and intravenous bolus, topical application, or intraperitoneal injection.

Mutation: Any change of DNA sequence, for instance within a gene or chromosome. In some instances, a mutation will alter a characteristic or trait (phenotype), but this is not always the case. Types of mutations include base substitution point mutations (for example, transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells, but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term overlaps with polymorphism, as defined below, but generally refers to the subset of constitutional alterations that have arisen within the past few generations in kindred and that are not widely disseminated in a population group. In particular embodiments, the term is directed to those constitutional alterations that have major impact on the health of affected individuals.

Nitric Oxide: A bioactive gas produced by a family of isoenzymes (e.g., NOS) and that drives many pro-survival signals in mammalian cells through activation of soluble guanylate cyclase (sGC). NO signaling is regulated at multiple points along the canonical pathway including at the level of sGC and downstream at the cGMP-dependant kinase by thrombospondin-1-CD47 Inhibitory signaling via TSP1-CD47 tempers both basal sGC activity in tissues and cells and blocks sGC activation by NO. Nitric oxide is an important prosurvival and proflow (that is, pro-blood-flow) molecule.

Nitric Oxide synthase: An enzyme that catalyzes conversion of 1-arginine, NADPH and oxygen to citrulline, nitric oxide and NADP+. Nitric oxide synthase catalyzes nitric oxide synthesis in the inner lining cells of blood vessels, as well as in macrophages and nerve cells. The generic nomenclature includes all three known isoforms of NOS designated in the literature as eNOS, iNOS and nNOS and alternatively as NOS-I, NOS-II and NOS-III.

Nucleic acid molecule: A polymeric form of nucleotides, which may include both sense and anti-sense strands of RNA, cDNA, genomic DNA, and synthetic forms and mixed polymers thereof. A nucleotide refers to a ribonucleotide, deoxynucleotide or a modified form of either type of nucleotide. A nucleic acid molecule as used herein is synonymous with nucleic acid and polynucleotide. A nucleic acid molecule is usually at least 10 bases in length, unless otherwise specified. The term includes single- and double-stranded forms. A polynucleotide may include either or both naturally occurring and modified nucleotides linked together by naturally occurring nucleotide linkages and/or non-naturally occurring chemical linkers.

Nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and modified linkages (for example, alpha anomeric nucleic acids, etc.). The term nucleic acid molecule also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Unless specified otherwise, the left hand end of a polynucleotide sequence written in the sense orientation is the 5' end and the right hand end of the sequence is the 3' end. In addition, the left hand direction of a polynucleotide sequence written in the sense orientation is referred to as the 5' direction, while the right hand direction of the polynucleotide sequence is referred to as the 3' direction. Further, unless otherwise indicated, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

An anti-sense nucleic acid is a nucleic acid (such as, an RNA or DNA oligonucleotide) that has a sequence complementary to a second nucleic acid molecule (for example, an mRNA molecule). An anti-sense nucleic acid will specifically bind with high affinity to the second nucleic acid sequence. If the second nucleic acid sequence is an mRNA molecule, for example, the specific binding of an anti-sense nucleic acid to the mRNA molecule can prevent or reduce translation of the mRNA into the encoded protein or decrease the half life of the mRNA, and thereby inhibit the expression of the encoded protein.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules and morpholinos.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide.

Ortholog: Two nucleic acid or amino acid sequences are orthologs of each other if they share a common ancestral sequence and diverged when a species carrying that ancestral sequence split into two species. Orthologous sequences are also homologous sequences.

Parenteral: Administered outside of the intestine, for example, not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Polypeptide: A polymer in which the monomers are amino acid residues that are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

The term polypeptide fragment refers to a portion of a polypeptide that exhibits at least one useful epitope. The phrase "functional fragment(s) of a polypeptide" refers to all fragments of a polypeptide that retain an activity, or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell. An epitope is a region of a polypeptide capable of binding an immunoglobulin generated in response to contact with an antigen. Thus, smaller peptides containing the biological activity of insulin, or conservative variants of the insulin, are thus included as being of use.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W).

In some circumstances, variations in the cDNA sequence that result in amino acid changes, whether conservative or not, are minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90%, or even 95% or 98% identical to the native amino acid sequence. Programs and algorithms for determining percentage identity can be found at the NCBI website.

Preventing or treating: Preventing refers to inhibiting the full development of something (such as a disease, condition, etc.), for example inhibiting the development of tissue damage after radiation therapy or other exposure to energetic radiation. Treatment refers to a therapeutic intervention that ameliorates a sign or symptom after it has begun to develop.

Purified: In a more pure form than is found in nature. The term purified does not require absolute purity; rather, it is intended as a relative term. Thus, for example, a purified protein preparation is one in which the protein referred to is more pure than the protein in its natural environment within a cell.

The term substantially purified as used herein refers to a molecule (for example, a nucleic acid, polypeptide, oligonucleotide, etc.) that is substantially free of other proteins, lipids, carbohydrates, or other materials with which it is naturally associated. In one embodiment, a substantially purified molecule is a polypeptide that is at least 50% free of other proteins, lipids, carbohydrates, or other materials with which it is naturally associated. In another embodiment, the polypeptide is at least at least 80% free of other proteins, lipids, carbohydrates, or other materials with which it is naturally associated. In yet other embodiments, the polypeptide is at least 90% or at least 95% free of other proteins, lipids, carbohydrates, or other materials with which it is naturally associated.

Radioprotectant/Radioprotection: A cytoprotective substance or composition that prevents or lessens effect(s) of radiation, particularly on cells, biological tissues, organs, or organisms. The concept of the therapeutic ratio (TR) is central to understanding the rationale for using radioprotectants/radioprotectors (Brizel. *J. Clin. Oncol* 25:4084-4089, 2007). The TR relates tumor control probabilities and normal tissue complication probabilities to one another. An optimal radioprotector reduces the latter without significantly compromising the former, and is itself only minimally toxic. Radioprotective agents can be classified as protectants or mitigants: Protectors are administered before exposure to radiation (e.g., radiotherapy (RT) or accidental or unintentional exposure) and are designed to prevent radiation-induced injury. Amifostine is the prototype protectant see, e.g. Kouvaris et al., 12:738-747, 2007. Mitigants are administered after exposure to radiation, but before the phenotypic expression of injury and are intended to ameliorate injury. Palifermin (Kepivance®, Keratinocyte growth factor. KGF; see, e.g., Speilberger et al., *J. Support Oncol.* 2:73-74, 2004) can be considered as the prototype mitigant. Treatment is a strategy that is predominantly palliative and supportive in nature.

Radioprotection allows cells and tissues to survive, and optimally heal and grow, in spite of injury from radiation. Radiation inherently damages tissues. The degree of secondary tissue death and necrosis determines the amount of morbidity and mortality. Radioprotectants attempt reduce, minimize or block the ability of radiation injury to drive cell death. Cell death and tissue damage can be measured by many art known methods. Methods used in vitro and in vivo include biochemical assessment of cell death using functional apoptosis and necrosis assays (e.g., DNA fragmentation, caspase activation, PARP cleavage, annexin V exposure, cytochrome C release, and so forth), morphological changes in cells and tissues, and nuclear fragmentation and loss. In vivo, tissue damage can be assessed by loss of perfusion, scarring, desquamation, alopecia, organ perforation and adhesions, etc.

Radiation: Radiation, as the term is used in physics, is energy in the form of waves or moving subatomic particles emitted by an atom or other body as it changes from a higher energy state to a lower energy state. Common sources of radiation include radon gas, cosmic rays from outer space, and medical x-rays. Radiation can be classified as ionizing or non-ionizing radiation, depending on its effect on atomic matter. The most common use of the word "radiation" refers to ionizing radiation. Ionizing radiation has sufficient energy to ionize atoms or molecules, while non-ionizing radiation does not. Radioactive material is a physical material that emits ionizing radiation. There are three common types of radiation, alpha, beta and gamma radiation. They are all emitted from the nucleus of an unstable atom. X-rays produced by diagnostic and metallurgical imaging and security screening equipment are also ionizing radiation, as are neutrons produced by nuclear power generation and nuclear weapons.

Sources of radiation exposure include, but are not limited to, radiotherapy, nuclear warfare, nuclear reactor accidents, and improper handling of research or medical radioactive materials.

Radiation Dosage: The rad is a unit of absorbed radiation dose defined in terms of the energy actually deposited in the tissue. One rad is an absorbed dose of 0.01 joules of energy per kilogram of tissue. The more recent SI unit is the gray (Gy), which is defined as 1 joule of deposited energy per kilogram of tissue. Thus, one gray is equal to 100 rad.

To accurately assess the risk of radiation, the absorbed dose energy in rad is multiplied by the relative biological effectiveness (RBE) of the radiation to get the biological dose equivalent in rems. Rem stands for "Röntgen Equivalent Man". In SI units, the absorbed dose energy in grays is multiplied by the same RBE to get a biological dose equivalent in sieverts (Sv). The sievert is equal to 100 rein.

The RBE is a "quality factor," often denoted by the letter Q, which assesses the damage to tissue caused by a particular type and energy of radiation. For alpha particles, Q may be as high as 20, so that one rad of alpha radiation is equivalent to 20 rem. The Q of neutron radiation depends on its energy. However, for beta particles, x-rays, and gamma rays, Q is taken as one, so that the rad and rem are equivalent for those radiation sources, as are the gray and sievert.

Radiation Poisoning: Also called radiation sickness or acute radiation syndrome, radiation poisoning involves damage to biological tissue due to excessive exposure to ionizing radiation. The term is generally used to refer to acute problems caused by a large dosage of radiation in a short period, though this also has occurred with long term exposure to low level radiation. Many of the symptoms of radiation poisoning result from ionizing radiation interference with cell division. Beneficially, this same interference enables treatment of cancer cells; such cells are among the fastest-dividing in the body, and in certain instances can be destroyed by a radiation dose that adjacent normal cells are likely to survive.

Symptoms of radiation poisoning include: reduction of red and/or white blood cell count, decreased immune function (with increased susceptibility to infection), nausea and vomiting, fatigue, sterility, hair loss, tissue burns and necrosis, gastrointestinal damage accompanied by internal bleeding, and so forth.

Radiation Therapy (Radiotherapy): The treatment of disease (e.g., cancer or another hyperproliferative disease or condition) by exposure of a subject or their tissue to a radioactive substance. Radiation therapy is the medical use of ionizing radiation as part of cancer treatment to control malignant cells. Radiotherapy may be used for curative or adjuvant cancer treatment. It is used as palliative treatment where cure is not possible and the aim is for local disease control or symptomatic relief.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

Ribozyme: RNA molecules with enzyme-like properties, which can be designed to cleave specific RNA sequences. Ribozymes are also known as RNA enzymes or catalytic RNAs.

RNA interference (RNA silencing; RNAi): A gene-silencing mechanism whereby specific double-stranded RNA (dsRNA) trigger the degradation of homologous mRNA (also called target RNA). Double-stranded RNA is processed into small interfering RNAs (siRNA), which serve as a guide for cleavage of the homologous mRNA in the RNA-induced silencing complex (RISC). The remnants of the target RNA may then also act as siRNA; thus resulting in a cascade effect.

Senescence: The biological process(es) of aging and showing the effects of increased age. In one embodiment, a senescent cell does not divide and/or has a reduced capacity to divide.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.* 2: 482, 1981); Needleman and Wunsch (*J. Mol. Biol.* 48: 443, 1970); Pearson and Lipman (*PNAS USA* 85: 2444, 1988); Higgins and Sharp (*Gene,* 73: 237-244, 1988); Higgins and Sharp (*CABIOS* 5: 151-153, 1989); Corpet et al. (*Nuc. Acids Res.* 16: 10881-10890, 1988); Huang et al. (*Comp. Appls Biosci.* 8: 155-165, 1992); and Pearson et al. (*Meth. Mol. Biol.* 24: 307-31, 1994). Altschul et al. (*Nature Genet.,* 6: 119-129, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program© 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., *J. Mol. Biol.* 215:403-410, 1990; Gish. & States, *Nature Genet.*

3:266-272, 1993; Madden et al. *Meth. Enzymol.* 266:131-141, 1996; Altschul et al., *Nucleic Acids Res.* 25:3389-3402, 1997; and Zhang & Madden, *Genome Res.* 7:649-656, 1997.

Orthologs of proteins are typically characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of particular domains of the disclosed peptides.

When significantly less than the entire sequence is being compared for sequence identity, homologous sequences will typically possess at least 80% sequence identity over short windows of 10-20 amino acids, and may possess sequence identities of at least 85%, at least 90%, at least 95%, or at least 99% depending on their similarity to the reference sequence. Sequence identity over such short windows can be determined using LFASTA; methods are described at the NCSA Website. One of skill in the art will appreciate that these sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (In *Molecular Cloning: A Laboratory Manual*, Cold Spring Harbor, N.Y., 1989) and Tijssen (*Laboratory Techniques in Biochemistry and Molecular Biology Part I, Ch.* 2, Elsevier, New York, 1993).

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na+ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11, herein incorporated by reference. The following is an exemplary set of hybridization conditions:

Very High Stringency (detects sequences that share 90% identity)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (detects sequences that share 80% identity or greater)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (detects sequences that share greater than 50% identity)

Hybridization: 6×SSC at RT to 55° C. for 16-20 hours

Wash at least twice: 2×-3×SSC at RT to 55° C. for 20-30 minutes each.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Specifically hybridizable and specifically complementary are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Small interfering RNAs: Synthetic or naturally-produced small double stranded RNAs (dsRNAs) that can induce gene-specific inhibition of expression in invertebrate and vertebrate species are provided. These RNAs are suitable for interference or inhibition of expression of a target gene and comprise double stranded RNAs of about 15 to about 40 nucleotides containing a 3' and/or 5' overhang on each strand having a length of 0 to about 5-nucleotides, wherein the sequence of the double stranded RNAs is essentially identical to a portion of a coding region of the target gene for which interference or inhibition of expression is desired. The double stranded RNAs can be formed from complementary ssRNAs or from a single stranded RNA that forms a hairpin or from expression from a DNA vector.

Small molecule inhibitor: A molecule, typically with a molecular weight less than 1000, or in some embodiments, less than about 500 Daltons, wherein the molecule is capable of inhibiting, to some measurable extent, an activity of some target molecule.

Subject: Living multi-cellular organisms, including vertebrate organisms, a category that includes both human and non-human mammals.

Target sequence: A target sequence is a portion of ssDNA, dsDNA, or RNA that, upon hybridization to a therapeutically effective oligonucleotide or oligonucleotide analog (e.g., a morpholino), results in the inhibition of expression of the target. Either an antisense or a sense molecule can be used to target a portion of dsDNA, as both will interfere with the expression of that portion of the dsDNA. The antisense molecule can bind to the plus strand, and the sense molecule can bind to the minus strand. Thus, target sequences can be ssDNA, dsDNA, and RNA.

Test compound: A compound used in a test or screen, and which can be essentially any compound, such as a small molecule, a chemotherapeutic, a polypeptide, a hormone, a nucleic acid, a modified nucleic acid, a sugar, a lipid and the like. Test compounds are used, for example, when screening for compounds that block the activity of TSP1 and/or CD47, or for compounds that affect TSP1 binding to CD47, and alternatively that mimic the activity of TSP1. Test compound may also function to suppress TSP1 and/or CD47 expression and/or production.

Therapeutic: A generic term that includes both diagnosis and treatment.

Therapeutically effective amount: A quantity of compound sufficient to achieve a desired effect in a subject being treated.

An effective amount of a compound may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can be measured as the concentration (moles per liter or molar-M) of the active ingredient (such as a small molecule, peptide, protein, or antibody) in blood (in vivo) or a buffer (in vitro) that produces an effect.

Therapeutically effective dosages of morpholino are generally in the range of 1-10 μM concentrations. By way of example, as used herein total delivered morpholino to 1×2 cm flaps or hind limbs was approximately 1 to 10 μg of morpholino oligonucleotide. Antibodies to TSP1 or CD47 were therapeutically efficacious at 40 μg per flap diluted to a concentration of approximately 0.4 μg/μl. Exact dosage amounts will vary by the size and other characteristics of the subject being treated, the duration of the treatment, the mode of administration, and so forth. For local treatment of tumors in mice, a typical dose was 150 μl of 10 μM CD47 morpholino, and for systemic IP delivery a typical volume of 450 μl of 10 μM was used. Doses for systemic administration of the morpholino in other species can readily be determined using standard pharmacokinetic and/or pharmacodynamic methods.

Under conditions sufficient for/to: A phrase that is used to describe any environment that permits the desired activity.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Thrombospondin and CD47

Thrombospondin 1 (TSP1) is an extracellular secreted protein that is involved in a myriad of cellular processes, including platelet aggregation, neurite outgrowth, cell motility, cell survival, and cellular proliferation. Among TSP1's best-characterized functions is inhibition of angiogenesis. Angiogenesis ameliorates the poor oxygenation of damaged tissue that is a limiting factor for patient recovery in a variety of clinical settings, including surgery, burn wound healing, organ transplantation and recovery, amputation, peripheral vascular disease and myocardial infarction. Because it is desirable to promote angiogenesis within these contexts, antagonizing TSP1's activity has been a valuable research objective. Additionally, tumors require vascularization for growth. Agents that mimic the ability of TSP1 to inhibit angiogenesis are therefore considered possible therapies for cancer. In vitro studies have shown the ability of such agents to block tumor driven angiogenesis. In vivo results in animals have also been encouraging and have led to clinical trials in people. See Rusk et al., *Clin Cancer Res* 12:7456-7464, 2006; Markovic et al., *Am J Clin Oncol* 30:303-309, 2007.

TSP1 contains three type 1 repeat structural domains and a carboxy-terminal domain that were identified as the loci of the full-length protein's anti-angiogenic functionality (Lawler, *Curr. Opin. Cell Biol.* 12(5): 634-640, 2000). Overexpression of TSP1 has been observed in ischemic tissue, and is proposed to regulate angiogenesis within ischemic tissue (Favier et al., *J. Pathol.* 207(3): 358-366, 2005), since TSP1 preferentially interferes with wound healing-associated angiogenesis (Streit et al., *EMBO J.* 19(13): 3272-3282, 2000) and limits revascularization in a model of hind limb ischemia similar to that employed by the current inventors (Kopp et al., *J. Clin. Invest.* 116(12): 3277-3291, 2006). Peptides derived from the type 1 repeats inhibit angiogenesis (Shafiee et al., *IOVS* 41(8): 2378-2388, 2000; Yee et al., *Am J. Pathol.* 165(2): 541-552, 2004; Tolsma et al., *J. Cell Biol.* 122: 497-511, 1993; Armstrong and Bornstein, *Mat. Biol.* 22(1): 63-71, 2003; Guo et al., *Cancer Res.* 58(14): 3154-3162, 1998; Guo et al., *J. Peptide Res* 50:210-221, 1997.). Additional TSP1 peptides (e.g., 4N1 and 7N3 classes) have previously been described; see, e.g., U.S. Pat. Nos. 5,399,667; 5,627,265; 6,469,138; 5,357,041; 5,491,130; 5,770,563; 5,849,701; 6,051,549; 6,384,189; 6,458,767; and 7,129,052.

TSP1 acts through several cellular receptors, including CD36 and integrin-associated protein (IAP)/CD47. It was originally thought that TSP1 exerted its anti-angiogenic effects by acting through CD36 (Quesada et al., *Cell Death and Diff.* 12: 649-658, 2005; Jiménez et al., *Nat. Med.* 6(1): 41-48, 2000; de Fraipon et al., *Trends Mol. Med.* 7(9): 401-407, 2001). Some evidence had indicated that CD36 was not solely responsible for the action of TSP1. For example, short peptides comprised of the TSP1 type 1 repeat can inhibit FGF- and VEGF-induced migration of human endothelial cells that lack CD36 binding (Vogel et al., *J. Cell. Biochem.* 53:74-84, 1993; Guo et al., *J. Peptide Res* 50:210-221, 1997; Short et al., *J. Cell Biol.* 168(4): 643-653, 2005). A sequence in the carboxy-terminal domain of TSP1 was hypothesized to mediate at least part of the protein's anti-angiogenic effects through an interaction with CD47 (Bornstein, *J Clin. Inv.* 107(8): 929-934, 2001) and was shown to have anti-angiogenic activity (Kanda et al., *Exp Cell Res.* 252(2):262-72, 1999). In contrast with the results from TSP1-derived peptides, the use of oligonucleotides to inhibit production of TSP1 suggested a contributory role of TSP1 in excisional dermal wound healing (DiPietro et al., *Am J. Pathol.* 148(6): 1851-1860, 1996).

CD47 is an atypical member of the immunoglobulin and the G protein-coupled receptor superfamilies. It consists of an N-terminal extracellular IgV set domain, 5 transmembrane segments and an alternatively spliced cytoplasmic tail (Brown and Frazier, *Trends Cell Biol.* 11(3): 130-135, 2001). Although identified earlier as "integrin associated protein (IAP), CD47 was discovered to be a receptor for the C-terminal domain of TSP1 in 1996 (Gao et al., *J. Biol. Chem.* 271: 21-24, 1996). Two members of the signal inhibitory receptor protein family, SIRPα (also known as BIT, SHPS-1 and p84)

and SIRPγ are cell-bound counter receptors for CD47 (van Beek et al., *J. Immunol.* 175:7781-87, 2005). CD47 is expressed on many if not all normal cells, and signals in part through coupling to G proteins of the Gi heterotrimeric class (Frazier et al., *J. Biol. Chem.* 274:8554-8560, 1999).

It was recently discovered that TSP1, via binding to CD47, potently limits physiologic NO signaling in all vascular cell types including endothelial cells, VSMC and platelets. TSP1-CD47 signaling also directly and acutely regulates tissue blood flow and arterial tone by inhibiting NO-driven vasorelaxation, and exerts anti-vasorelaxive effects on smooth muscle by antagonizing the ability of nitric oxide (NO) to stimulate cGMP synthesis (Isenberg et al., *Proc Natl Acad Sci USA.* 102(37): 13141-13146, 2005; Isenberg et al., *Cardiovasc Res.,* 71(4):785-793, 2006;); Isenberg et al., *J Biol Chem* 281:26069-26080, 2006, Isenberg et al., *Blood,* 109(5):1945-1952, 2007). Though inhibition of NO signaling may be induced by TSP1 interacting with CD36, this effect occurs at doses 100 to 1000 fold greater than the doses of TSP1 that drive inhibition through CD47. Also TSP1 inhibition of NO signaling through CD36 can not occur in the absence of CD47 at any dose, thus the physiologically relevant pathway is via CD47. (Isenberg et al., *J Biol. Chem.* 281(36):26069-26080, 2006). See also International Patent Publication No. WO 2008/060785, which is incorporated herein in its entirety.

The structure and function of CD47 has been explored using anti-CD47 antibodies and peptide ligands of the receptor. Certain anti-CD47 and TSP1-derived CD47 ligands initiate cell death in breast cancer cell lines (Manna and Frazier, *Cancer Res.* 64: 1026-1036, 2004) and Jurkat T cells (Manna and Frazier, *J. Immunol.* 170(7): 3544-3553, 2003). These, and similar experiments, led to the hypothesis that CD47 is necessary for FAS-mediated apoptosis of Jurkat T cells (Manna et al. *J. Biol. Chem.* 280(33): 29637-29644, 2005). Synthetic peptides derived from the full-length sequence of CD47 have been used to probe its structure (Rebres et al., *J. Biol. Chem.* 276(37): 34607-34616, 2001). Ligation of CD47 induces actin polymerization (Rebres et al., *J. Biol. Chem.* 276(10): 7672-7680, 2001); and its ligation by peptides derived from the carboxy-terminus of TSP1 stimulates the integrin-mediated adhesion of melanoma cells to specific substrates (Barazi et al., *J. Biol. Chem.* 277(45): 42859-42866, 2002; Gao et al., *J. Cell Biol.* 135(2): 533-544, 1996).

Different antibodies engaging CD47 can exert opposing stimulatory and inhibitory effects on cells (Li et al., *J Immunol* 166:2427-2436, 2001; Waclavicek et al., *J Immunol* 159: 5345-5354, 1997; Pettersen et al., *J Immunol* 162:7031-7040, 1999; Ticchioni et al., *J Immunol* 158:677-684, 1997). Likewise, a specific CD47 ligand can act as an agonist or an antagonist in different contexts. For instance, CD47 ligation by a particular ligand may have different effects in isolated cells than in vivo. Therefore, some effects of CD47 antibodies that have been defined using isolated cells do not extrapolate to in vivo activities, and the function of a specific CD47 ligand in vivo can not be predicted solely on the basis of in vitro testing.

IV. Overview of Several Embodiments

Provided herein is a method of protecting animal tissue from damage caused by radiation exposure, which method comprises contacting the tissue with a therapeutically effective amount of an agent that inhibits interaction between thrombospondin-1 (TSP1) and CD47, including an agent that does not necessarily blockade the physical interaction between TSP1 and CD47, thereby protecting the tissue from radiation damage. In certain embodiments, this method is employed as a method of protecting personnel exposed to a radioactive substance or ionizing radiation, and the method comprises contacting tissue of the personnel with the therapeutically effective amount of the agent.

It is contemplated in various examples that contacting in such is performed at least one of before, during or after exposure to radiation. For instance, in some cases the agent is administered within two weeks prior to exposure to radiation, during radiation exposure, and/or within two weeks following radiation exposure. In other cases, the agent is administered within 4 days prior to radiation exposure, during radiation exposure, and/or within about 1 day following radiation exposure.

In examples of the described methods, the radiation comprises an acute or chronic dose of ionizing or non-ionizing radiation. For instance, the ionizing radiation in some instances results from nuclear fission or fusion or from radioisotopes. In other instances, the ionizing radiation comprises X-rays. In other instances the ionizing radiation comprises radionuclides.

Also provided are methods of protecting animal tissue from damage caused by radiation exposure that are employed to enhance the therapeutic window for radiotherapy in a subject, such methods comprising contacting tissue of the subject with the therapeutically effective amount of the agent that inhibits interaction between TSP1 and CD47 prior to the radiotherapy.

It is also contemplated that the methods described herein are useful where the radiation exposure comprises diagnostic X-rays, radiation therapy, a CAT-scan, a mammogram, a radionuclide scan, or an interventional radiological procedure under CT or fluoroscopy guidance. In other embodiments, the radiation exposure comprises tissue-incorporated radionuclides from ingestion of contaminated food or water, non-medical or unintentional exposure to ionizing radiation from a nuclear weapon, non-medical or unintentional exposure to a radioactive spill, and/or cosmic radiation, including space flight-associated radiation exposure.

Also provided herein are methods of increasing tumor ablation in a subject undergoing radiotherapy comprising contacting tissue of the subject with a therapeutically effective amount of an agent that inhibits the interaction of TSP1 and CD47 prior to the radiotherapy, thereby increasing tumor ablation.

In various embodiments, the agent is administered orally, subcutaneously, intramuscularly, intravenously, intraperitoneally, transdermally, intranasally, or rectally.

In various embodiments inhibiting interaction between TSP1 and CD47 comprises one or more of inhibiting the expression of CD47, inhibiting the expression of TSP1, removing endogenous TSP1 or CD47, or blockading the interaction between endogenous TSP1 and CD47.

The agent that inhibits the interaction of TSP1 and CD47 will comprise, in various embodiments, a synthetic peptide having specific binding affinity for CD47; an oligonucleotide comprising at least about 15 contiguous bases and that hybridizes to the mRNA of CD47 under high stringency conditions; an oligonucleotide comprising at least about 15 contiguous bases and that hybridizes to the mRNA of TSP1 under high stringency conditions; an isolated or recombinant TSP1 or CD47 molecule or soluble fragment thereof, or molecule that binds thereto; an agent that decreases the expression of CD47; an agent that decreases the expression of TSP1; an agent that enhances the proteolysis of CD47; and agent that enhances the proteolysis of TSP1; an agent that enhances removal of CD47 from the cell surface; a CD47 antagonist; an antibody that specifically binds TSP1; an antibody that specifically binds CD47; or a mixture of two or more thereof. For instance, the agent that inhibits the interaction of TSP1 and CD47 in some examples is selected from the group consisting of peptide 7N3 (SEQ ID NO: 2) and peptide C6d (SEQ ID NO: 1).

Optionally, an agent as used in the provided methods may be modified by addition of a detectable label, glycosylation, β-hydroxylation, alkylation, reduction, calcium depletion, calcium supplementation, conjugation, and addition of a group or moiety to improve stability and/or bioavailability of the peptide (in embodiments where the agent is a peptide).

In specific examples, the agent is an oligonucleotide comprising at least about 15 contiguous bases and that hybridizes to the mRNA of CD47 under high stringency conditions. Such oligonucleotides will, in some embodiments, be a morpholino, for instance a morpholino that comprises the sequence shown in SEQ ID NO: 4.

In another specific example, the agent is an antibody (e.g., a humanized antibody) that specifically binds to CD47 or a fragment thereof, or an antibody that specifically binds to TSP1 or a fragment thereof. Specific examples of such agents that bind TSP1 include the monoclonal antibody A6.1, the monoclonal antibody C6.7, an antibody that competes with A6.1 or C6.7 for binding, a binding fragment of any one of these, or a humanized version of any one of these. Examples of such agents that bind to CD47 include antibodies MIAP301, OX101, and B6H12, an antibody that competes with MIAP301, OX101, and B6H12 for binding, a binding fragment of any one of these, or a humanized version of any one of these.

Also provided herein is use of an agent to reduce, prevent, or treat cell damage from radiation, where the agent is selected from the group consisting of isolated or recombinant CD47 or TSP1 molecules or soluble fragment thereof, molecules that disrupts the interaction between CD47 and TSP1, molecules that decrease the expression of CD47, molecules that decrease the expression of TSP1, CD47 antagonists, antibodies that specifically bind CD47, and antibodies that specifically bind to TSP1.

V. Radioprotectants Targeting Thrombospondin-1 and CD47

Described herein is the discovery that cell and tissue survival can be dramatically increased following radiation exposure through inhibition of the interaction between TSP-1 and CD47 and also through the suppression of CD47 itself. This effect is shown using antisense molecules, peptides, and antibodies, which can now be used as radioprotectant agents. These agents find application in minimizing, reducing and/or preventing tissue damage following intentional and accidental radiation exposure, as well as increasing the therapeutic efficacy of radiation therapies by protecting non-target tissue from incidental radiation damage. These agents also find application in increasing tumor ablation in a patient undergoing radiotherapy.

Also provided are pharmaceutical compositions for the treatment of a subject suffering from, or believed to be suffering from, radiation injury, the pharmaceutical composition comprising: a pharmacologically effective amount of radioprotective agent, or a functional analogue thereof, or pharmaceutical composition as identified herein, together with a pharmaceutically acceptable diluent. The disclosure further provides method of treating or preventing radiation injury in a subject in need thereof or in potential need thereof, the method comprising: administering to the subject a pharmaceutical composition comprising: at least one radioprotectant agent that interferes with or blocks the interaction between TSP1 and CD47, and a pharmaceutically acceptable excipient, in particular wherein the radiation injury comprises irradiation injury.

VI. Therapeutic Uses

The increased use of radionuclides in diagnostic and therapeutic nuclear medicine, as well as the presence of man-made and naturally occurring radioactivity in the environment, emphasizes the need for radioprotective agents for protection of cells, tissues and organisms before, during, and after exposure to radiation. The radioprotective agents described herein enable survival of living organisms in otherwise lethal radiation exposure conditions, and provide reduction of cellular and tissue damage from exposure to non-lethal levels of radiation.

The potential utility of radioprotective agents in protecting against exposure to environmental radiation, as well as in cancer radiation therapy, has long been recognized. These newly identified radioprotective agents described herein, administered prior to, during, and/or after exposure to radiation, would eliminate or reduce the severity of deleterious cellular effects caused by exposure to environmental ionizing radiation such as resulting from a nuclear explosion, a spill of radioactive material, close proximity to radioactive material and the like. The agents also provide dramatic protection of normal tissue exposed to therapeutic radiation used for cancer therapy.

The present invention provides methods which protect cells and living organisms from deleterious cellular effects by preventing or eliminating these effects or by reducing their severity. According to the present invention, living organisms to be protected can be exposed with an agent that blocks or inhibits the interaction between TSP1 and CD47 prior to, after, or during exposure of the cell to radiation. The cells may be directly treated by the radioprotective agent, such as by applying a solution of a radioprotective agent of the disclosure to the cell or by administering a radioprotective agent as described to a mammal. The compounds of the present invention thus can provide a protective effect in the cell and living organisms which eliminates or reduces the severity of the detrimental cellular effects which would otherwise be caused by the exposure.

It will be recognized that any and all tissue, skin or hair follicles can be treated or protected topically in accordance with the present invention.

Radioprotectants to Prevent or Treat Radiation Damage

Radioprotective agents of the present disclosure can be used to minimize or prevent the damage from solar radiation exposure experienced by astronauts, pilots, other flight personnel and frequent fliers. The radioprotective agents can also be utilized in protecting from accidental radiation exposure from nuclear power facilities, other radiation generating facilities including those for food irradiation, or as a result of detonation of an atomic bomb of other device that releases radiation or radioisotopes. Also, they can be used to confer protection to those personnel involved with clean up of such radiation accidents or disposal facilities. The radioprotective agents of the present invention are also of use in reducing the toxic effects of inhaled or ingested radionuclides and in reducing toxicity from radiation produced by electronic devices of non-ionizing nature of radiation: such as cellular telephones, and microwaves.

Rapidly growing interventional radiologic procedures such as dilatation of stenosed vessels, recanalization or vascular angioanastomoses would also benefit from the use of radioprotectors.

Additionally, therapy and diagnostic tests utilizing radiation are withheld from pregnant women, women who may be pregnant, and women capable of becoming pregnant to avoid harming the fetus in utero. This can often preclude necessary treatment or diagnosis for these women. Accordingly, radioprotective agents that are non-toxic and highly effective can be administered to such women so as to confer protection on the women and any possible fetus above and beyond any conventional mechanical radiation shielding device. This can also provide a level of safety to those women nursing their infants.

Radioprotectants to Enhance Radiotherapy

In addition, the radioprotective agents described herein are believed to provide a selective protection of normal cells, and not of cancer cells, during cancer radiation therapy. For example, these agents, administered to a cancer patient prior to or during radiation therapy, will provide protection to normal, non-cancer cells while allowing the radiation treatment to destroy cancerous cells. Therefore, the radioprotective agents would provide a selective protective effect on the normal cells as compared to tumor cells and would eliminate or reduce the severity of deleterious or other detrimental side effects of radiation therapy on normal cells and tissues.

Radioprotective agents thus are useful in eliminating or reducing the severity of deleterious cellular effects in normal cells caused by cancer radiation therapy and diagnostic tests utilizing radiation.

For example, the treatment of malignant tumors through the use of radiation is often limited due to damage to non-tumor cells. Damage to the non-tumor cells can compromise the effectiveness of the radiation therapy. The dominant consideration in establishing radiation doses for cancer radiotherapy is the assessment of tolerance of the most radiosensitive normal tissue or organ in the treatment field. This assessment, together with the expected radiation dose required to eradicate a tumor determines the feasibility of the treatment strategy, and whether a cure or palliation is to be attempted. Often, the maximum tolerable doses are insufficient to eradicate the tumor. Thus, the use of a radioprotective agent such as those provided herein would greatly increase the tolerable dose, and therefore the prospects for eradication of tumors and treatment of the cancer.

More particularly, provided herein are methods of protecting non-cancer, or normal, cells of a mammal from deleterious cellular effects caused by exposure of the mammal to ionizing radiation. The radioprotective agents described herein provide protection of normal cells during intentional exposure to radiation, such as during radiation therapy or diagnostic procedures such as x-rays and CAT scans. The cancer cells, if protected at all are believed to be protected to a lesser extent than normal cells. Despite a moderate protection in vitro, the cancer cells are rendered more sensitive to radiation in vivo, resulting in greater tumor ablation by radiotherapy. Thus, the inventors provide methods whereby the deleterious cellular effects on non-cancer cells caused by exposure of the mammal to radiation are eliminated or reduced in severity or in extent A further aspect of the radioprotective effect on normal cells is the preserved viability of macrophages and other immune cells that infiltrate and attack cancerous cells. As described herein, the TSP1/CD47 inhibition as part of radiotherapy significantly increases tumor ablation in a subject undergoing radiotherapy. Thus, not only do the described radioprotective agents allow for greater dosages of radiation in radiotherapy, but they enhance the innate ability of host anti-tumor immunity to attack cancerous cells.

VII. Combination Therapies

The immediate damage caused by radiation is mediated by formation of highly reactive free radicals inside the cell such as hydroxyl, peroxide, and carbonate radicals. These rapidly react with sensitive macromolecules such as DNA to cause permanent cell damage and eventual cell death. Chemical radioprotectants limit this immediate damage by directly neutralizing reactive radicals. The radioprotectants embodied in the subject disclosure are not directed to this immediate chemical damage but permit the cell to repair the immediate damage without triggering a suicide response. Therefore, combinations of the present embodiments with chemical protectants, such as thiols, that act by directly scavenging free radicals would be useful. Such combination would be particularly useful in cases where advance warning of radiation exposure is possible, but may have less advantage post-exposure, where chemical radioprotectants are less effective.

VIII. Production of Antibodies

In some embodiments, the radioprotective agent is an antibody or antigenic fragment thereof. Representative examples are antibody A6.1 (available from Genetex, Imgenex and Santa Cruz Biotechnology), antibody B6H12 (cell line HB-9771. ATCC; available form Abcam, Cambridge Mass.), and antibodies MIAP301 and OX101 (available from Santa Cruz Biotechnology). Also contemplated are antibodies that block or inhibit the interaction of TSP1 and CD47, which in addition have radioprotective activity.

Optimally, antibodies raised against a target protein (such as TSP1 or CD47) would specifically detect that peptide/protein, and optimally would inhibit the interaction between TSP1 and CD47. In some embodiments, CD47 antibodies that do not inhibit TSP1 binding may be active if they inhibit a TSP1-induced signal through CD47. Antibodies that specifically detect a target protein would recognize and bind that protein (and peptides derived therefrom) and would not substantially recognize or bind to other proteins or peptides found in a biological sample. The determination that an antibody specifically detects its target protein is made by any one of a number of standard immunoassay methods; for instance, the Western blotting technique (Sambrook et al., In *Molecular Cloning: A Laboratory Manual*, CSHL, New York, 1989).

To determine by Western blotting that a given antibody preparation (such as one produced in a mouse or rabbit) specifically detects the target peptide, the peptide of interest is synthesized and transferred to a membrane (for example, nitrocellulose) by Western blotting, and the test antibody preparation is incubated with the membrane. After washing the membrane to remove non-specifically bound antibodies, the presence of specifically bound antibodies is detected by the use of an anti-mouse or anti-rabbit antibody conjugated to an enzyme such as alkaline phosphatase.

Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the target peptide will, by this technique, be shown to bind to the target peptide band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-target peptide binding.

In addition, ELISA protocols could be used to identify therapeutic antibodies that inhibit interaction between TSP1 and CD47.

The determination that an antibody inhibits the association between TSP1 and CD47, or the ability of TSP1 or CD47 to provide radioprotection or minimize complications from tissue exposure to radiation, may be made, for example, using any one of the assays described herein that measure interaction or activity of one (or both) of these proteins. In addition, assays (including those described herein) that measure the radioprotectant effect of the antibodies can be employed.

For instance, the determination that an antibody inhibits TSP1 binding to purified or recombinant CD47 can be made by comparing the binding activity alone with the binding activity in the presence of the antibody using a solid phase ligand binding assay. An antibody that inhibits the activity of TSP1 to signal through CD47 on cells will reduce the activity of a cGMP-dependent reporter in a suitable transfected cell assay by a certain amount, for example, by 20%, 30%, 40%, 50%, 60%, 70%, 80%, 90%, or even by 100%.

A. Monoclonal Antibody Production by Hybridoma Fusion

Monoclonal antibody to epitopes of a target peptide (e.g., from TSP1 or CD47) can be prepared from murine hybridomas according to the classical method of Kohler and Milstein (*Nature* 256:495-497, 1975) or derivative methods thereof. Briefly, a mouse is repetitively inoculated with a few micrograms of the selected protein over a period of a few weeks. The mouse is then sacrificed, and the antibody-producing cells of the spleen are isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.* 70:419, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.* 33:988-991, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In Handbook of *Experimental Immunology*, Wier, D. (ed.) chapter 19. Blackwell, 1973). Plateau concentration of antibody is usually in the range of about 0.1 to 0.2 mg/ml of serum (about 12 μM). Affinity of the antisera for the antigen is determined by preparing competitive binding curves, as described, for example, by Fisher (*Manual of Clinical Immunology, Ch.* 42, 1980).

C. Antibodies Raised against Synthetic Peptides

A third approach to raising antibodies against a target peptide is to use synthetic peptides synthesized on a commercially available peptide synthesizer based upon the amino acid sequence of the native protein (e.g., TSP1 or CD47).

By way of example only, polyclonal antibodies to a CD47 or TSP1 peptide can be generated through well-known techniques by injecting rabbits or other animals (e.g., mice, guinea pigs, goats, pigs, primates) with chemically synthesized peptide.

D. Antibodies Raised by Injection of a Peptide-Encoding Sequence

Antibodies may be raised against a target peptide by subcutaneous injection of a DNA vector that expresses that peptide into laboratory animals, such as mice. Delivery of the recombinant vector into the animals may be achieved using a hand-held form of the Biolistic system (Sanford et al., *Particulate Sci. Technol.* 5:27-37, 1987) as described by Tang et al. (*Nature* 356:152-154, 1992). Expression vectors suitable for this purpose may include those that express the desired peptide-encoding sequence under the transcriptional control of either the human β-actin promoter or the cytomegalovirus (CMV) promoter.

E. Humanized Antibodies

Also contemplated are humanized antibodies, for instance humanized equivalents of murine or other non-human monoclonal antibodies. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, such as at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

The use of antibody components derived from humanized monoclonal antibodies obviates potential problems associated with the immunogenicity of the constant regions of the donor antibody. Techniques for producing humanized monoclonal antibodies are described, for example, by Jones et al.,

*Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al. *J. Immunol.* 150:2844, 1993. The antibody may be of any isotype, but in several embodiments the antibody is an IgM or an IgG, including but not limited to, $IgG_1$, $IgG_2$, $IgG_3$ and $IgG_4$.

Humanized monoclonal antibodies can be produced by transferring donor complementarity determining regions (CDRs) from heavy and light variable chains of the donor mouse (or other animal) immunoglobulin. The production of chimeric antibodies, which include a framework region from one antibody and the CDRs from a different antibody, is well known in the art. For example, humanized antibodies can be routinely produced. The antibody or antibody fragment can be a humanized immunoglobulin having complementarity determining regions (CDRs) from a donor monoclonal antibody that binds a cell surface antigen of pancreatic cells (such as endocrine, exocrine or ductal cells) and immunoglobulin and heavy and light chain variable region frameworks from human acceptor immunoglobulin heavy and light chain frameworks. Generally, the humanized immunoglobulin specifically binds to the cell surface antigen (or cells expressing the antigen) with an affinity constant of at least $10^7$ $M^{-1}$, such as at least $10^8$ $M^{-1}$ at least $5\times10^8$ $M^{-1}$ or at least $10^9$ $M^{-1}$.

In one embodiment, the sequence of the humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 95%, or at least about 99% identical to the sequence of the donor murine immunoglobulin heavy chain variable region framework. Human framework regions, and mutations that can be made in a humanized antibody framework regions, are known in the art (see, for example, in U.S. Pat. No. 5,585,089, which is incorporated herein by reference). One of skill in the art can readily select a human framework region of use.

Also contemplated are fully human antibodies. Mice have been generated that express only human immunoglobulin genes, instead of mouse genes. These mice are immunized with the target antigen, such as TSP1 or CD47, and resultant antibodies that are raised are selected for the activity desired. In the current instance, it is contemplated that this technique can be used to generate antibodies (including monoclonal antibodies) useful for blocking TSP-CD47 interactions. These procedures are substantially similar to those used to select a mouse anti-human Ab, but result in a fully human antibody since the mouse only has human Ig genes.

IX. Peptides and Peptide Variants

A. Representative Methods of Production

The peptides disclosed herein can be chemically synthesized by standard methods, or can be produced recombinantly. The synthesis of the presently disclosed compounds can be accomplished using standard chemical reactions known to be useful for preparing a variety of analogous compounds. Indeed, exemplary techniques known to those of ordinary skill in the art of peptide synthesis are taught by Bodanszky & Bodanszky (*The Practice of Peptide Synthesis*; Springer Verlag, New York, 1994) and by Jones (*Amino Acid and Peptide Synthesis;* 2nd ed.; Oxford University Press, 2002), both of which are incorporated herein by reference. The Bodanszky and Jones references detail the parameters and techniques for activating and coupling amino acids and amino acid derivatives. Moreover, the references teach how to select, use and remove various useful protecting groups. An exemplary specific process for (poly)peptide production is described in Lu et al. (*Fed. Europ Biochem Societies Lett.* 429:31-35, 1998).

By way of example, suitably N-alpha-protected (and side-chain protected if reactive side-chains are present) amino acid analogs or peptides are activated and coupled to suitably carboxyl-protected amino acid or peptide derivatives, either in solution or on a solid support. Protection of the alpha-amino functions generally takes place by urethane functions such as the acid-labile tertiary-butyloxycarbonyl group ("Boc"), benzyloxycarbonyl ("Z") group and substituted analogs or the base-labile 9-fluoremyl-methyloxycarbonyl ("Fmoc") group. The 7 group can also be removed by catalytic hydrogenation. Other suitable protecting groups include the Nps, Bmv, Bpoc, Aloc, MSC, etc. A good overview of amino-protecting groups is given in *The Peptides: Analysis, Synthesis, Biology*, Vol. 3, Gross and Meienhofer, eds. (Academic Press, New York, 1981). Protection of carboxyl groups can Lake place by ester formation, for example, base-labile esters like methyl or ethyl, acid labile esters like tert, butyl or, substituted benzyl esters or hydrogenolytically. Protection of side-chain functions like those of lysine and glutamic or aspartic acid can take place using the aforementioned groups. Protection of thiol, and although not always required, of guanidino, alcohol and imidazole groups, can take place using a variety of reagents such as those described in *The Peptides, Analysis, Synthesis, Biology*, Vol. 3, Gross and Meienhofer, eds. (Academic Press, New York, 1981), or in van Nispen (*Pure and Applied Chemistry,* 59(3). 331-344, 1987). Activation of the carboxyl group of the suitably protected amino acids or peptides can take place by the azide, mixed anhydride, active ester, or carbodiimide method especially with the addition of catalytic- and racemization-suppressing compounds like 1-N-N-hydroxybenzotriazole, N-hydroxysuccinimide, 3-hydroxy-4-oxo-3,4-dihydro-1,2, 3,-benzotriazine, N-hydroxy-5 norbornene-2,3-dicar-boxyimide. Also the anhydrides of phosphorus-based acids can be used. See, e.g., *The Peptides, Analysis, Synthesis, Biology*, Vol. 3, Gross and Meienhofer, eds. (Academic Press, New York, 1981); and van Nispen (*Pure and Applied Chemistry,* 59(3), 331-344, 1987).

It is also possible to prepare the peptides by the solid phase method of Merrifield. Different solid supports and different strategies are known (e.g., Barany and Merrifield in *The Peptides: Analysis, Synthesis, Biology*, Vol. 2, Gross and Meienhofer, eds. (Acad. Press, New York, 1980); Kneib-Cordonier and Mullen, Int. *J. Peptide Protein Res.,* 30, 705-739, 1987; and Fields & Noble, *Int. J. Peptide Protein Res.,* 35, 161-214, 1990). The synthesis of compounds in which a peptide bond is replaced by an isostere can, in general, be performed using the previously described protecting groups and activation procedures.

Removal of the protecting groups and, in the case of solid phase peptide synthesis, the cleavage from the solid support, can take place in different ways, depending on the nature of those protecting groups and the type of linker to the solid support. Usually, deprotection takes place under acidic conditions and in the presence of scavengers, using well known methods.

Another possibility is the application of enzymes in synthesis of peptides; for reviews see, Jakubke in *The Peptides: Analysis, Synthesis, Biology*, Vol. 9, Udenfriend and Meienhofer, eds. (Acad. Press, New York, 1987).

Peptides according to the subject disclosure can also be made according to recombinant DNA methods, by expressing a recombinant polynucleotide sequence that codes for the oligopeptide(s) in question in a suitable host cell, usually a microbial cell. Generally, the process involves introducing into a cloning vehicle (e.g., a plasmid, phage DNA, or other DNA sequence able to replicate in a host cell) a DNA sequence coding for the particular oligopeptide or oligopeptides, introducing the cloning vehicle into a suitable eukaryotic or prokaryotic host cell, and culturing the host cell thus transformed. When a eukaryotic host cell is used, the compound may optionally include a glycoprotein portion.

Polynucleotides encoding the peptides disclosed herein are also provided. These polynucleotides include DNA, cDNA and RNA sequences that encode the peptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., Stryer, *Biochemistry.* 3rd Edition, W.H. 5 Freeman and Co., NY 1988).

A nucleic acid encoding a peptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the peptide (or a longer polypeptide, such as an expression fusion polypeptide, containing the peptide) can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology* (Stockton Press, NY, 1989). Polynucleotides also can be isolated by screening genomic or cDNA libraries with probes selected from the sequences of the desired polynucleotide under stringent hybridization conditions.

The polynucleotides encoding a peptide (e.g., a peptide from or derived from TSP1 or CD47) include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single-stranded and double-stranded forms of DNA.

In one embodiment, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

The peptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the peptides disclosed herein. Myriad viral vectors have been constructed and are known to those of skill in the art, including but not limited to polyoma, SV40 (Madzak et al., *J. Gen. Virol.* 73:153311536, 1992), adenovirus (Berkner, *Cur. Top. Microbiol. Immunol.,* 158:39-36, 1992; Berliner et al., *BioTechniques,* 6:616-629, 1988; Gorziglia et al., *J. Virol.* 66:4407-4412, 1992; Quantin et al., *Proc. Nad. Acad. Sci. USA* 89:2581-2584, 1992; Rosenfeld et al., *Cell,* 68:143-155, 1992; Wilkinson et al., *Nucl. Acids Res.* 20:2233-2239, 1992; Stratford-Perricaudet et al., *Hum. Gene Ther.,* 1:241-256), vaccinia virus (Mackett et al., *Biotechnology,* 24:495-499, 1992), adeno-associated virus (Muzyczka, *Curr. Top. Microbiol. Immunol.* 158:91-123, 1992; On et al., 1990, Gene, 89:279-282), herpes viruses including HSV and EBV (Margolskee, *Curr. Top. Microbiol. Immunol.,* 158:67-90, 1992; Johnson et al., *J. Virol.* 66:2952-2965, 1992; Fink et al., *Hum. Gene Titer.* 3:11-19, 1992; Breakfield et al., *Mol. Neurobiol.,* 1:337-371, 1987; Fresse et al., *Biochem. Pharmacol.* 40:2189-2199, 1990), Sindbis viruses (Herweijer et al., *Human Gene Therapy* 6:1161-1167, 1995; U.S. Pat. No. 5,091,309), alphaviruses (Schlesinger, *Trends Biotechnol.* 11:18-22, 1993; Frolov et al., *Proc. Natl. Acad. Sci. USA* 93:11371-11377, 1996) and retroviruses of avian (Brandyopadhyay et al., *Mol. Cell. Biol.* 4:749-754, 1984; Petropouplos et al., *J. Viral.* 66:3391-3397, 1992), murine (Miller, *Curr. Top. Microbiol. Immunol.,* 158:1-24, 1992; Miller et al., 1985, Mol. Cell. Biol., 5:431-437; Sorge et al., *Mol. Cell. Biol.* 4:1730-1737, 1984; Mann et al., *J. Viral.* 54:401-407, 1985), and human origin (Page et al. *J. Virol.* 64:5370-5276, 1990; Buchschalcher et al., *J. Virol.* 66:2731-2739, 1992). Baculovirus (Autographa californica multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

B. Peptide Sequence Variants

Radioprotectant characteristics of the peptides disclosed herein (for instance, the 7N3 peptide) lie not in their precise and entire amino acid sequence, but rather in the three-dimensional structure inherent in the amino acid sequences encoded by the DNA sequences. It is possible to recreate the binding characteristics of any of these peptides, for instance the binding characteristics of any one of the specific peptides described herein, by recreating the three-dimensional structure, without necessarily recreating the exact amino acid sequence. Production of variations is enabled particularly in view of the guidance provided for the tolerance of variations at various positions within the core peptide. Such modifications and variations can be achieved for instance by designing a nucleic acid sequence that encodes for the three-dimensional structure, but which differs, for instance by reason of the redundancy of the genetic code or the substitution of one or more specific amino acids. Similarly, the DNA sequence may also be varied, while still producing a functional peptide.

Variant therapeutic peptides include peptides that differ in amino acid sequence from the disclosed sequence, but that share structurally significant sequence homology with any of the provided peptides. Such variants may be produced by manipulating the nucleotide sequence of the encoding sequence, using standard procedures, including site-directed mutagenesis or PCR. The simplest modifications involve the substitution of one or more amino acids for amino acids having similar biochemical properties. These so-called conservative substitutions are likely to have minimal impact on the activity of the resultant peptide, especially when made outside of the binding site of the peptide. One of ordinary skill in the art will be able to predict or empirically determine (particularly in view of the provided teachings) amino acids that may be substituted for an original amino acid in a peptide.

More substantial changes in peptide structure may be obtained by selecting amino acid substitutions that are less conservative than those listed in the above table. Such changes include changing residues that differ more significantly in their effect on maintaining polypeptide backbone structure (for example, sheet or helical conformation) near the substitution, charge or hydrophobicity of the molecule at the target site, or bulk of a specific side chain. The following substitutions are generally expected to produce the greatest changes in protein properties: (a) a hydrophilic residue (for example, seryl or threonyl) is substituted for (or by) a hydrophobic residue (for example, leucyl, isoleucyl, phenylalanyl, valyl or alanyl); (b) a cysteine or proline is substituted for (or by) any other residue; (c) a residue having an electropositive side chain (for example, lysyl, arginyl, or histadyl) is substituted for (or by) an electronegative residue (for example, glutamyl or aspartyl); or (d) a residue having a bulky side chain (for example, phenylalanine) is substituted for (or by) one lacking a side chain (for example, glycine).

Variant peptide-encoding sequences may be produced by standard DNA mutagenesis techniques, for example, M13 primer mutagenesis. Details of these techniques are provided in Sambrook (In *Molecular Cloning: A Laboratory Manual*, Cold Spring Harbor, N.Y., 1989), Ch. 15. By the use of such techniques, variants may be created which differ in minor ways from the disclosed radioprotectant peptides. DNA molecules and nucleotide sequences which are derivatives of those specifically disclosed herein and that differ from those disclosed by the deletion, addition, or substitution of nucleotides while still encoding a radioprotectant peptide, are comprehended by this disclosure. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a peptide having an amino acid sequence substantially similar to the disclosed peptide sequences. For example, one nucleotide codon triplet GCT encodes alanine Because of the degeneracy of the genetic code, three other nucleotide codon triplets—(GCG, GCC and GCA)—also code for alanine. Thus, a nucleotide sequence containing GCT for alanine could be changed at the same position to any of the three alternative codons without affecting the amino acid composition or characteristics of the encoded peptide. Based upon the degeneracy of the genetic code, variant DNA molecules may be derived from the cDNA and gene sequences disclosed herein using standard DNA mutagenesis techniques as described above, or by synthesis of DNA sequences. Thus, this disclosure also encompasses nucleic acid sequences which encode the subject peptides, but which vary from the disclosed nucleic acid sequences by virtue of the degeneracy of the genetic code.

An analogue can also be provided by systematically improving at least one desired property of an amino acid sequence. This can, for instance, be done by an Ala-scan and/or replacement net mapping method. With such methods, myriad different variant peptides are produced based on an original amino acid sequence; each variant peptide contains a substitution of at least one amino acid residue compared to the starting peptide. The amino acid residue may either be replaced by alanine (Ala-scan) or by any other amino acid residue (replacement net mapping). This way, many positional variants of the original amino acid sequence are synthesized. Every positional variant is screened for a specific activity, such as the activity of reducing cell or tissue damage to radiation exposure as described herein, or increased stability in a biological setting. The generated data are used to design improved peptide derivatives of a certain amino acid sequence.

C. Peptide Modifications

The present disclosure includes biologically active molecules that mimic the action of the inhibitor/blockade peptides of the present disclosure. The peptides of the disclosure include synthetic embodiments of naturally-occurring peptides described herein, as well as analogues (non-peptide organic molecules), derivatives (chemically functionalized protein molecules obtained starting with the disclosed peptide sequences) and variants (homologs) of these peptides that specifically bind TSP1 or CD47, or that block the interaction there between. Each peptide of the disclosure is comprised of a sequence of amino acids, which may be either L- and/or D-amino acids, naturally occurring and otherwise.

Thus, a variant peptide can also be generated by substitution of an L-amino acid residue with a D-amino acid residue. This substitution, leading to a peptide that does not naturally occur in nature, can improve a property of an amino acid sequence. It is, for example, useful to provide a peptide sequence of known activity of all D-amino acids in retro inversion format, thereby allowing for retained activity and increased half-life values. By generating many positional variants of an original amino acid sequence and screening for a specific activity, improved peptide derivatives comprising D-amino acids can be designed with further improved characteristics. It has been shown in the art that peptides that are protected by D-amino acids at either one or both termini were found to be more stable than those consisting of L-amino acids only. Other types of modifications include those known in the art of peptide drug development to have beneficial effects for use of the peptide in a pharmaceutical composition. These effects may include improved efficacy, altered pharmacokinetics, increasing stability resulting in a longer shelf-life and less stringent cold chain handling requirements.

Thus, in one embodiment, an anti-radiation peptide comprises a sequence of amino acids joined together in a chain by peptide bonds between their amino and carboxylate groups, wherein at least one amino acid is a D-amino acid.

Also, peptides or analogues can be circularized, for example, by providing them with (terminal) cysteines; dimerized or multimerized, for example, by linkage to lysine or cysteine or other compounds with side-chains that allow linkage or multimerization; brought in tandem- or repeat-configuration; conjugated or otherwise linked to carriers known in the art, if only by a labile link that allows dissociation. Synthetic versions of the oligopeptides described herein, and functional analogues or breakdown products, are herein provided to be used in methods of the treatment and/or prevention of radiation injury or damage.

Peptides may be modified by a variety of chemical techniques to produce derivatives having essentially the same activity as the unmodified peptides, and optionally having other desirable properties. For example, carboxylic acid groups of the peptides, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the peptides, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains in the described inhibitor peptides, resulting in such peptido- and organomimetics of the peptides of this disclosure having measurable or enhanced angiogenic or anti-angiogenic activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, Computer-Assisted Modeling of Drugs, in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included within the scope of the disclosure are mimetics prepared using such techniques that produce radioprotective peptides.

D. Additional Peptides

Additional peptides useful for blocking the interaction of TSP1 with CD47 are described in International Patent Publication No. WO 2008/060785, which is incorporated herein in its entirety. The radioprotectant characteristics of these and other peptides can be characterized using assays that measure their ability to reduce or prevent tissue or cellular damage after radiation exposure. Representative example methods are provided herein, including for instance in the Examples. Other methods will be apparent to those of ordinary skill in the art.

X. Pharmaceutical Compositions

The therapeutic compounds described herein may be formulated in a variety of ways depending on the location and type of disease to be treated or prevented in the subject. Pharmaceutical compositions are thus provided for both local use at or near an affected area and for systemic use (in which the agent is administered in a manner that is widely disseminated via the cardiovascular system). This disclosure includes within its scope pharmaceutical compositions including at least one peptide (for example, peptide C6d HIGWKDFTAYRWRLS (SEQ ID NO: 1) or peptide p7N3 FIRVVMYEGKK (SEQ ID NO: 2)) or another inhibitor of TSP1 or CD47 action or interaction (e.g., Ab A6.1 or Ab B6H12, or a CD47-directed morpholino such as CGTCACAGGCAGGACCCACTGCCCA (SEQ ID NO: 4)), formulated for use in human or veterinary medicine. While the peptides and inhibitors typically will be used to treat human subjects, they may also be used to treat similar or identical diseases in other vertebrates, such other primates, dogs, cats, horses, and cows.

Pharmaceutical compositions that include at least one peptide or other inhibitor or therapeutic compound as described herein as an active ingredient, or that include both a therapeutic peptide or inhibitor/blockade agent and an additional agent as active ingredients, or that include both a radioprotective peptide or inhibitor and an additional therapeutic agent, may be formulated with an appropriate solid or liquid carrier, depending upon the particular mode of administration chosen. Additional active ingredients include, for example, nitric oxide donors, nitrovasodilators, activators of the enzyme soluble guanylylcyclase, or cGMP phosphodiesterase inhibitors. Pharmaceutical compositions may include additional cytoprotective or radioprotectve agents known to the art (for example as described in Tofilon, *Chem. Rev.* 109:2974-88, 2009).

A suitable administration format may best be determined by a medical practitioner for each subject individually. Various pharmaceutically acceptable carriers and their formulation are described in standard formulation treatises, for example, *Remington's Pharmaceutical Sciences* by E. W. Martin. See also Wang and Hanson, *J. Parenteral Sci. Technol.*, Technical Report No. 10, Supp. 42: 2S, 1988.

The dosage form of the pharmaceutical composition will be determined by the mode of administration chosen. For instance, in addition to injectable fluids, inhalational, topical, ophthalmic, peritoneal, and oral formulations can be employed. Inhalational preparations can include aerosols, particulates, and the like. In general, the goal for particle size for inhalation is about 1 μm or less in order that the pharmaceutical reach the alveolar region of the lung for absorption. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The compositions or pharmaceutical compositions can be administered by any route, including parenteral administration, for example, intravenous, intramuscular, intraperitoneal, intrasternal, or intra-articular injection or infusion, or by sublingual, oral, topical, intra-nasal, ophthalmic, or transmucosal administration, or by pulmonary inhalation. When the active compounds are provided as parenteral compositions, for example, for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or depot slow release preparation may be used so that therapeutically effective amounts of the preparation are delivered into the bloodstream over many hours or days following transdermal injection or delivery.

Active compounds (e.g., peptides, proteins, oligos, and so forth) are also suitably administered by sustained-release systems. Suitable examples of sustained-release formulations include suitable polymeric materials (such as, for example, semi-permeable polymer matrices in the form of shaped articles, for example, films, or microcapsules), suitable hydrophobic materials (for example as an emulsion in an acceptable oil) or ion exchange resins, and sparingly soluble derivatives (such as, for example, a sparingly soluble salt). Sustained-release compounds may be administered by intravascular, intravenous, intra-arterial, intramuscular, subcutaneous, intra-pericardial, or intra-coronary injection. Administration can also be oral, rectal, parenteral, intracisternal, intravaginal, intraperitoneal, topical (as by powders, ointments, gels, drops or transdermal patch), buccal, or as an oral or nasal spray.

Preparations for administration can be suitably formulated to give controlled release of the therapeutic agent(s) (e.g., peptides, antibodies, oligonucleotides or other compounds that block CD47 and/or TSP1 activity or interaction). For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features that allow a controlled release of the active substance. See, for example, U.S. Pat. No. 5,700,486.

In some embodiments, therapeutic agent(s) are delivered by way of a pump (see Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution may also be employed. The key factor in selecting an appropriate dose is the result obtained, as measured by increases or decreases in radioprotection, or by other criteria for measuring control or prevention of disease, as are deemed appropriate by the practitioner. Other controlled release systems are discussed in the review by Langer (*Science* 249:1527-1533, 1990).

In another aspect of the disclosure, therapeutic agent(s) are delivered by way of an implanted pump, described, for example, in U.S. Pat. No. 6,436,091; U.S. Pat. No. 5,939,380; and U.S. Pat. No. 5,993,414. Implantable drug infusion devices are used to provide subjects with a constant and long term dosage or infusion of a drug or any other therapeutic agent. Essentially, such device may be categorized as either active or passive.

Active drug or programmable infusion devices feature a pump or a metering system to deliver the drug into the patient's system. An example of such an active drug infusion device currently available is the Medtronic SynchroMed™ programmable pump. Such pumps typically include a drug reservoir, a peristaltic pump to pump the drug out from the reservoir, and a catheter port to transport the pumped out drug from the reservoir via the pump to a patient's anatomy. Such devices also typically include a battery to power the pump, as well as an electronic module to control the flow rate of the pump. The Medtronic SynchroMed™ pump further includes an antenna to permit the remote programming of the pump.

Passive drug infusion devices, in contrast, do not feature a pump, but rather rely upon a pressurized drug reservoir to deliver the drug. Thus, such devices tend to be both smaller as well as cheaper as compared to active devices. An example of such a device includes the Medtronic IsoMed™. This device delivers the drug into the patient through the force provided by a pressurized reservoir applied across a flow control unit.

The implanted pump can be completely implanted under the skin of a subject, thereby negating the need for a percutaneous catheter. These implanted pumps can provide the patient with therapeutic agent(s) at a constant or a programmed delivery rate. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump system. Osmotic pumps may be much smaller than other constant rate or programmable pumps, because their infusion rate can be very low. An example of such a pump is described listed in U.S. Pat. No. 5,728,396.

The therapeutic agents may also be delivered passively and in sustained fashion as part of and incorporated into implantable devices, such as vascular stents which can be placed directly into diseased blood vessels through several standard approaches, including direct surgical insertion or percutaneously with angiographic control.

For oral administration, the pharmaceutical compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

For administration by inhalation, the compounds for use according to the present disclosure are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

For topical administration, the compounds can be, for example, mixed with a liquid delivery agent for administration locally. The agents used therapeutically (such as peptides, antibodies and morpholinos) are readily soluble or suspendable in water and saline, and as such these would be useful for delivery since water or saline do not cause adverse biological tissue effects. This allows sufficiently high doses to be administered locally or systemically, without secondary toxicity from the delivery vehicle.

Pharmaceutical compositions that comprise at least one therapeutic agent as described herein as an active ingredient will normally be formulated with an appropriate solid or liquid carrier, depending upon the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

For example, for parenteral administration, therapeutic agent(s) can be formulated generally by mixing them at the desired degree of purity, in a unit dosage injectable form (solution, suspension, or emulsion), with a pharmaceutically acceptable carrier, for instance, one that is non-toxic to recipients at the dosages and concentrations employed and is compatible with other ingredients of the formulation. A pharmaceutically acceptable carrier is a non-toxic solid, semisolid or liquid filler, diluent, encapsulating material or formulation auxiliary of any type.

Generally, the formulations are prepared by contacting the therapeutic agent(s) each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Nonaqueous vehicles such as fixed oils and ethyl oleate are also useful herein, as well as liposomes.

The pharmaceutical compositions that comprise at least one therapeutic agent, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The therapeutically effective amount of therapeutic agent, such as a peptide, antibody, or oligonucleotide (e.g., morpholino or other antisense molecule) will be dependent on the peptide or inhibitor utilized, the subject being treated, the severity and type of the affliction, and the manner of administration. The exact dose is readily determined by one of skill in the art based on the potency of the specific compound, the age, weight, sex and physiological condition of the subject.

The peptides/proteins of the present disclosure (for example, CD47 or TSP1 peptides, or a peptide that inhibits or alters binding between TSP1 and CD47, including a peptide from an antibody or an artificial antibody with this functional characteristic, or a peptide or protein that inhibits the expression or activity of either of these proteins) also can be administered as naked DNA encoding the peptide. To simplify the manipulation and handling of the nucleic acid encoding the peptide, the nucleic acid is generally inserted into a cassette, where it is operably linked to a promoter. Preferably, the promoter is capable of driving expression of the protein in cells of the desired target tissue. The selection of appropriate promoters can readily be accomplished. Preferably, the promoter is a high expression promoter, for example the 763-base-pair cytomegalovirus (CMV) promoter, the Rous sarcoma virus (RSV) promoter (Davis et al., *Hum. Gene. Ther.* 4:151-159, 1993), or the MMT promoter.

Other elements that enhance expression also can be included, such as an enhancer or a system that results in high levels of expression, such as a tat gene or tar element. This cassette is inserted into a vector, for example, a plasmid vector such as pUC118, pBR322, or other known plasmid vector, that includes, for example, an *E. coli* origin of replication. See, Sambrook, et al., *Molecular Cloning: A Laboratory Manual*, Cold Spring Harbor Laboratory Press (1989). The plasmid vector may also include a selectable marker such as the β-lactamase gene for ampicillin resistance, provided that the marker polypeptide does not adversely affect the metabolism of the organism being treated. The cassette also can be bound to a nucleic acid binding moiety in a synthetic delivery system, such as the system disclosed in PCT publication WO 95/22618.

Optionally, the DNA may be used with a microdelivery vehicle such as cationic liposomes and adenoviral vectors. (For a review of the procedures for liposome preparation, targeting and delivery of contents, see Mannino and Gould-Fogerite, *BioTechniques,* 6:682, 1988); Feigner and Holm, *Bethesda Res. Lab. Focus,* 11(2):21, 1989); and Maurer, *Bethesda Res. Lab. Focus,* 11(2):25, 1989). Replication-defective recombinant adenoviral vectors can be produced in accordance with known techniques. (See Quantin, et al., *Proc. Natl. Acad. Sci. USA,* 89:2581-2584, 1992; Stratford-Perricadet, et al., *J. Clin. Invest.,* 90:626-630, 1992; and Rosenfeld, et al., *Cell,* 68:143-155, 1992).

The effective dose of the nucleic acid will be a function of the particular expressed protein, the target tissue, the subject, and his or her clinical condition. Effective amounts of DNA are between about 1 and 4000 μg, or about 1000 and 2000 μg, or between about 2000 and 4000 μg. In certain situations, it is desirable to use nucleic acids encoding two or more different proteins in order to optimize the therapeutic outcome. For example, DNA encoding a therapeutic peptide, such as a CD47 or TSP1 peptide (for example, peptide C6d HIGWKDFTAYRWRLS (SEQ ID NO: 1) or peptide p7N3 FIRVVMYEGKK (SEQ ID NO: 2)) can be used. Alternatively, DNA encoding a CD47 or TSP1 peptide can be combined with other genes or their encoded gene products to enhance the activity of targeted cells.

In order to facilitate injection, the nucleic acid is formulated with a pharmaceutically acceptable carrier. Examples of suitable carriers include, but are not limited to, saline, albumin, dextrose and sterile water. The nucleic acid is injected into the ischemic tissue using standard injection techniques by use of, for example, a hypodermic needle, for example a hypodermic needle size between No. 29 and No. 16. The nucleic acid also may be injected by an externally applied local injection apparatus, such as that used to inject antigens for allergy testing; or a transcutaneous patch capable of delivery to subcutaneous muscle. The nucleic acid is injected at one site, or at multiple sites throughout the ischemic tissue.

Once injected, the nucleic acid capable of expressing the desired radioprotective protein is taken up and expressed by the cells of the tissue. Because the vectors containing the nucleic acid of interest are not normally incorporated into the genome of the cells, expression of the protein of interest takes place for only a limited time. Typically, the radioprotectant protein is only expressed at therapeutic levels for about two days to several weeks, preferably for about one to two weeks. Reinjection of the DNA can be utilized to provide additional periods of expression of the radioprotectant protein. If desired, use of a retrovirus vector to incorporate the heterologous DNA into the genome of the cells will increase the length of time during which the therapeutic polypeptide is expressed, from several weeks to indefinitely.

Also contemplated is application of the provided radioprotectant agents via an autoinjector. Thus, another embodiment is the pharmaceutical composition comprising a described radioprotectant agent which is contained in an autoinjector. An autoinjector is a medical device designed to deliver a single dose of a particular (typically life-saving) drug, sometimes also described as a pre-filled syringe for self-injection or for injection by non-medical personnel.

By design, autoinjectors are easy to use and are intended for self-administration by patients or administration by laymen to patients. The site of injection typically is into the thigh or the buttocks, wherein the treatment comprises subcutaneous or intramuscular injection with the peptide or other agent provided herein. Because autoinjectors may be designed to automatically and reliably deliver a desired dose of medicament, they facilitate quick, convenient, and accurate delivery of therapeutic compounds. Autoinjectors are well suited for use by subjects who must self-administer therapeutic substances or by healthcare workers who must inject multiple subjects over a relatively short period of time, for instance, in an emergency situation. Moreover, autoinjectors incorporating a needled injection mechanism may be designed so that the needle is hidden from view before, during, and even after an injection operation, thereby reducing or eliminating any anxiety associated with the act of penetrating a visible needle into the subject's tissue. Though their precise specifications vary widely, needled autoinjectors generally include a body or housing, a needled syringe or similar device, and one or more drive mechanisms for inserting a needle into the tissue of the subject and delivering a desired dose of liquid medicament through the inserted needle. The drive mechanisms included in state of the art needled autoinjectors generally include a source of energy capable of powering the drive mechanism. This energy source may be, for example, mechanical (e.g., spring-loaded), pneumatic, electromechanical, or chemical, as described in U.S. Pat. Nos. 6,149,626, 6,099,504, 5,957,897, 5,695,472, 5,665,071, 5,567,160, 5,527,287, 5,354,286, 5,300,030, 5,102,393, 5,092,843, 4,894,054, 4,678,461, and 3,797,489, the contents of each such patent being incorporated herein by reference. International Publications numbered WO 01/17593, WO 98/00188, WO 95/29720, WO 95/31235, and WO 94/13342 also describe various injectors including different drive mechanisms. Many autoinjectors are (optionally spring-loaded) syringes. An autoinjector of the present invention, in particular, the body or housing thereof that is in direct contact with the radioprotective agent, is preferably made of a material that has a minimal affinity for that agent (e.g., minimal affinity to a peptide or nucleic acid molecule). This can reduce unwanted adhesion or sticking of agent to the autoinjector. One example material that exhibits reduced affinity for peptides is polypropylene, for instance essentially pure polypropylene.

Examples of autoinjectors include Epipen® and Twinject®, which are often prescribed to persons who are at risk for anaphylaxis. Another example of an autoinjector is the Rebiject® for interferon beta used to treat Multiple Sclerosis. Autoinjectors are also used in the military to protect personnel from chemical warfare agents. In the United States military, an autoinjector is part of every Biological or Chemical Weapons Response kit. It is issued to every soldier in the event they may face biological or chemical weapons. An autoinjector herein not only comprises these types of injection devices that usually are spring-driven, whereby the skin penetration and/or the injection of the drug takes place automatically, but also comprises pre-filled syringes, autoinjector cartridges and the like.

The disclosure therefore provides such an autoinjector useful for the treatment of (ir)radiation injury irrespective of whether the radiation is emitted by radioactive substances (radioisotopes), such as uranium, radon, and plutonium, or is produced by man-made sources, such as x-ray and radiation therapy machines. Also provided are autoinjectors comprising a pharmaceutical composition consisting of radioprotective agent (such as a peptide or antibody, or morpholino or other nucleic acid molecule, as described herein) and a suitable excipient.

Suitable excipients, for example, are composed of water, propylene glycol, ethyl alcohol, sodium benzoate and benzoic acid as buffers, and benzyl alcohol as preservative; or of mannitol, human serum albumin, sodium acetate, acetic acid, sodium hydroxide, and water for injections. Other exemplary compositions for parenteral administration via an autoinjector include injectable solutions or suspensions that may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

In one embodiment, an autoinjector comprises as an active ingredient at least one radioprotective agent described herein, such as a radioprotective peptide (or functional analog thereof) that is capable of reducing adverse effects of radiation in a subject when administered after the subject has been exposed to radiation. Preferably, the peptide can confer at least a partial protection against radiation damage if administered at least 30 minutes, more preferably at least one hour, most preferably at least several hours or even several days (such as, three or more days) post-irradiation. This type of autoinjector is also referred to as an "emergency-autoinjector," reflecting its applicability in unexpected emergency situations.

In one embodiment, the autoinjector contains a sterile solution packaged within a syringe-like device that delivers its entire 1 ml to 5 ml contents automatically upon activation. Each milliliter contains 100 mg, or in some embodiments 200 mg, radioprotective agent (e.g., peptide) with an excipient, such as an excipient comprising propylene glycol, ethyl alcohol, sodium benzoate and benzoic acid as buffers, and benzyl alcohol as preservative.

The therapeutic agents can also be administered directly as part of a surgical or other medical procedure, or at the bedside by a treating physician. Drug quality product (e.g., peptide, antibody or morpholino) can be diluted for instance in sterile saline and given by injection using sterile 1 cc syringes and small bore needles (25 gauge and less) to a subject in need of radioprotection. Alternatively, a wound bed can be irrigated for instance with a saline or other therapeutically effective solution containing a known concentration (dosage) of drug or compound, or a combination thereof. Precise control and localization of therapeutic effects can thus be obtained.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic peptide as a central core. In microspheres, the therapeutic agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Also contemplated is the use of nanoparticles as delivery agents, which can be targeted to specific cells, tissues or organ for instance by incorporation on their surface ligands of receptors specific in their expression to the targeted cells, tissues or organs, The targeting entity can be the same or different than the therapeutically active agent carried by the nanoparticle. Further, distribution of nanoparticles to certain tissues spaces (e.g. the blood versus the central nervous system protected by the blood-brain barrier) can be determined by altering the size of the nanoparticles thereby allowing or preventing their transit of such barriers between tissue compartments.

Polymers can be used for ion-controlled release. Various degradable and nondegradable polymeric matrices for use in controlled drug delivery are known in the art (Langer, *Accounts Chem. Res.* 26:537, 1993). For example, the block copolymer, poloxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of lipid-capsulated compounds (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

The specific form of the agents and their manner of administration depends in part upon the particular tissue to be treated. The compounds or pharmaceutical compositions containing them can be applied, for example, as a mouthwash to coat the oral mucosal tissue, as a spray or syringe to coat the mucosal tissues of the nose and/or throat, or as a cream or paste, an enema, or other forms of topical administration known to one of skill in the art, as appropriate.

The amount of agent to be delivered, as well as the dosing schedule necessary to provide the desired radio/chemo protective effects, will be influenced by the bioavailability of the specific compound selected (and/or an active metabolite thereof), the type and extent of radiation exposure or radiation dosage schedule, and other factors that will be apparent to those of skill in the art.

Alternatively, the compound may be administered in a gel, lotion, ointment or other suitable form which is applied to the tissue up to about 90 minutes before irradiation or treatment and remains on the tissue during and optionally after the treatment.

The same dosage and concentrations can be used when the radioprotective agent is administered after irradiation and/or radiotherapeutic treatment. The three administrations (before, during and after radiotherapy treatment) may be used alone, or in any combination of two or all three administrations, as needed.

XI. Suppression of Protein Expression

In some embodiments, it is desirable to reduce or suppress TSP1 or CD47 protein expression, for example in various experimental conditions or in the treatment or amelioration of radiation exposure, such as exemplified herein.

Although the mechanism by which antisense RNA molecules interfere with gene expression has not been fully elucidated, it is believed that antisense RNA molecules (or fragments thereof) bind to the endogenous mRNA molecules and thereby inhibit translation of the endogenous mRNA or result in its degradation. A reduction of protein expression in a cell may be obtained by introducing into cells an antisense construct based on the TSP1 (or CD47) encoding sequence, including the human (or other mammalian) TSP1 cDNA or CD47 cDNA or gene sequence or flanking regions thereof. For antisense suppression, a nucleotide sequence from a TSP1-encoding sequence, for example all or a portion of the TSP1 cDNA or gene, is arranged in reverse orientation relative to the promoter sequence in the transformation vector. One of ordinary skill in the art will understand how other aspects of the vector may be chosen.

The introduced sequence need not be the full length of the cDNA or gene, or reverse complement thereof, and need not be exactly homologous to the equivalent sequence found in the cell type to be transformed. Generally, however, where the introduced sequence is of shorter length, a higher degree of homology to the native target sequence will be needed for effective antisense suppression. The introduced antisense sequence in the vector may be at least 20 nucleotides in length, and improved antisense suppression will typically be observed as the length of the antisense sequence increases. The length of the antisense sequence in the vector advantageously may be greater than about 30 nucleotides, or greater than about 100 nucleotides. For suppression of the TSP1 gene itself, transcription of an antisense construct results in the production of RNA molecules that are the reverse complement of mRNA molecules transcribed from the endogenous TSP1 gene in the cell.

Suppression of endogenous TSP1 or CD47 expression can also be achieved using ribozymes. Ribozymes are synthetic molecules that possess highly specific endoribonuclease activity. The production and use of ribozymes are disclosed in U.S. Pat. No. 4,987,071 and U.S. Pat. No. 5,543,508. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Suppression can also be achieved using RNA interference, using known and previously disclosed methods. Several models have been put forward to explain RNAi, in particular the mechanisms by which the cleavage derived small dsRNAs or siRNAs interact with the target mRNA and thus facilitate its degradation (Hamilton et al., *Science* 286, 950, 1999; Zamore et al., *Cell* 101, 25, 2000; Hammond et al., *Nature* 404, 293, 2000; Yang et al., *Curr. Biol.* 10, 1191, 2000; Elbashir et al., *Genes Dev.* 15, 188, 2001; *Bass Cell* 101, 235, 2000). It has been proposed that the cleavage derived small dsRNAs or siRNAs act as a guide for the enzymatic complex required for the sequence specific cleavage of the target mRNA. Evidence for this includes cleavage of the target mRNA at regular intervals of ~21-23 nts in the region corresponding to the input dsRNA (Zamore et al., *Cell* 101, 25, 2000), with the exact cleavage sites corresponding to the middle of sequences covered by individual 21- or 22 nt small dsRNAS or siRNAs (Elbashir et al., *Genes Dev.* 15, 188, 2001). Although mammals and lower organisms appear to share dsRNA-triggered responses that involve a related intermediate (small dsRNAs), it is likely that there will be differences as well as similarities in the underlying mechanism. dsRNAs can be formed from RNA oligomers produced synthetically (for technical details see material from the companies Xeragon and Dharmacon, both available on the internet). Small dsRNAs and siRNAs can also be manufactured using standard methods of in vitro RNA production. In addition, the Silencer™ siRNA Construction kit (and components thereof) available from Ambion (Catalog #1620; Austin, Tex.), which employs a T7 promoter and other well known genetic engineering techniques to produce dsRNAs. Double stranded RNA triggers could also be expressed from DNA based vector systems.

Inhibition also can be accomplished using morpholino oligonucleotides, for instance as described herein. The herein described discoveries and therapeutics find immediate application through implanted devices in the management and treatment, for instance, accidental or intentional radiation exposure. The morpholino can be delivered systemically as herein described. Morpholinos targeting CD47 or TSP1 can also be incorporated into (or onto) an implanted device for sustained local release directly to enhance radioprotection. The therapeutic agents (e.g., morpholino, antibody, peptide) could be then targeted specifically to area(s) of maximum benefit throughout the body including for instance a site that is to undergo (or which has undergone or is undergoing) radiation therapy. In more general applications, various implantable scaffolds or synthetics can serve the same means by allowing for controlled and extended release of the therapeutic agent. With regard to accidental radiation exposure particularly (but not exclusively), the therapeutics can be incorporated directly into wound dressing and gels and applied directly to a wound surface. In localizing the therapeutic to the area needed, potential negative side effects derived from non-specific roles of TSP1 and CD47 can be limited and/or controlled.

The radioprotective nucleic acids and nucleic acid analogs that are used to suppress endogenous TSP1 or CD47 expression may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and modified linkages (for example, alpha anomeric nucleic acids, etc.). The term nucleic acid molecule also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Additionally, although particular exemplary sequences are disclosed herein for use as radioprotectant agents, one of skill in the art will appreciate that the present methods also encompass sequence alterations of the disclosed agents that yield the same results as described herein. Such sequence alterations can include, but are not limited to, deletions, base modifications, mutations, labeling, and insertions.

Suppression of protein expression may also be achieved through agents that enhance proteolysis of CD47 or TSP1 (Allen et al., *Endocrinology* 150:1321-1329, 2009). In other particular examples, the suppression of CD47 expression involves an agent that enhances the removal of CD47 from the cell surface or decreases the transcription, mRNA processing, or translation of CD47. Similar embodiments are envisioned, regarding suppression of TSP1.

XII. Screening for Additional Agents that Affect TSP1/CD47 Activity and/or Interaction In various embodiments, it may be useful to treat a subject expected to be exposed to radiation, or suspected of being so exposed, with an agent that inhibits a TSP1 or CD47 activity or interaction. Examples of such methods are described herein, along with example compounds and compositions useful in such methods. However, equivalents of the specifically described compounds are also useful in these methods. Thus, here described are methods for identifying agents with TSP1 or CD47 inhibitory activity, methods of identifying agents that interfere with an interaction between a TSP1 polypeptide and a CD47 polypeptide, and so forth.

Compounds which may be screened in accordance with this disclosure include, but are not limited to peptides, antibodies and fragments thereof, and other organic or inorganic compounds (for example, peptidomimetics, small molecules) that inhibit TSP1 and/or CD47 activity as described herein, or interfere (directly or indirectly) with an interaction between TSP1 and CD47. Such compounds may include, but are not limited to, peptides such as, for example, soluble peptides, including but not limited to members of random peptide libraries; (see, for example. Lam et al., *Nature,* 354:82-84, 1991; Houghten et al., *Nature,* 354:84-86, 1991), and combinatorial chemistry-derived molecular library made of D- and/or L-configuration amino acids, phosphopeptides (including, but not limited to, members of random or partially degenerate, directed phosphopeptide libraries; see, for example, Songyang et al., *Cell,* 72:767-778, 1993), antibodies (including, but not limited to, polyclonal, monoclonal, humanized, anti-idiotypic, chimeric or single chain antibodies, and Fab, $F(ab')_2$ and Fab expression library fragments, and epitope-binding fragments thereof), and small organic or inorganic molecules.

Computer modeling and searching technologies permit identification of compounds, or the improvement of already identified compounds that can modulate expression or activity of TSP1 or CD47. Examples of molecular modeling systems are the CHARMM (Chemistry at HARvard Molecular Mechanics) and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific-proteins, such as Rotivinen et al., *Acta Pharmaceutical Fennica* 97:159-166, 1988; Ripka, *New Scientist* 54-57, 1988; McKinaly and Rossmann, *Annu Rev Pharmacol Toxicol* 29:111-122, 1989; Perry and Davies, *OSAR: Quantitative Structure-Activity Relationships in Drug Design pp.* 189-193, 1989, (Alan R. Liss, Inc.); Lewis and Dean, *Proc R Soc Lond* 236:125-140 and 141-162, 1989; and, with respect to a model receptor for nucleic acid components, Askew et al., *J Am Chem Soc* 111:1082-1090, 1989. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

One could also screen libraries of known compounds, including natural products or synthetic chemicals, and biologically active materials, including proteins, for compounds which are inhibitors or activators. Agents identified by the assays described herein may be selected for further study if, for example, they show a statistically different result from a control. Example statistical analysis is provided in the examples. A statistically significant result is then considered to be one in which $p<0.05$, in certain embodiments.

Disclosed herein are methods of identifying agents with potential for inhibition of TSP1 or CD47, and particularly the activity of either of these proteins in influencing tissue survival to radiation exposure. Any agent capable of inhibiting (to a measurable degree) at least one biological activity of TSP1 or CD47 is contemplated. In some embodiments, a TSP1 (or CD47) inhibitory agent interferes with an interaction between TSP1 and CD47.

Compounds identified may be useful, for example, in modulating an activity of TSP1 or CD47, or increasing or decreasing a binding affinity between TSP1 and CD47, thereby providing radioprotection and/or reducing adverse effects, particularly in soft tissues, of radiation exposure.

The following examples are provided to illustrate certain particular features and/or embodiments. These examples should not be construed to limit the invention to the particular features or embodiments described.

EXAMPLES

Example 1

Thrombospondin-1 and CD47 Limit Cell and Tissue Survival of Radiation Injury Thrombospondin-1 is a potent antagonist of NO/cGMP signaling in ischemic soft tissues. This example demonstrates that soft tissues in thrombospondin-1 null mice are remarkably resistant to radiation injury. Twelve hours after 25 Gy hind limb irradiation, thrombospondin-1 null mice show significantly less cell death in muscle and bone marrow. Two months following irradiation, skin and muscle units in the null mice show minimal histological evidence of radiation injury and near full retention of mitochondrial function. Tissue perfusion and acute vascular responses to NO are also preserved in irradiated thrombospondin-1 null hind limbs. The role of thrombospondin-1 in radiosensitization is specific in that thrombospondin-2 null mice were not protected. However, mice lacking the thrombospondin-1 receptor CD47 showed similar radioresistance as thrombospondin-1 null mice. Thrombospondin-1- and CD47-dependent radiosensitization is cell autonomous because vascular cells isolated from the respective null mice showed dramatically increased survival and improved proliferative capacity following irradiation in vitro.

Introduction

Radiation remains a primary mode of cancer therapy, with one half of newly diagnosed cancer patients receiving some form of radiation therapy. Free radicals generated by ionizing radiation acutely damage cellular DNA and other cellular macromolecules, eliciting stress responses that ultimately lead to cell death (Chapman, *Int J Radiat Biol* 79:71-81, 2003). Because DNA damage compromises the ability of cells to undergo mitosis, the tissues most sensitive to effects of radiation are generally those undergoing rapid proliferation. Several mechanisms contribute to radiation-induced cell death, including mitotic death, apoptosis, and cell cycle arrest. The mechanism and extent of cell death depend on cell type, cell environment, and the radiation dose. Bystander effects of the direct radiation damage can cause can lead to additional cell death through either direct cell contact or release of intracellular mediators (Prise et al., *Lancet Oncol* 6:520-528, 2005). Ultimately, radiation damage results in death of both cancer and normal cells. Therefore, limiting toxicity to adjacent normal tissues restricts the therapeutic dosage of radiation that can be delivered to a given tumor.

In addition to using 3-dimensional conformal radiation therapy to maximize radiation delivery to tumor versus adjacent healthy tissues (Purdy, *From Radial Ther Oncol* 40:18-39, 2007), a second approach to improve the therapeutic window for radiotherapy involves use of chemical radiosensitizers or radioprotectants. General chemical radiosensitizers or pathway-specific sensitizers (such as histone deacetylase inhibitors or inhibitors of Ras signaling) have been used to increase the radio sensitivity of tumors (Poggi et al., *Curr Probl Cancer* 25:334-411, 2001; Karagiannis et al., *Oncogene* 25:3885-3893, 2006; McKenna et al., *Oncogene* 22:5866-5875, 2003). Conversely, amifostine and nitroxides such as Tempol have demonstrated radioprotective activities for adjacent tissues (Poggi et al., *Curr Probl Cancer* 25:334-411, 2001; Cotrim et al., *Clin Cancer Res* 13:4928-4933, 2007).

Tissues may also produce endogenous radioprotectants in response to radiation injury. Nitric oxide (NO) is a primary regulator of mammalian physiology. Radiation increases NO production in vascular cells, and NO can protect cells and tissues from radiation damage by stimulating soluble guanylate cyclase (sGC) production of cGMP to promote cell survival pathways and by several cGMP-independent effector pathways (Freeman et al., *Gut* 53:214-221, 2004; Leach J et al., *J Biol Chem* 277:15400-15406, 2002; Zhong et al., *Life Sci* 74:3055-3063, 2004). Consistent with these studies, pretreatment of mice with exogenous NO prolongs their survival following a lethal dose of whole body irradiation (Liebmann et al., *Cancer Res* 54:3365-3368, 1994). However, studies using iNOS inducers and NOS inhibitors indicate that elevated NO production can also contribute to radiation injury (Ohta et al., *Biol Pharm Bull* 30:1102-1107, 2007). Furthermore, NOS2 gene transfer into tumors increased their radiosensitivity (Cook et al., *Cancer Res* 64:8015-8021, 2004), and NOS1 null mice show increased radioresistance in bone marrow (Epperly et al., *Exp Hematol* 235:137-145, 2007). These apparently conflicting observations could be rationalized if the effects of NO on radiation injury are biphasic and the radioprotective activity of NO occurs at low doses, which typically involve cGMP signaling.

It was recently reported that the matricellular protein, thrombospondin-1 (TSP1) blocks NO-stimulated activation of sGC (Isenberg et al., *Proc Natl Acad Sci USA* 102:13141-13146, 2005; Isenberg et al., *Cardiovasc Res* 71:785-793, 2006) and that this process requires engagement of the cell surface receptor CD47 (Isenberg et al., *J Biol Chem* 281:26069-26080, 2006). Targeting TSP1 or CD47 enhances ischemic tissue survival and blood flow (Isenberg et al., *Arterioscler Thromb Vasc Biol* 27:2582-2588, 2007; Isenberg et al., *Blood* 109:1945-1952, 2007; Isenberg et al., *Circ Res* 100:712-720, 2007). CD47 engagement may also induce apoptosis of some cell types independent of NO (Manna et al., *J Biol Chem* 280:29637-29644, 2005; Bras et al., *Mol Cell Biol* 27:7073-7088, 2007). In view of these studies, we hypothesized that inhibition of NO signaling by TSP1 might limit the radioprotective activity of NO. We tested this hypothesis using TSP1 and CD47 null mice and demonstrate here that the absence of these proteins significantly improves tissue survival of radiation. Furthermore, we demonstrate that the radiosensitizing activity of TSP1 signaling via CD47 is cell autonomous.

Materials and Methods

Animals: Wild type, TSP1 null, and CD47 null mice in C57BL/6 background were housed in a pathogen free environment and had ad libitum access to standard rat chow and water. TSP2 null male mice 12 weeks of age and matched wild type B6129sf1/J control animals were obtained from Jackson Labs (Bar Harbor, Me.). Care and handling of animals was in compliance with standards established by the Animal Use and Care Committee of the National Cancer Institute.

Reagents and cells: Primary murine vascular endothelial cells were harvested from wild type, TSP 1, CD47 and TSP2 null mice and cultured as previously described in endothelial growth media (Lonza, Switzerland) (Isenberg et al., *Proc Natl Acad Sci USA* 102:13141-13146, 2005). Murine B16F10 melanoma cells were kindly provided by Dr. Lyuba Varticovski (NCI) and grown in RPMI with 10% FCS (Gibco, Grand Island. NY).

Irradiation of mice: Age and sex matched wild type, TSP1. CD47 and TSP2 null mice underwent local irradiation to the right hind limb as previously described (Flanders et al., *Am J Pathol* 160:1057-1068, 2002). Briefly animals (without anesthetics) were placed in customized Lucite jigs that allow for immobilization and selective irradiation of the leg. A single radiation dose of 25 Gy was delivered by a Therapax DXT300 X-ray irradiator (Pantak, Inc., East Haven, Conn.) using 2.0-mm A1 filtration (300 kVp) at a dose rate of 2.53 Gy/min Care was taken to avoid irradiation of other body parts by using lead shields specifically designed as a part of the jigs. After irradiation, the animals were placed in cages as indicated above and observed daily for 8 weeks at which time animals were euthanized and tissues fixed in formalin 10% for further analysis.

In other experiments, mice receiving 25 Gy to the hind limb were euthanized 12 hours later and hind limbs fixed in 10% formalin. Unstained tissue sections were prepared on charged slides from paraffin embedded hind limbs for in situ analysis of apoptosis as described.

Radiation growth delay assay: C57BL/6 wild type and TSP1 null 12 week old female mice were inoculated with syngeneic B6F10 melanoma cells ($2.5\times10^6$ cells/animal) to the right lateral thigh. When tumor volume reached 200 $mm^3$ half of each group underwent 10 Gy irradiation to the tumor-bearing limb. Tumor size was measured with calipers bi-weekly by the same investigator. Tumor volume was calculated by the formula: volume=$W^2\times L/2$, where W=shortest diameter and L=longest diameter. Animals were sacrificed if tumors exceeded 2 $cm^3$ or at 26 days. Results are from 16 animals, 8 of each strain.

Irradiation of cells: Primary murine lung derived endothelial cells were plated in standard growth medium in 96- or 6-well culture plates (Nunc) and allowed to adhere. Irradiation was done on a Precision X-Ray X-Rad 320 (East Haven, Conn.) operating at 300 kV/10 mA with a 2 mm aluminum filter. The dose rate at 50 cm from the x-ray source was 242 cGy/minute, as determined by multiple thermoluminescent dosimeter readings.

Skin reaction: Skin reaction following hind limb irradiation was quantified every week following treatment for 8 weeks using a previously described grading system (Flanders et al., *Am J Pathol* 163:2247-2257, 2003). The grading system consisted of 5 categories: normal, hair loss, erythema, dry desquamation and moist desquamation/ulceration.

Leg contraction assay: Measurement of hind limb extension was performed as previously described with modification (Flanders et al., *Am J Pathol* 160:1057-1068, 2002). Animals were placed under light general anesthesia with 1% isoflurane via nose cone, and the pelvis was immobilized against a post fixed to the examination table. The treated and untreated limbs were then placed individually under a defined degree of tension and the distance of extension measured.

Blood oxygen level dependent (BOLD) MRI imaging: MRI images were acquired using a Bruker Biospin 4.7 T scanner and isoflurane anesthesia. Muscle tissue scanned was at rest, so alterations in oxygenation reflected changes in perfusion rather than in oxygen consumption. MR measurements were started after the mouse's body temperature reached 37° C. Prior to the experiments, gradient echo based $T_1$ sequence was used to determine the target slice location. A series of $T_2$* weighted gradient echo BOLD image data sets at transverse to the midpoint of the femur were repeatedly acquired for 30 min to monitor temporal changes in blood oxygenation and blood flow. Diethylamine-NONOate (DEA/NO, 100 nmol/g body weight) was injected with saline via the rectal cannula 5.0 min after starting the scan. Imaging parameters used were: TR=450 ms, Flip angle=45, Nex=1, slice thickness=2 mm, matrix size=64×64, total imaging time for the series was 29 min.

Laser Doppler analysis: Hind limb flow was measured using laser Doppler imaging (MoorLD1-2λ, Moor Instruments, Devon, England). Briefly, animals were placed in a supine position on a heating pad, and anesthesia was provided by 1% inhalation isoflurane in a 50:50 mixture of oxygen to room air. Core temperature was monitored by rectal probe and was further controlled with a heat lamp. The hair of the ventral surface of the anterior abdominal wall or respective hind limb was clipped and depilated with Nare™ and a region of interest (ROI) marked. After equilibration to the experimental set-up baseline, hind limb blood flow was measured. The following instrument settings were used: override distance 21 cm; scan time 4 msec/pixel. Results are expressed as the change percent control from baseline of the ROI.

Mitochondrial DNA analysis: Primer sequences were derived using FastPCR (accessible on the World Wide Web at primerdigital.com/index.php?page=35) and were chosen to amplify approximately 100 bp regions of unique genomic and mitochondrial genes using quantitative PCR. DNA was quantified by measuring fluorescent intensity using Taq polymerase amplification in a SYBR green reaction mixture (Thermo Fisher Scientific) with an MJ Research Opticon I instrument (Biorad, Herecules, Calif.). Data were processed using the Opticon I software supplied with the instrument. Melting curve analysis was performed for each sample to insure a single product was produced in each reaction. The cycling parameters consisted of an initial denaturation at 95° C. for 15 min, followed by 40 cycles of denaturation at 94° C. and annealing at 60° C. for 20 sec each with extension for 30 sec at 72° C., ending with a final extension at 72° C. for 10 min Melting temperatures were determined in 0.2° C. steps from 60 to 95° C. with a dwell time of 8 sec. Gene copy number was assessed using 2-fold dilutions of genomic DNA samples from mouse muscle tissue samples. Samples were normalized using PKD1 as an internal control standard. The gene identification numbers are listed followed by the coordinates of the first gene primer.

PKD1 polycystin 1 NT_039649.6 (nuclear), 0917160

```
ACCGACTCAACCAGGCCACAG,     (SEQ ID NO: 6)

GGAGGTCCATTGTGCCCATGG;     (SEQ ID NO: 7)
```

GTF2IRD1 General transcription factor, NT_039314 (nuclear), 4559250

```
AGGGACCGCCTCCACAAGCTG,     (SEQ ID NO: 8)

TCTCCGTGCAGGAACTGGCTG;     (SEQ ID NO: 9)
```

Osteocalcin NM_001032298.2 (nuclear), 255 ACCCTGCTTGTGACG (SEQ ID NO: 10), GCTTTAGGGCAGCACAGGTCC (SEQ ID NO: 11);

NADH6 NC_005089.1 (mitochondrial), 13587 CCGCAAACAAAGATCACCCAG (SEQ ID NO: 12), GTTGGAGTTATGTTGGAAGGAGG (SEQ ID NO: 13); and 6s rRNA NC_005089.1 (mitochondrial) 1432, GCTIGGTGATAGCRIGTTACC (SEQ ID NO: 14), TCCGTTCCAGAAGAGCTGTCC (SEQ ID NO: 15).

Cell survival assay: Wild type, TSP1 null and CD47 null or TSP2 null and wild type B6129sf1/J lung derived endothelial cells were resuspended in EGM medium and seeded into 96-well plates (Nunc, Denmark) at a density of $5\times10^3$ cells/200 μl per well and incubated for 24 hours at 37° C. Cells were then exposed to a single dose of gamma radiation (0, 10, 20, 30, and 40 Gray) and allowed to incubate another 72 hours at 37° C. Cell viability was determined with the CellTiter 96 AQueous One Solution Cell Proliferation Assay (Promega, Madison, Wis., USA) as per the manufacture's instructions and absorbance at 490 nm determined using an MR580 Microelisa Auto Reader (Dynatech, Alexandria, Va.).

Cell proliferation assay: Proliferation was assessed by quantifying incorporation of bromodeoxyuridine (BrdU) into newly synthesized DNA using a BrdU Cell Proliferation Assay (Calbiochem, La Jolla, Calif.). Primary murine wild type, TSP1, TSP2, and CD47 null lung endothelial cells were seeded into 96 well plates at $5\times10^4$ cells/well density. After 24 hours incubation at 37° C. treatment groups were irradiated at 40 Gy. Control and irradiated plates were assayed for BrdU uptake over 24 hours starting at 48 to 168 hours post-radiation. The assay was performed according to the manufacturer's protocol, and the plates were read at 420 nm.

Mitochondrial viability assay: Mitochondrial viability of hind limb muscle biopsies was assessed by the reduction of a tetrazolium salt to water insoluble formazan through mitochondrial oxidation as described (Isenberg et al., *Blood* 109: 1945-1952, 2007). Results were expressed as absorbance normalized to dry tissue weight.

Tissue apoptosis: The ApopTag in situ detection kit (Chemicon, Millipore, Mass.) was employed following the manufacturer's recommendations In brief, sections undergo deparaffinization, rehydration and washing, followed by treatment with 20 μg/ml of proteinase K for 15 minutes at room temperature and repeat washing. Endogenous peroxidase activity was quenched with 3% $H_2O_2$ in PBS for 5 minutes. The 3'-hydroxy DNA strand breaks were enzymatically labeled with digoxygenin nucleotide via TdT and incubated for 1 hour at 37° C., and the reaction terminated with a stop buffer. Sections were then incubated with anti-digoxygenin peroxidase for 30 minutes at room temperature, washed, stained with 3-3' diaminobenzidine substrate, counterstained with methyl green and mounted. Positive and negative control slides provided with the kit are used in each assay to insure consistency.

Histology: Tissue units were excised, fixed in 10% buffered formaldehyde, paraffin embedded, and sectioned at a thickness of 5 μm. Sections were then stained with hematoxylin and eosin (II&E). Review of each slide was performed by an independent pathologist blinded to the origin of each tissue slide.

Immunohistochemistry: Paraffin embedded hind limbs were sectioned at a thickness of 5 μm and applied to charged glass slides and processed for immunohistology. Tissue sections were deparaffinized with xylene and rehydrated in alcohol. Slides were then heat inactivated in 10 mmol/L sodium citrate (pH 6.0) in a microwave for 5 minutes. Cooled slides were rinsed with PBS and then incubated with 3% $H_2O_2$ for 30 minutes at room temperature. Sections were then blocked with 5% normal goat serum in PBS for 30 minutes at room temperature followed by 12 hour incubation in a humidified chamber at 37° C. with a monoclonal CD31 antibody (clone JC70A, DakoCytomation, Denmark) at a 1:40 dilution. Slides were washed and then incubated with secondary antibody, washed and incubated in pre-diluted Streptavidin-HRP conjugate (BD PharMingen). Color was developed by DAB substrate kit (BD PharMingen).

Statistics: All experiments were replicated at least three times. Results are presented as the mean±SD with analysis of significance done by the Student's t test or one-way ANOVA with Tukey post hoc test where indicated using Origin software (version 7, OriginLabs Corp., Northhampton, Mass.), with significance taken at p values <0.05.

Results

TSP1 and CD47 Null Mice Show Tissue Preservation Following Radiation Injury.

Figure 1A:
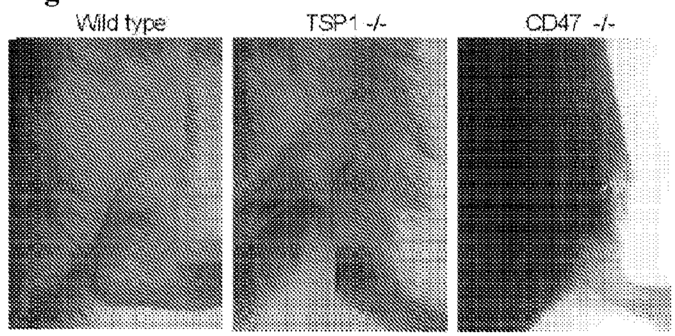
FIG. 1. TSP1 and CD47 limit survival of irradiated soft tissue. Age and sex matched C57BL/6 wild type, TSP1 and CD47 null mice received 25 Gy irradiation to the right hind limb (FIG. 1A). Tissue changes were assessed every week, and scores are presented for two months (FIG. 1B). Significance was determined using the independent two-sample t-test. *$P<0.05$ versus wild type. Representative H&E stained sections of muscle and skin are shown from irradiated hind limbs harvested after two months (20×) (FIG. 1C). Mitochondrial viability of hind limb muscle biopsies was assessed at two months post-irradiation by the reduction of a tetrazolium salt to water insoluble formazan through mitochondrial oxidation as described (FIG. 1D). Significance was determined using the independent two-sample t-test. *$P<0.05$ versus wild type non-radiated. Results were expressed as absorbance normalized to dry tissue weight. Copy numbers in control and irradiated muscle tissue harvested at two months were determined for two mitochondrial genes (NADH6 and 16s rRNA, mt-Rnr2) and two nuclear genes (the general transcription factor Gtf2ird1 and osteocalcin, Bglap2) by quantitative PCR (FIG. 1E). For each sample, results were normalized to the nuclear gene Pkd1.
Figure 1B:
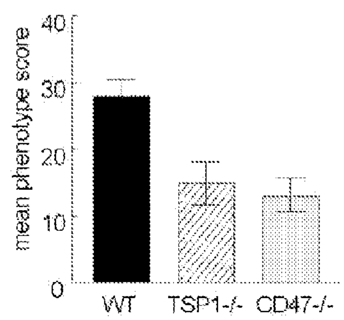
Figure 1C:
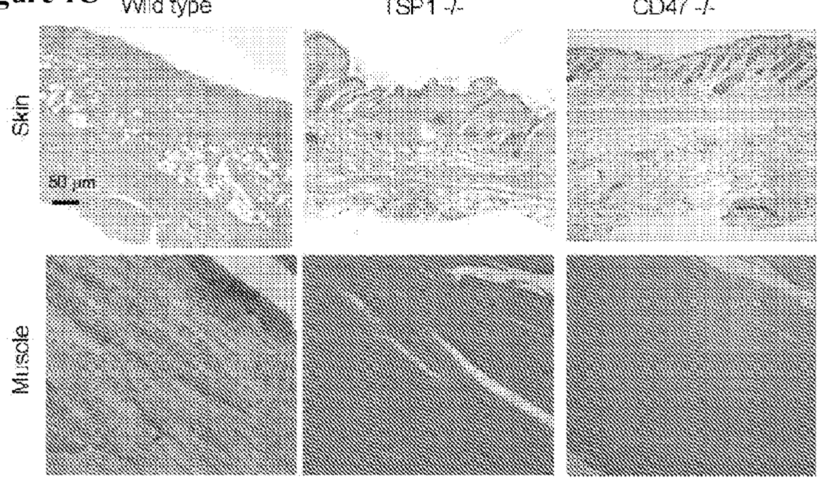

Previous studies identified a role for TSP1 in inducing developmental hair loss during the catagen phase (Yano K et al., *J Invest Dermatol* 120:14-19, 2003). Extending this observation to radiation alopecia, we observed less hair loss 8 weeks post-treatment on the irradiated hind limbs of TSP1 null mice compared to age and sex matched wild type mice (FIG. 1A). An even more dramatic preservation of hair viability was observed for the hind limbs of irradiated CD47 null mice. Moreover, irradiated skin on the-treated null mice showed minimal to no skin ulceration or wet desquamation (FIG. 1A). When scored using the grading system of Flanders (Flanders et al., *Am J Pathol* 160:1057-1068, 2002; Flanders et al., *Am J Pathol* 163:2247-2257, 2003), wild type animals demonstrated both accelerated skin changes and more substantial final changes in skin phenotype compared to null animals (FIG. 1B). Histologically, hair follicles and skin architecture were better preserved 8 weeks post-irradiation in TSP1 nulls and essentially normal in the CD47 nulls (FIG. 1C).

Figure 1D:
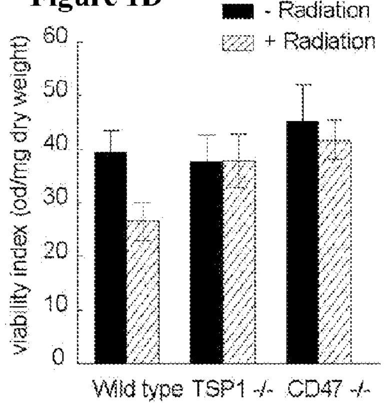

Remarkably, tissue preservation in the irradiated null mice also extended to the underlying skeletal muscle. H&E stained sections of irradiated wild type muscle showed significant loss of muscle fibers and nuclei, but these were largely intact in irradiated tissue sections from TSP1 and CD47 null animals (FIG. 1C). Mitochondrial viability in irradiated muscle tissue was assessed by tetrazolium salt reduction (FIG. 1D). In contrast to the expected loss of mitochondrial viability in irradiated wild type muscle, mitochondrial viability assessed 8 weeks post irradiation was significantly greater in muscle biopsies from irradiated hind limbs in both TSP1 and CD47 null mice, with no significant difference between the irradiated and control limbs in these mice (FIG. 1D).

Figure 1E:
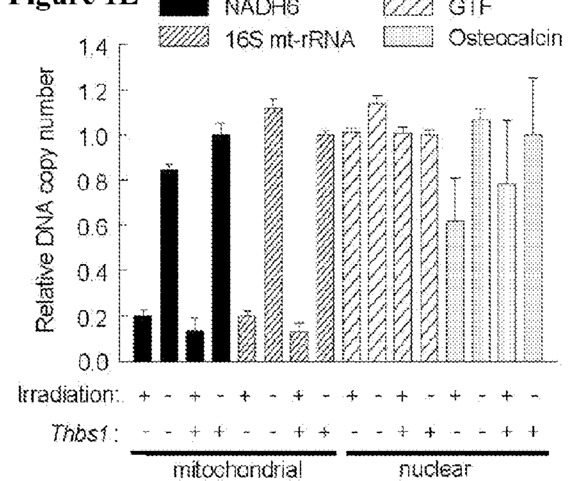

This preservation of mitochondrial function in the TSP1 null mice occurred despite the expected substantial loss in copy number for two mitochondrial genes (NADH6 and 16S mtRNA) compared to that for two nuclear genes in the irradiated tissue as expected due to the relatively inefficient DNA repair processes in mitochondria (Prithivirajsingh et al., *FEES Lett* 571:227-232, 2004). Selective loss of the mitochondrial genes was similar in the TSP1 nulls (FIG. 1E), indicating that TSP1 has no effect on the level of immediate DNA damage caused by radiation or on the subsequent level of mitochondrial DNA repair.

Thrombospondin-2 is not a Radiosensitizer

Figure 2A:
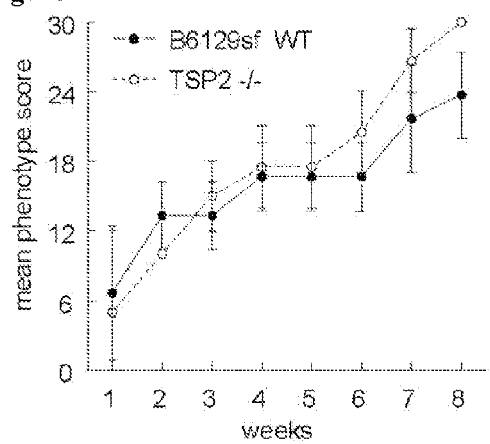
FIG. 2. TSP2 does not modulate radiation-induced tissue damage. Age and sex matched B6129sf1/J wild type and TSP2 null mice received 25 Gy to the right hind limb. Tissue changes were assessed every week and scored over the next 2 months (FIG. 2A). Mitochondrial viability of hind limb muscle biopsies was assessed at 2 months by the reduction of a tetrazolium salt to water insoluble formazan through mitochondrial oxidation as described (FIG. 2B). Results were expressed as absorbance normalized to dry tissue weight. These in vivo experiments demonstrate that the other subfamily member TSP2 does not limit radiation tissue survival.
Figure 2B:
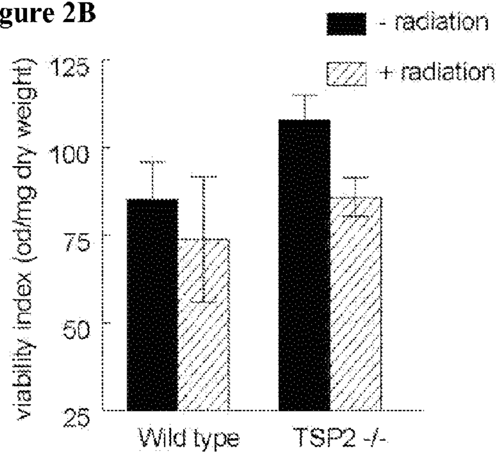

In contrast to the TSP1 null mice, TSP2 null mice in a B6129sf1/J background demonstrated significant hair loss and skin damage following radiation at the gross tissue level. Recovery from irradiation did not differ between the TSP2 null and wild type mice in the same background over the 8 week period studied (FIG. 2A). Mitochondrial viability in irradiated muscle tissue was assessed by tetrazolium salt reduction and demonstrated a comparable decrease in viability between wild type and TSP2 null muscle samples (FIG. 2). H&E stained sections from irradiated wild type and TSP2 null hind limbs showed comparable levels of muscle fiber and nuclei loss, and no tendency towards vascular remodeling was found in TSP2 null irradiated hind limbs.

TSP1 and CD47 Null Mice Demonstrate Enhanced Leg Extension Following Radiation Injury.

Figure 3:
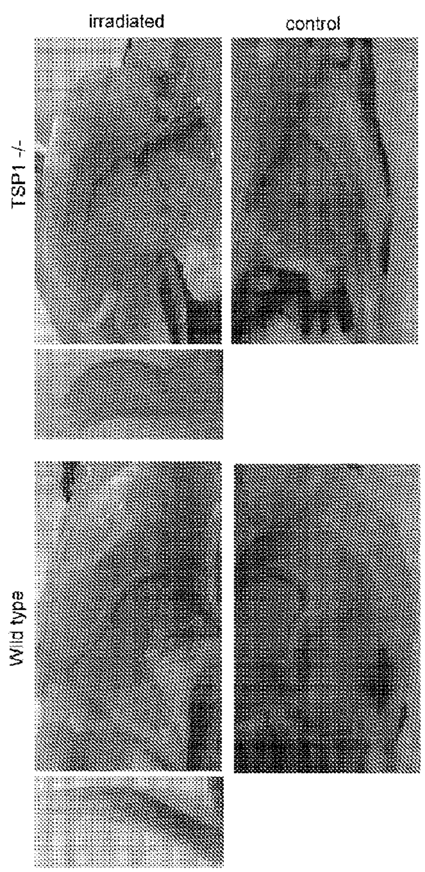
FIG. 3. TSP1 null animals demonstrate hypertrophy of hind limbs following radiation. Age and sex matched C57BL/6 wild type and TSP1 null mice received 25 Gy irradiation to the right hind limb. The cutaneous envelope of the medial hind limb was excised exposing the femoral vein and artery. Representative images at 8 weeks post-radiation are presented.
Figure 4:
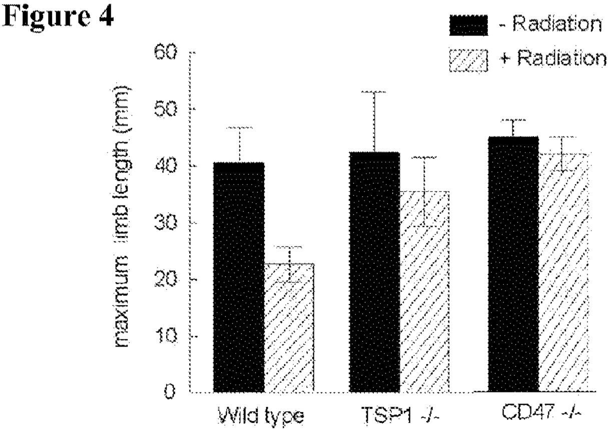
FIG. 4. Limb flexibility is preserved in irradiated tissue in the absence of TSP1. Limb extension in age and sex matched C57BL/6 wild type, TSP1 and CD47 null mice was measured as described eight weeks following 25 Gy to the right hind limb. Significance was determined using the independent two-sample t-test. *$P<0.05$ versus wild type non-irradiated.

In addition to demonstrating significant resistance to cutaneous injury following radiation, irradiated hind limbs of TSP1 and CD47 null animals did not show any atrophy at 8 weeks. Rather, there was a tendency towards hypertrophy of the limb soft tissues and vascular elements as compared to irradiated limbs in wild type animals and control non-irradiated limbs (FIG. 3). TSP2 null hind limbs did not show hypertrophy. Limb flexibility, quantified as the maximum degree of limb lengthening, was preserved in TSP1 and CD47 null hind limbs 8 weeks after 25 Gy of radiation (FIG. 4). In contrast, wild type limbs demonstrated the expected loss of extension.

TSP1 and CD47 Limit Radiation-Induced Alterations in Vascular Response.

Figure 5A:
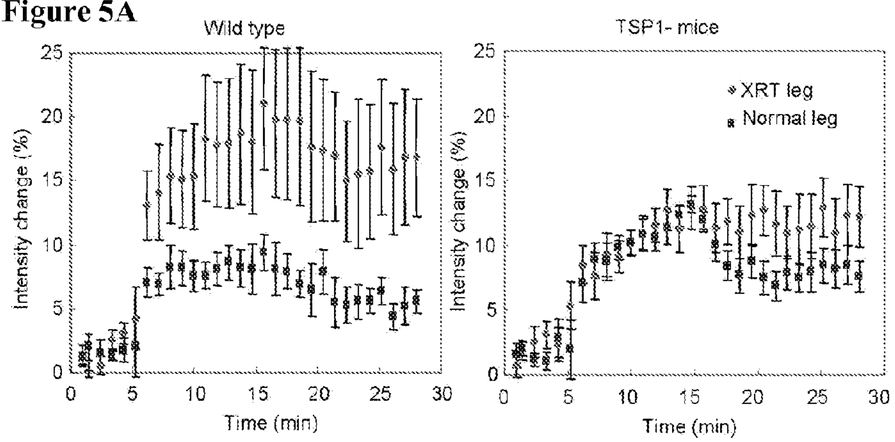
FIG. 5. TSP1 limits tissue vascular response following radiation. Age and sex matched wild type and TSP1-null mice received 25 Gy to the right hind limb. Eight weeks later limb perfusion was assessed via BOLD MRI (FIG. 5A). Images were obtained for 30 minutes from $T_2$* weighted gradient echo sequences. DEA/NO (100 nmol/g body weight) was administered 5 minutes after starting the scan. The percent change in integrated BOLD values as a function of time is presented as mean±SE of eight pairs of wild type and TSP1-null mice respectively. Representative multislice multiecho, $T_2$ maps, and BOLD images show normal and irradiated hind limbs of WT and TSP1-null animals (FIG. 5B). In all images, the left limb irradiated (XRT).
Figure 5B:
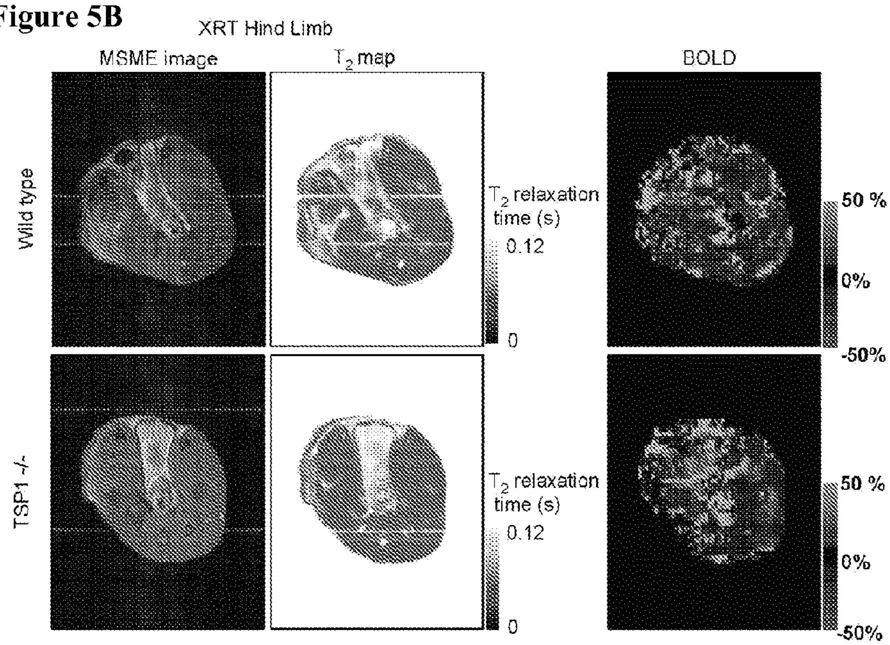

Two months after 25 Gy irradiation of the right hind limb, blood flow responses in both hind limbs were assessed using BOLD MRI following challenge with a rapidly releasing NO donor (1 μl/g animal weight of 100 mM DEA/NO, FIG. 5A). The irradiated hind limbs in wild type animals demonstrated an exaggerated overall increase in blood flow compared to the untreated hind limb. In contrast, the blood flow responses integrated over the irradiated and untreated hind limbs were essentially identical for the first 15 minutes in TSP1 null animals, demonstrating protection from the effects of radiation injury on vascular responsiveness. Multislice multiecho (MSME) and T2 weighted images confirmed significant tissue changes and injury in wild type irradiated hind limbs (FIG. 5B). These changes were markedly less in irradiated TSP1 null limbs.

Figure 6:
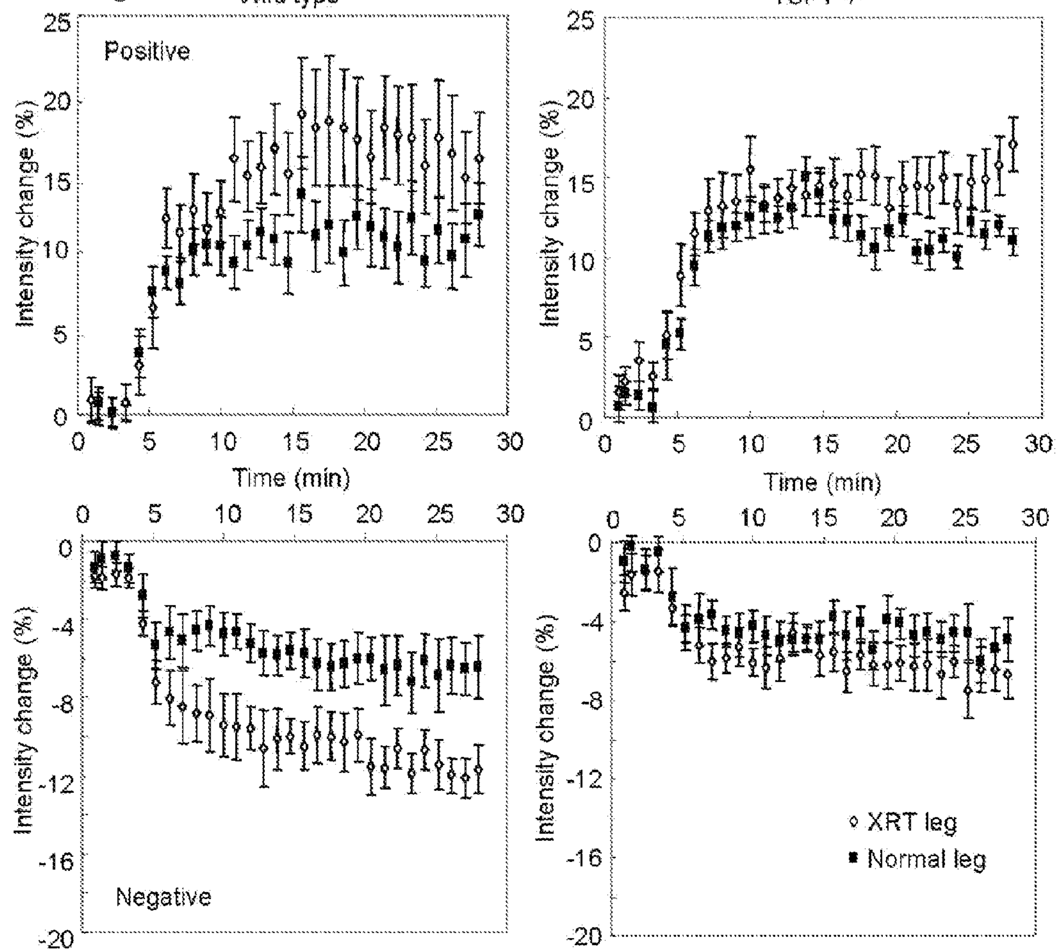
FIG. 6. The absence of TSP1 preserves blood oxygenation responses to NO in irradiated hind limbs. Positive (upper panels) and negative BOLD MRI signal curves (lower panels) are shown following NO treatment for irradiated (open symbols) and normal hind limbs (closed symbols) in age and sex matched wild type and TSP1-null eight weeks following 25 Gy to the right hind limb.

Analysis of areas in the hind limbs exhibiting positive and negative BOLD signals further emphasized the preservation of normal vascular responses in irradiated TSP1 null hind limbs (FIG. 6A, 6B). Areas with both positive and negative BOLD signals in irradiated limbs showed more exaggerated responses to NO than corresponding areas in control limbs of wild type mice. The corresponding areas in irradiated TSP1 null hind limbs resembled those of the untreated limb, confirming the preservation of normal vascular responsiveness despite radiation injury.

Figure 7:
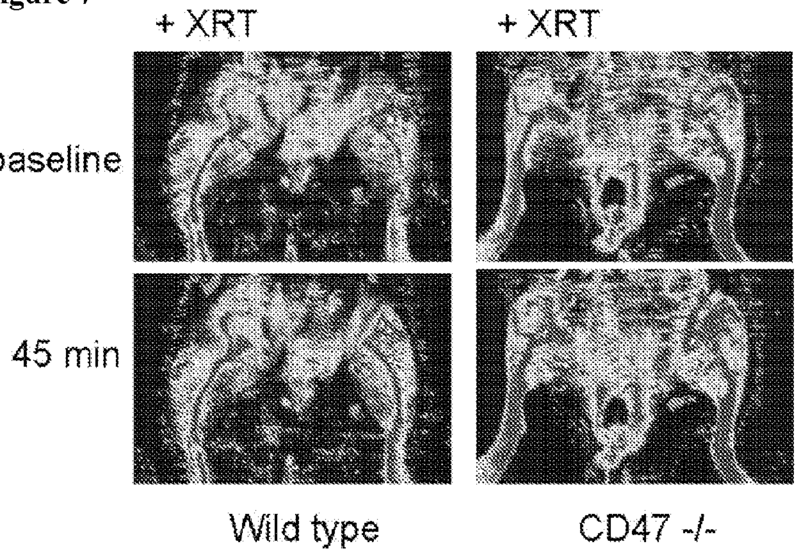
FIG. 7. TSP1 and CD47 modulate irradiated hind limb responses to vasoactive challenge. Age and sex matched C57B1/6 wild type, TSP1 and CD47 null mice received 25 Gy radiation to the right hind limb. Eight weeks following irradiation, limb perfusion was assessed by laser Doppler imaging following NO vasoactive challenge (1 μl/gram weight 100 mM DEA/NO stock via rectal bolus). Animals were maintained at a core temperature of 35.5° C. and 1.5% isoflurane anesthesia (FIG. 7A). Significance was determined using the independent two-sample t-test. *$P<0.05$ versus wild type. Cutaneous skin sections 1×2 cm in dimension were harvested from age and sex matched mice, stained for H & E, and vessels counted (FIG. 7B).
Figure 8A:
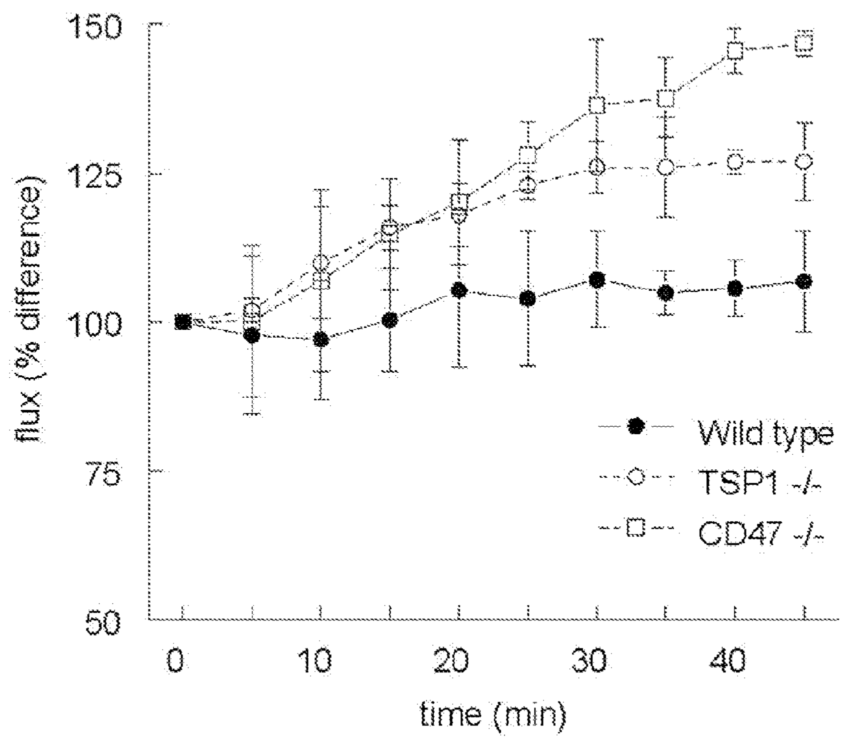
FIG. 8. TSP1 and CD47 modulate irradiated hind limb responses to vasoactive challenge. Age and sex matched C57B1/6 wild type, TSP1 and CD47 null mice received 25 Gy radiation to the right hind limb. Eight weeks following irradiation, limb perfusion was assessed by laser Doppler imaging for 45 minutes following NO vasoactive challenge (1 μl/gram weight 100 mM DEA/NO stock via rectal bolus). Animals were maintained at a core temperature of 35.5° C. and 1.5% isoflurane anesthesia (FIG. 8A). Cutaneous skin sections 1×2 cm in dimension were harvested from age- and sex-matched mice, stained for H&E, and vessels counted (FIG. 8B).

We further examined global vascular perfusion in irradiated hind limbs using laser Doppler imaging (FIG. 7). Two months following irradiation, perfusion responses were assessed over 45 minutes following administration of DEA/NO (1 μl/gram body weight of a 100 mM stock solution, FIG. 8A). Blood flow in the irradiated limb increased modestly in the irradiated limb of wild type mice, but significantly greater increases in response to vasoactive challenge were found in TSP1 and CD47 null mice.

Figure 8B:
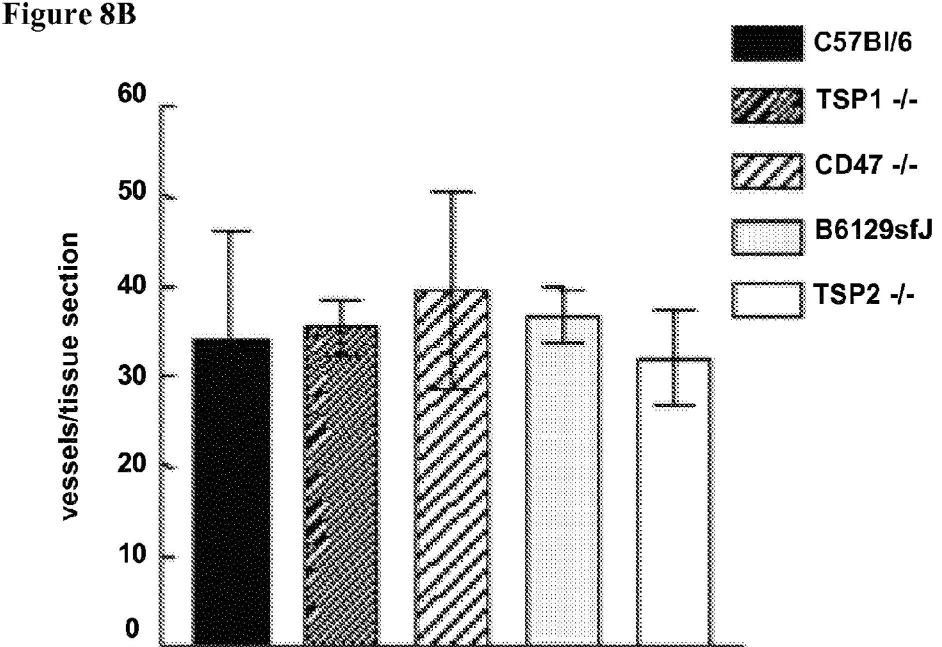

Tissue blood flow is dependent directly upon vascular density and increased vascularity could afford a protective advantage following tissue injury. Localized differences in organ vascularity have been reported between wild type and TSP1 or TSP2 null mice. Enhanced dermal vascularity was noted in TSP1 null pups compared to wild type (Crawford et al., *Cell* 93:1159-1170, 1998). However, similar aged pups showed no difference in retinal vascularity until stressed by hyperoxia-induced ischemia (Wang et al., *Dev Dyn* 228:630-642, 2003). In dermal wound healing, wild type and TSP1 null tissue sections demonstrated comparable vascularity (Bornstein et al., *Int. J. Biochem. Cell Biol.* 36:1115-1125, 2004), in contrast to TSP2 null tissue sections which showed enhanced vessel density. Furthermore, in contrast analysis of several visceral organs in wild type and TSP1 null mice failed to demonstrate significant vascular differences (Lawler et al., *J. Clin Invest.* 101:982-992, 1998). Quantification of vascular elements in cutaneous units from age and sex matched C57 BL/6 wild type, TSP1 and CD47 null and B6129sfJ and TSP2 null mice failed to document any significant difference in vessel count (FIG. 8B). Similarly, immunohistochemical analysis of $CD31^{+}$ vessels in paraffin-embedded hind limb demonstrated no significant differences between wild type, TSP1 null, and CD47 null mice.

Irradiated Hind Limbs in Null Mice Experience Minimal Apoptosis.

Figure 9:
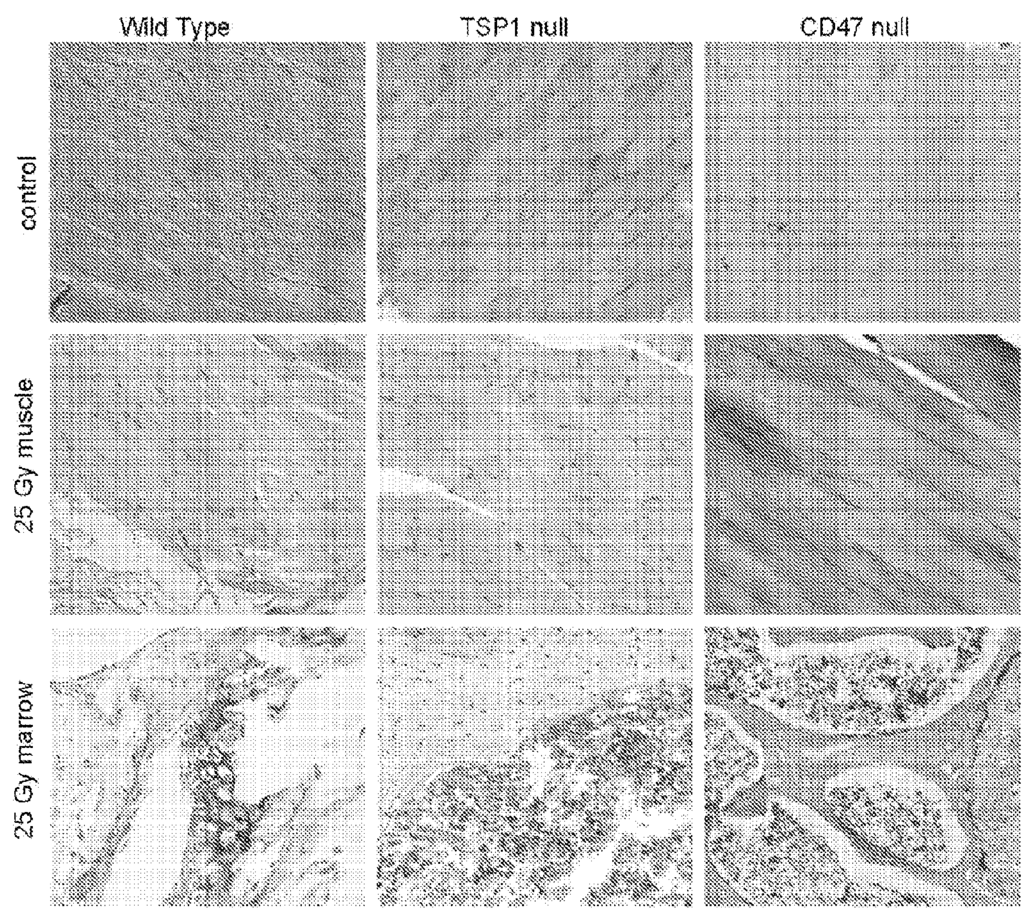
FIG. 9. Endogenous TSP1 and CD47 sensitize muscle and bone marrow to radiation-induced apoptosis. The presence of apoptosis within mouse hind limb tissue was examined by immunohistochemistry using a peroxidase in situ apoptosis detection kit. Non-irradiated control hind limbs (upper panels) and hind limbs irradiated for a total of 25 Gy from the indicated strains were prepared for paraffin-embedded tissue sections 12 hours post-radiation, and were examined for the presence of apoptotic nuclei. Apoptosis is inferred by intranuclear staining of muscle and bone marrow cells. Images were acquired using a 20× objective.

To assess the effects of TSP1 and CD47 on radiation-induced apoptosis in vivo, in situ staining of limb sections to detect DNA fragmentation was performed on age and sex matched wild type and null mice that received 25 Gy to the hind limb. Consistent with previous studies (Mazur et al., *Cell Biol Toxicol* 19:13-27, 2003), time course experiments in wild type animals demonstrated maximal tissue staining at 12 hours. In contrast, immunohistology of TSP1 and CD47 null limbs post-radiation demonstrated minimal to no evidence of apoptosis either in the skeletal musculature or the bone marrow (FIG. 9).

Endogenous TSP1 and CD47 Regulate Radiation-Induced Death of Vascular Cells in Vitro.

Improved hind limb survival in TSP1 and CD47 null mice could result from an intrinsic resistance of cells in the null tissue to irradiation or from a diminished inflammatory response in the nulls that permits better repair of the radiation injury. To differentiate these two hypotheses, we assessed the intrinsic radiation sensitivity of primary vascular cells cultured from each strain. Several studies have reported that vascular endothelial cells are highly radiosensitive and so may limit hind limb survival of irradiation (Rodemann & Blaesc, *Semin Radiat Oncol* 17:81-88, 2002).

Figure 10A:
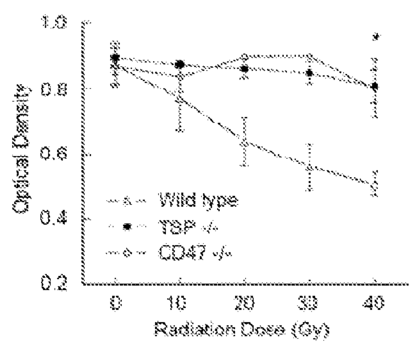
FIG. 10. TSP1 and CD47 limit vascular cell survival and proliferation following radiation. Primary vascular endothelial cells were harvested as previously described from wild type, TSP1 null, and CD47 null mice and plated in growth medium on 96-well culture plates ($5\times10^3$ cells/200 μl per well), treated with the indicated doses of radiation, and cell viability determined by MTT assay at 72 hours (FIG. 10A). Significance was determined using the independent two-sample t-test. *$P<0.05$ versus wild type. Lungs were obtained from 12 week old wild type, TSP1 and CD47 null mice and stained for H & E (FIG. 10B) Images obtained at ×100. Primary vascular endothelial cells were harvested from wild type and TSP2 null mice and plated in growth medium on 96-well culture plates ($5\times10^3$ cells/200 μl per well), treated with the indicated doses of radiation and cell viability determined by MTT assay following 72 hrs incubation (FIG. 10C). Primary murine wild type and TSP1 null vascular endothelial cells were seeded into 96 well plates at $5\times10^4$ cells/well density. After 24 hours cells were then either irradiated at 40 Gy or left to incubate at 37° C. as a control. At the indicated time points post-irradiation, proliferation was assessed by quantifying incorporation of bromodeoxyuridine (BrdU) into new synthesized DNA using a BrdU Cell Proliferation Assay (Calbiochem, La Jolla, Calif.) (FIG. 10D). Significance was determined using the one-way ANOVA test. *$P<0.05$ versus wild type. C57BL/6 wild type (FIG. 10E) and TSP1 null (FIG. 10F) 12-week old female mice were inoculated with B6F10 melanoma cells ($2.5\times10^6$ cells/animal) to the right lateral thigh. On tumors reaching 200 $mm^3$, half of each group underwent 10 Gy radiation to the tumor bearing limb. Tumor size was measured bi-weekly. Animals were sacrificed if tumors exceeded 2 $cm^3$. Results are from 16 animals, 8 of each strain.

Primary endothelial cells from lungs of wild type, TSP1, and CD47 null mice were irradiated, and mitochondrial viability was determined by MTT assay 72 hours following injury. Wild type cells demonstrated radiation dose-dependent cell death that resembled that of human cells (FIG. 10A). In contrast, doses up to 40 Gy failed to induce significant cell death in TSP1 and CD47 null cells.

Figure 10B:
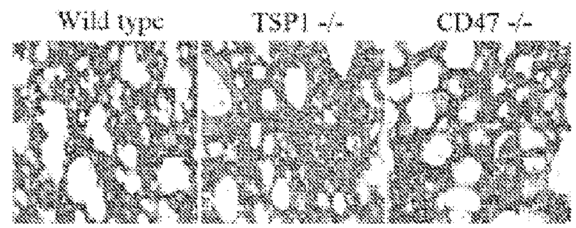
Figure 10C:
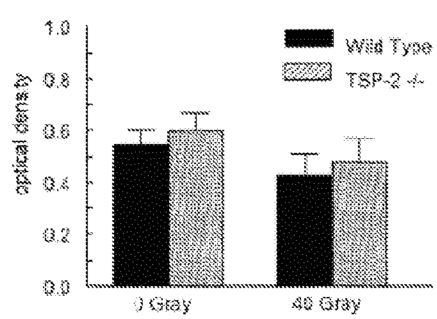

Chronic pulmonary inflammation has been reported in TSP1 null mice (Lawler et al., *J Clin Invest* 101:982-992, 1998) and the resulting inflammatory mediators could potentially alter the radiation sensitivity of endothelial cells harvested from this organ. However, the 12 week old sex matched mice used in the present study demonstrated no evidence of lung inflammation in any strain based on histologic analysis of H&E sections (FIG. 10B). Radioprotection in primary cells was specific for loss of TSP1 in that primary TSP2 null endothelial cells were not protected after irradiation (FIG. 10C).

TSP1 Limits Endothelial Cell Proliferation Post-Irradiation.

Figure 10D:
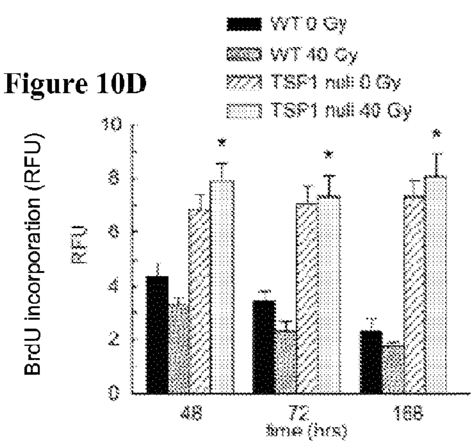

Although the above results show that ablation of TSP1 or CD47 permits cell survival following 40 Gy (ir)radiation, it was not clear that these cells maintain the ability to proliferate. To assess this, we examined cellular incorporation of bromodeoxyuridine (BrdU) into DNA. Consistent with their limited proliferative capacity in tissue culture, untreated wild type murine lung endothelial cells showed diminished BrdU uptake with time, and 40 Gy irradiation further diminished their DNA synthesis. As previously published, TSP1 null cells have an enhanced proliferative capacity (Isenberg et al., *Proc Natl Acad Sci USA* 102:13141-13146, 2005), but irradiation of these cells did not significantly decrease DNA synthesis over the 7 day time period studied (FIG. 10D). Therefore, in addition to promoting survival, the absence of TSP1 permits continued growth of irradiated vascular cells.

Absence of Endogenous TSP1 Does not Limit Tumor Response to Radiation.

Figure 10E:
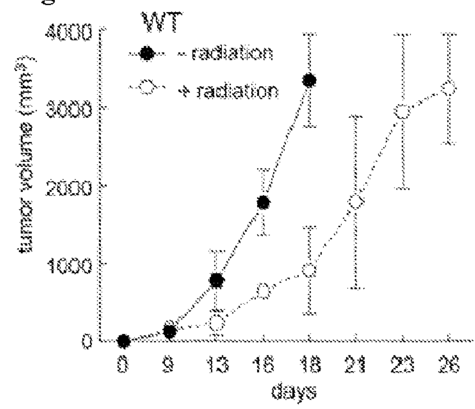
Figure 10F:
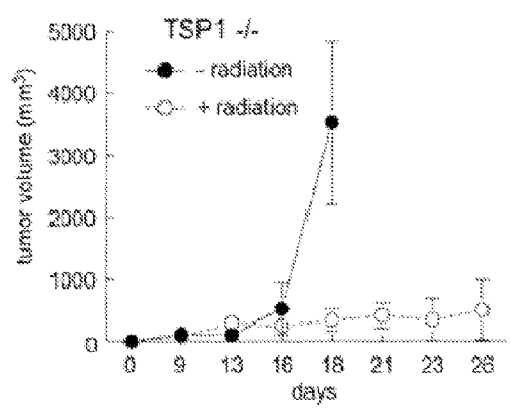

Expression of TSP1 by tumor cells is known to limit tumor angiogenesis and growth (Weinstat-Saslow et al., *Cancer Res.* 54:6504-6511, 1994), but not acute blood flow (Isenberg et al., *Neoplasia* 10:886-896, 2008. Conversely, host TSP1 expression can limit B16 tumor growth by inhibiting angiogenesis (Lawler et al., *Am. J. Pathol* 159:1949-1956, 2001). Because pretreatment with exogenous TSP1 enhanced the response of a human melanoma xenograft to radiation (Rofstad et al., *Cancer Res.* 63:4055-5061, 2003), we examined whether endogenous host TSP1 could similarly serve as a radiosensitizer. Syngenic B16F10 melanoma cells were implanted into the hind limbs of age and sex matched wild type and TSP1 null mice. B16 melanoma cells express very low levels of TSP1 mRNA, and TSP1 protein was reported to be below detectable levels (Culp et al., *Mol Cancer Res.* 5:1225-1231, 2007). When the tumors obtained a volume of 200 $mm^3$, half of the mice of each strain received 10 Gy radiation to the tumor bearing hind limb. Tumors in both wild type (FIG. 10E) and TSP1 null (FIG. 10F) animals demonstrated a significant growth delay following radiation. The delay was somewhat longer in the null, suggesting that therapies to protect normal tissue by blocking TSP1/CD47 signaling would not impair radiotherapy of the tumor. As demonstrated in Example 4, the increased growth delay in null, radioprotected animals is predictive of the growth delay observed in animals treated with a CD47 targeting morpholino prior to irradiation.

Discussion

Off target damage to non-cancerous tissues and vital organs remains one of the primary limitations for applying radiation therapy to treat cancer. One effort to enhance the therapeutic potential for radiotherapy while minimizing its complications has centered upon developing radioprotectants. We herein identify TSP1 and CD47 as limiting components of a cell-autonomous signaling pathway that controls tissue survival following high dose irradiation. The therapeutic potential of this pathway are substantial. Targeting this pathway may enhance the therapeutic window for radiotherapy of cancer by radioprotection of healthy tissue. Agents that block this radiosensitization pathway could also be valuable to limit the toxic effects of accidental radiation exposure.

Radiation-induced tissue damage and vascular dysregulation was evident in irradiated wild type and TSP2 null hind limbs, but minimal in irradiated TSP1 null and CD47 null hind limbs. Enhanced cell survival and proliferation correlated with tissue preservation at the gross and microscopic levels in both TSP1 and CD47 null animals, an advantage also not realized in irradiated TSP2 null mice. Tissue preservation translated into improved functional status 8 weeks post-irradiation. Functional benefits to the irradiated tissue beds included decreased hair loss, cutaneous desquamation and ulceration, tissue contracture, and ischemia. These long term benefits appear to result from an acute survival advantage of the null genotypes, because both tissue and bone marrow apoptosis were drastically reduced in the null mice within one day following the radiation injury. In the absence of TSP1/CD47 signaling, vascular cells cultured from the respective null mice showed enhanced cell survival and proliferative capacity following radiation injury, demonstrating that this acute radioprotection of vascular cells is cell-autonomous.

Damage to DNA is an immediate and universal effect of radiation. As expected, endogenous TSP1 does not prevent this immediate damage as assessed by similar loss of mitochondrial DNA in wild type and null irradiated tissue. DNA damage in turn initiates both cell repair pathways and cell death via p53-dependent and p53-independent mechanisms. Because TSP1 signaling via CD47 is known to induce caspase-independent type III cell death in leukocytes (Bras et al., *Mol Cell Biol* 27:7073-7088, 2007), the absence of TSP1 or CD47 may prevent radiation-induced cell death through a similar mechanism. This combined with enhancement of pro-survival NO/cGMP signaling could account for the cell-autonomous radioprotection of the null vascular cells.

The protection from radiation-induced damage in vivo, however, probably involves additional functions of TSP1 and CD47. CD47 is required for leukocyte recruitment (Lindberg et al., *Science* 274:795-798, 1996), and TSP1 is also known to stimulate T cell migration (Li et al. *J Cell Biol* 157:509-519, 2002). Therefore, TSP1 and CD47 null mice also may benefit from decreased leukocyte recruitment during the acute response to radiation injury. Moreover, as suggested in Example 5, radioprotection conferred by blocking the TSP1/CD47 interaction is largely independent of NO/cGMP signaling.

Endothelial cells are exquisitely sensitive to radiation induced cell death through the induction of several mediators of apoptosis (Rodemann & Blaese, *Semin Radiat Oncol* 17:81-88, 2002). Within 24 hours of irradiation, damaged capillaries demonstrate leukocyte attachment, endothelial cell swelling, thrombosis with complete loss of capillary networks, and secondary ischemia. Even vessels that remain patent undergo long term thickening of the basement membrane and soft tissue scarring. This late effect is driven by activation of fibroblasts by radiation through the terminal differentiation of progenitor cells into post-mitotic fibrocytes and elevated production of collagen by the same (Rodemann & Blaese, *Semin Radiat Oncol* 17:81-88, 2002; Brush et al., *Semin Radiat Oncol* 17:121-130, 2007). These processes depend on TGFβ, and TSP1 is a mediator of latent TGFβ activation (Murphy-Ullrich & Poczatek, *Cytokine Growth Factor Rev* 11:59-69, 2000) and TGFβ-dependent fibrosis (Belmadani et al., *Am J Pathol* 171:777-789, 2007). Deletion of Smad3 in mice is protective for radiation-induced fibrosis by blocking TGFβ signaling (Flanders et al., *Am J Pathol* 160:1057-1068, 2002). Thus, TSP1 null mice may be partially protected from the long term fibrotic response to radiation, but this does not explain the immediate protection of the TSP1 null, and we would not expect CD47 null mice to share this TGFβ-dependent benefit.

Although TSP1 and CD47 null endothelial cells and mice show a dramatic resistance to radiation, TSP2 null cells and mice showed no significant protection against radiation-induced cell death or tissue damage. This was surprising because TSP1 and TSP2 share a number of cellular receptors, and both are potent angiogenesis inhibitors. TSP2 was inferred to interact with CD47 based on conservation of a CD47-binding peptide sequence identified in TSP1 and a shared immune phenotype of TSP1 and TSP2 null mice (Gao et al., *J Biol Chem* 271:21-24, 1996; Lamy et al., *J Immunol* 178:5930-5939, 2007). However, uncertainties concerning structural basis for TSP1-CD47 interaction raise questions about whether TSP2 also interacts with this receptor (Carlson et al., *Cell Mol Life Sci* 65:672-686, 2008). Lack of radioprotection in the TSP2 null could arise either from lack of TSP2 binding to CD47 or lack of significant TSP2 expression at an appropriate time following radiation injury.

Deletion of several other genes in transgenic mice has been associated with increased (Nos1, Smad3, Chk2, p. 53) or decreased (cKit, p53) radioresistance of bone marrow or intestinal crypt cells to whole body irradiation or to irradiation of cells in vitro (Epperly et al., *Exp Hematol* 235:137-145, 2007; Komarova et al., *Oncogene* 23:3265-3271, 2004; Epperly et al., *Radiat Res* 165:671-677, 2006; Takai et al., *Embo J* 21:5195-5205, 2002). However, less attention has been given to identifying genes that modulate the radiosensitivity of skin and other soft tissues that can be dose-limiting for radiotherapy of tumors and complicate post-irradiation reconstructive surgery.

Thbs1 or CD47 deletion dramatically improves hind limb resistance to high dose irradiation and vascular cell survival of irradiation in vitro. This suggests that strategies to prevent TSP1/CD47 interaction or to suppress expression of either protein can enhance the radioresistance of soft tissues. Our studies in TSP1 null mice suggest that tumors in these mice retain their sensitivity to radiation. Therefore, TSP1/CD47 antagonists may have selective radioprotective activity for normal tissues.

Example 2

In Vitro Characterization of Radioprotectant Agents

This example describes a series of experiments characterizing the radioprotective activities of agents that inhibit the interaction of thrombospondin-1 (TSP1) and CD47, using in vitro, cell-based assays.

Methods

Unless otherwise noted, methods are as described above.

Reagents and cells. Human umbilical vein endothelial cells (HUVEC) were cultured in endothelial basal medium supplemented with the manufacturer's additives and 2% fetal calf serum (FCS) in 5% $CO_2$ at 37° C. (Lonza, Switzerland). A CD47 targeting morpholino oligonucleotide (SEQ ID NO: 4) and mismatched control morpholino SEQ ID NO: 5, and a CD36 targeting morpholino (SEQ ID NO: 16) and a 4 base mismatched control were purchased from GeneTools, LLC (Philomath, Oreg.). The CD47 targeting morpholino blocks translation of both murine and human CD47 mRNAs. Mouse monoclonal antibodies recognizing human CD47 (B6H12) and murine or human TSPI (A6.1) were purchased from Abeam (Cambridge, Mass.). The TSP1-derived CD47 binding peptide FIRVVMYEGKK (7N3) (SEQ ID NO: 2) was synthesized by Peptides International (Louisville, Ky.). A control peptide FIRGGMYEGKK (604) SEQ ID NO: 3) was synthesized by the late Dr. Henry Krutzsch (NCI, NIH) (Barazi et al., *J. Biol Chem* 277:42859-42866, 2002).

Cell Viability Assay. HUVEC were plated at a density of 5000 cells/well in 96 well plates (Nunc), and were treated 24 hours later with either the indicated doses of a CD47 antibody (B6H12), a TSP1 antibody (A6.1), the CD47-binding peptide 7N3, or control peptide 604. One hour later the cells were exposed to a single dose of gamma radiation (0, 10, 20, 30, and 40 Gy) and allowed to incubate another 72 hours at 37° C. Experiments done with B16E10 melanoma cells in Example 4 were done in a similar manner treating either 1 hour prior to a single dose of radiation (10 Gy) with peptide 7N3 or 48 hours prior with CD47 morpholino. Cell viability was determined using the CellTiter 96 Aqueous One Solution cell proliferation assay (Promega, Madison, Wis.) as per the manufacturer's instructions and absorbance at 490 nm was determined using an MR580 Microelisa AutoReader (Dynatech, Alexandria, Va.). The same assay was performed on HUVEC using either the CD47 or CD36 morpholino, but 48 hours were allowed to pass prior to radiation (0 or 40 Gy) to allow for suppression of the target proteins. Similarly, control experiments were performed using the nitric oxide synthase (NOS) inhibitor L-NAME, a membrane permeable cGMP analogue, 8-Bromo cGMP, or the NO donor DETA/NO.

Results

Radioprotection of Human Endothelial Cells by Targeting TSP1 or CD47.

Figure 11A:
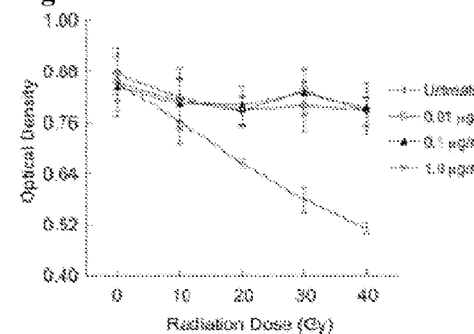
FIG. 11. Radioprotective activities of TSP1 and CD47 antibodies, a CD47 binding peptide from TSP1, and a CD47 morpholino. HUVEC were plated on 96-well plates in standard growth medium. Cells were treated with TSP1 (FIG. 11A) or CD47 (FIG. 11B) monoclonal antibodies (clone A6.1 or B6H12, respectively) and received the indicated doses of radiation 24 hours after addition of the antibodies. Cell (mitochondrial) viability was measured 48 hours post irradiation using an MTT assay. Cells were treated using peptide 7N3 (FIG. 11C) and control peptide 604 (FIG. 11D), subjected to the same experimental conditions, and assayed via MTT. Knockdown of CD47 by pretreatment for 48 hours using a specific morpholino granted protection against cell death after a radiation dose of 10 Gy when compared to control groups (non-treated, mismatched morpholino, and endoporter vehicle control) (FIG. 11E; *p<0.05, #p<0.01) using the MTT assay to determine HUVEC viability post radiation (40 Gy). Cells treated with a CD36 morpholino (FIG. 11F) under the same conditions demonstrated no radioprotection. Experiments were repeated 3 times and results presented as the mean±SD.
Figure 11B:
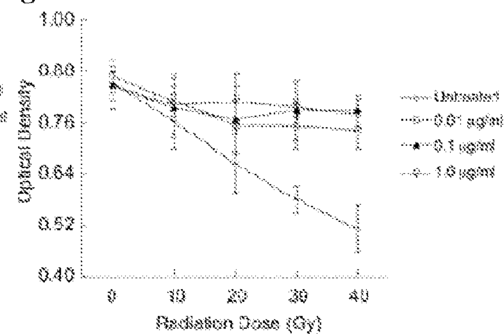
Figure 11C:
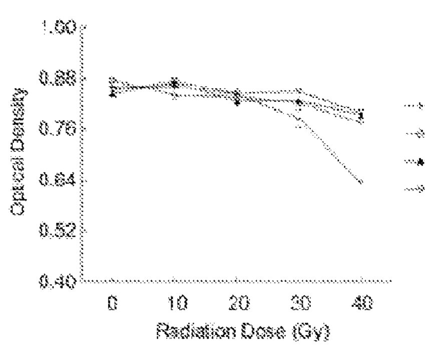
Figure 11D:
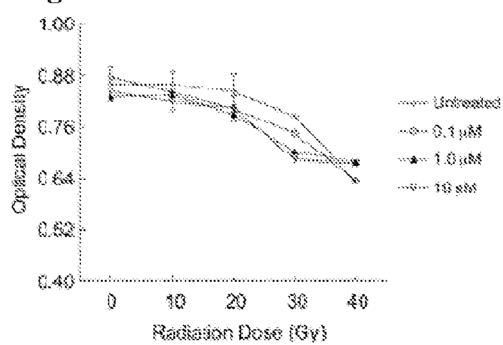
Figure 11E:
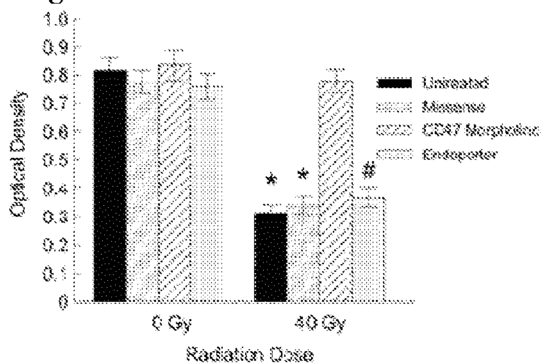
Figure 11F:
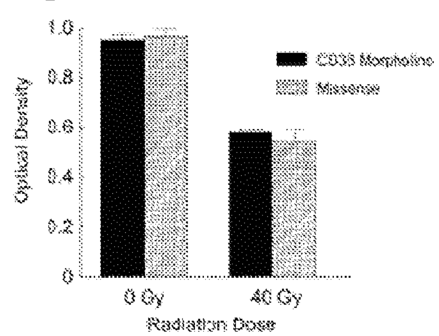

As disclosed above, hind limbs of TSP1 and CD47 null animals are resistant to tissue damage from high dose radiation. Vascular cells in culture from the null mice are also profoundly radioresistant, demonstrating that this effect is cell autonomous. Thus, it was investigated whether therapeutic targeting of TSP1 or CD47 could confer protection from ionizing radiation (IR) using human vascular cells that express both TSP1 and CD47. HUVEC treated with an antibody to TSP1 (clone A6.1) or its receptor CD47 (clone B6H12) provided dramatic protection in HUVEC, with treated cells displaying preservation of mitochondrial function at up to 40 Gy (FIGS. 11A, B). A CD47 binding peptide (7N3) was less efficacious (FIG. 11C) but at higher radiation doses still enhanced cell survival post-irradiation relative to the control peptide 604 (FIG. 11 D). Previous reports had shown that suppression of CD47 alone in cells and tissues is sufficient to enhance physiologic NO signaling and confer tissue protection to ischemia (Isenberg et al., *Ann Surg* 247: 180-190, 2008), Similarly, an antisense CD47 morpholino rendered HUVEC resistant to radiation-driven cell death when compared to untreated, missense and endoporter controls (FIG. 11E, $P<0.05$). This radioprotective effect is specific to TSP1 since HUVEC that were treated with an antisense morpholino specific for the TSP1 receptor CD36 showed a decrease in cellular viability similar to that of untreated cells and cells treated with the corresponding mismatched control morpholino (FIG. 11F).

Peptides 7N3 and C6d Convey Radioprotection to HUVEC in Culture

Figure 12A:
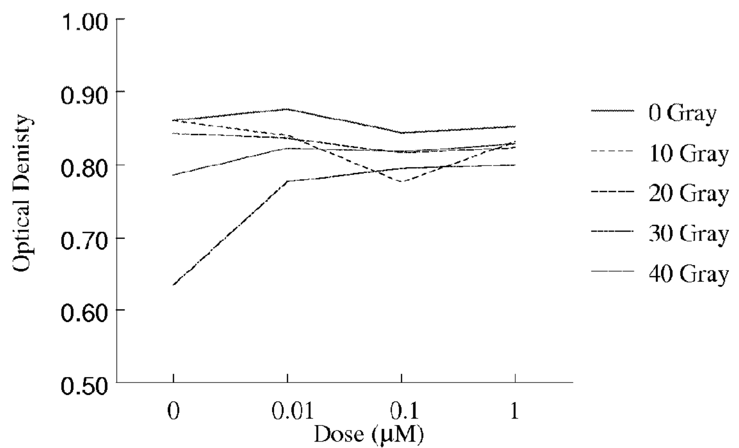
FIG. 12. Peptides 7N3 and C6d are radioprotective to HUVEC in culture. Human umbilical vein endothelial cells (HUVEC) grown in EGM medium in 96-well plates were treated with graded doses of a peptide agent, as indicated. One hour later, cells were exposed to a single dose of gamma radiation (0, 10, 20, 30, and 40 Gray) and allowed to incubate 72 hours at 37° C. Cell viability was determined with the CellTiter 96 AQueous One Solution Cell Proliferation Assay. A protective effect against increasing doses of radiation can be seen with both 7N3 (FIG. 12A) as well as C6d (FIG. 12B) peptides when compared to virtually no protection provided by the control peptide 604 (FIG. 12C).
Figure 12B:
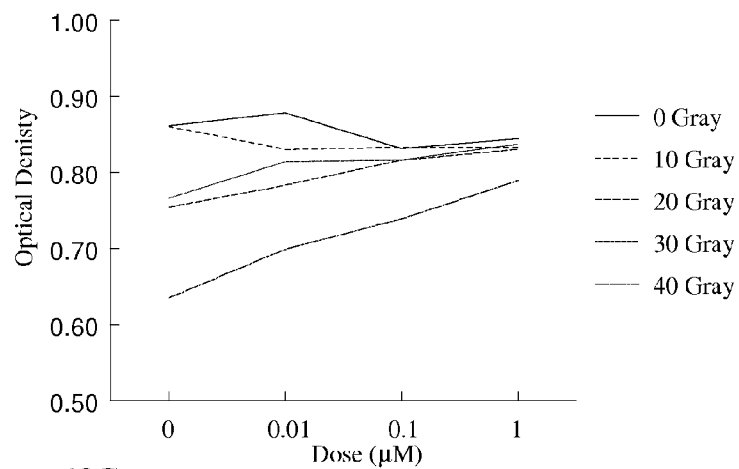
Figure 12C:
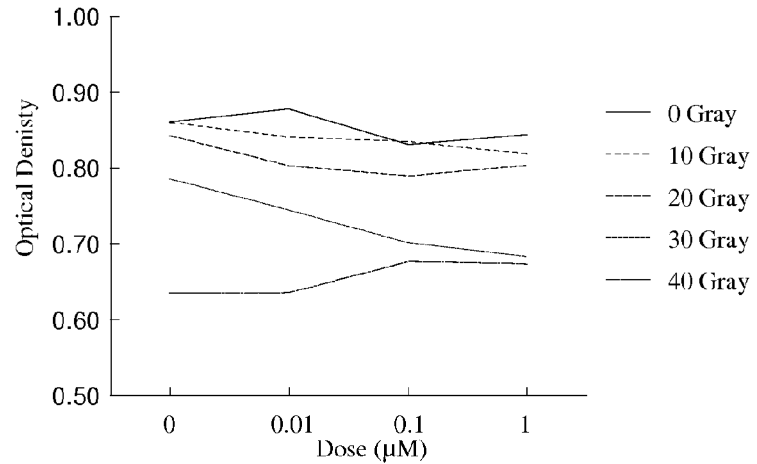

In an additional experiment to test the effect of radioprotective peptides, human umbilical vein endothelial cells (HUVEC) grown in EGM medium in 96-well plates were treated with graded doses of a peptide agent, as indicated. One hour later, cells were exposed to a single dose of gamma radiation (0, 10, 20, 30, and 40 Gray) and allowed to incubate 72 hours at 37° C. Cell viability was determined with the CellTiter 96 AQueous One Solution Cell Proliferation Assay. A protective effect against increasing doses of radiation can be seen with both 7N3 (FIG. 12A) as well as C6d (FIG. 12B) peptides when compared to virtually no protection provided by the control peptide 604 (FIG. 12C).

Peptide 7N3 is Radioprotective to HAVSMC in Culture

Figure 13:
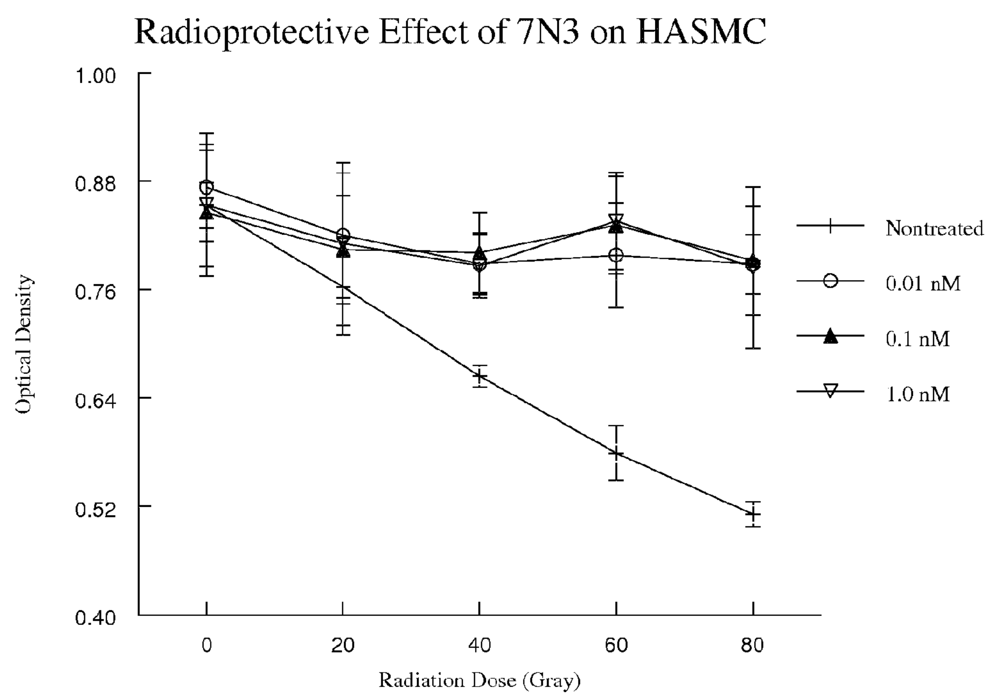
FIG. 13. Peptide 7N3 is radioprotective to HAVSMC in culture. Human aortic vascular smooth muscle cells (HAVSMC) were also subjected to the CellTiter 96 Aqueous One Solution cell proliferation assay (Promega, Madison, Wis.). HAVSMC have been shown to be more radioresistant therefore greater doses of radiation were used in this assay. Again, the peptide 7N3 showed a profound radioprotective protective effect even at very high doses of radiation.

Human aortic smooth muscle cells (HAVSMC) were also subjected to the same cell viability assay as above. HAVSMC have been shown to be more radioresistant therefore greater doses of radiation were used in this assay. Again, the peptide 7N3 showed a profound radioprotective protective effect even at very high doses of radiation (FIG. 13).

Figure 14A:
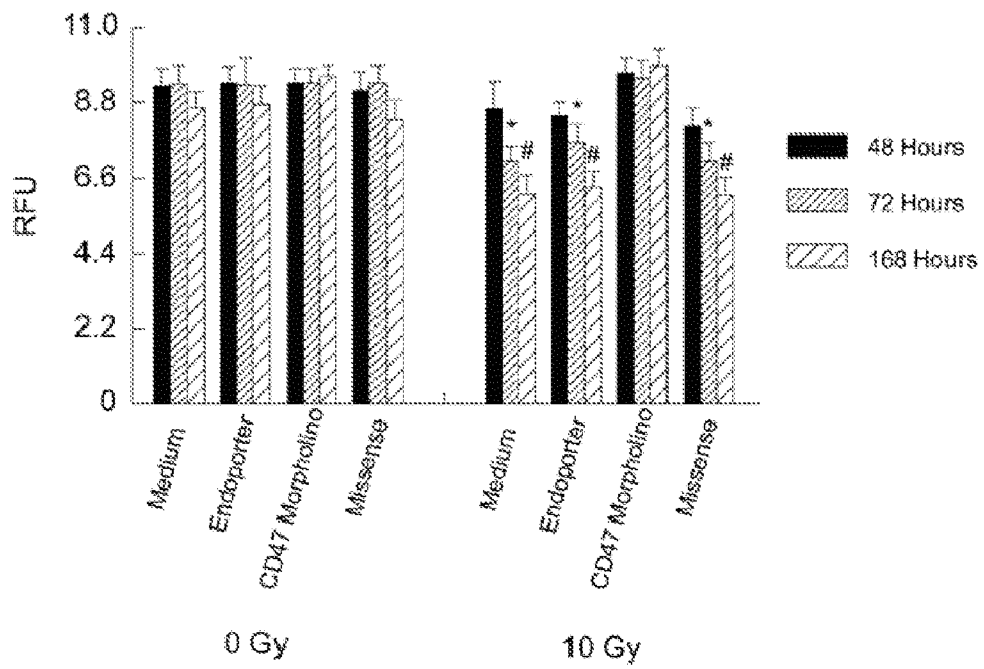
FIG. 14. TSP1 and CD47 antibodies or antisense suppression of CD47 maintain proliferation of irradiated HUVEC. HUVEC were plated in 96-well plates in growth medium and treated with CD47 morpholino (FIG. 14A; *p<0.05, #p<0.01) TSP1, or CD47 antibodies (FIG. 14B; *p<0.05, #p<0.01) and exposed to 10 Gy irradiation 48 hours later. Cell proliferation at the indicated times post-radiation was determined by intracellular BrdU incorporation. Experiments were repeated 3 times, and results presented as the mean±SD.
Figure 14B:
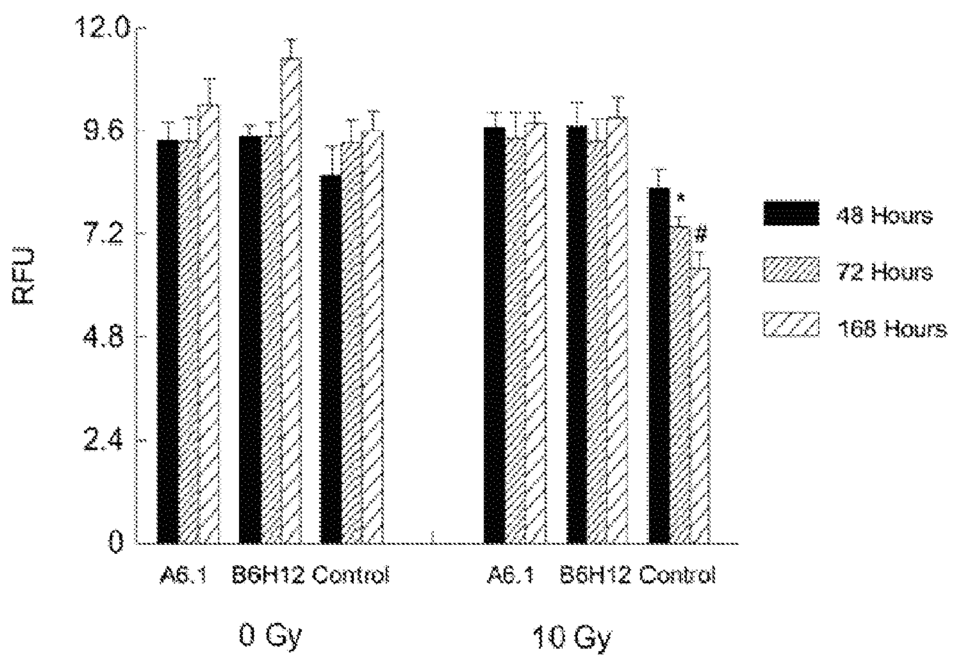

TSP1/CD47 Inhibition Maintains Proliferative Capacity in Irradiated Endothelial Cells Tissue health requires the ability to repair and replace damaged structures through cell proliferation. Proliferative capacities are typically lost in normal tissues following radiation injury. We therefore determined whether therapeutic targeting of TSP1/CD47 preserved the proliferative capabilities of human vascular cells. DNA synthesis in untreated cells progressively decreased over 1 week following irradiation (FIG. 14A). Pretreatment using a CD47 morpholino, but not with vehicle or a mismatched control morpholino, maintained proliferation in cells exposed to 10 Gy of radiation over the same time period (FIG. 14A, $P<0.05$). However, this is not seen after treatment with a CD36 morpholino, demonstrating that this effect is CD47-specific. Enhanced DNA synthesis was also seen under the same conditions using antibodies against either TSPI or CD47 (FIG. 14B, $P<0.05$).

Proliferative capacities were also determined in endothelial cells exposed to high doses of radiation of 40 Gy. HUVEC were seeded into 96 well plates for 24 hours at 37° C., then treated with either antibody A6.1 or B6H12 or peptide 7N3. The treated cells were irradiated at 40 Gy 1 hour later. Control and irradiated plates were assayed for BrdU uptake over 96 hours post-radiation. The assay was performed according to the manufacturer's protocol, and the plates were read at 420 nm.

Figure 15:
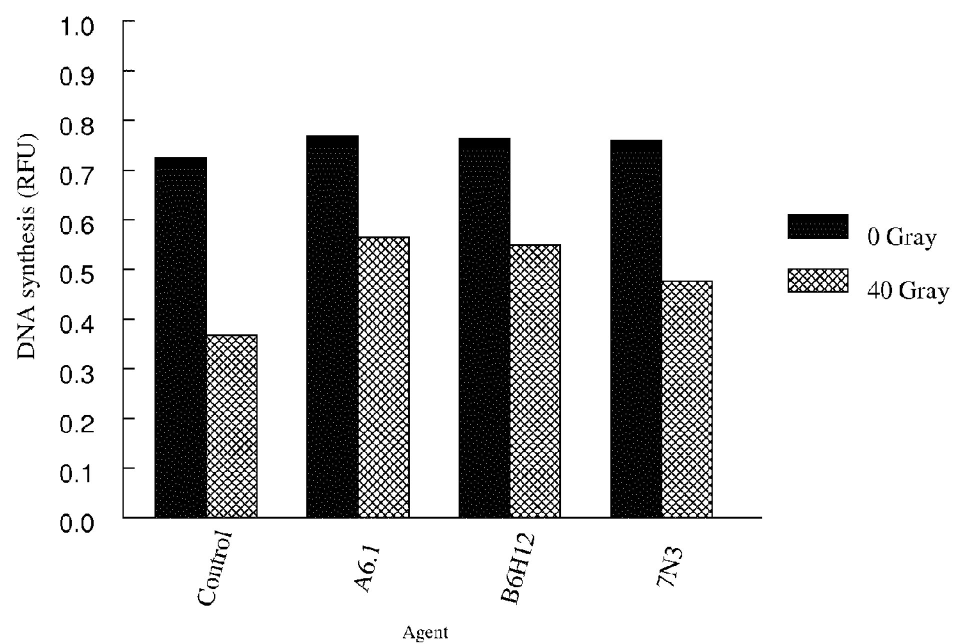
FIG. 15. HUVEC protected by radioprotective agents are both viable and proliferate at a better rate than untreated cells in culture. Proliferation was assessed by quantifying incorporation of bromodeoxyuridine (BrdU) into newly synthesized DNA using a BrdU Cell Proliferation Assay. HUVEC were seeded into 96 well plates for 24 hours at 37° C., then treated with either antibody A6.1 or B6H12 or peptide 7N3. The treated cells were irradiated at 40 Gy 1 hour later. Control and irradiated plates were assayed for BrdU uptake over 96 hours post-radiation. The assay was performed according to the manufacturer's protocol, and the plates were read at 420 nm.

Consistent with their limited viability post-radiation in tissue culture, untreated HUVEC showed diminished BrdU uptake with time, and 40 Gy irradiation further diminished their DNA synthesis (FIG. 15). In contrast, TSP1-CD47 targeting therapies conferred enhanced proliferative capacity to primary vascular cells post-radiation (FIG. 15). These results show that not only are the treated cells viable but proliferating at a better rate than untreated cells. Taken together, the results of the cellular proliferation assays were consistent with the observations described in Example 1 that primary murine TSP1 and CD47-null vascular cells maintain their proliferative capacity even after high doses of irradiation (40 Gy).

Example 3

In Vivo Characterization of Radioprotectant Agents

This example describes characterization of the radioprotective in vivo activities of agents that inhibit the interaction of thrombospondin-1 (TSP1) and CD47. These results demonstrate that temporary suppression of CD47 expression can protect normal tissues from damage by IR. This protection is observed in skin, muscle, and bone marrow of irradiated mouse hindlimbs. Tissue radioprotection following CD47 suppression is at least partially a cell-autonomous response based on the increased radioresistance of TSP1 null and CD47 null vascular cells in vitro (see Example 1) and the ability of CD47 antisense suppression, blocking peptides, and antibodies to induce similar radioresistance in wild type vascular cells in vitro (see Example 2).

Methods

Unless otherwise noted, methods are as described above.

Animals: Wild type C57BL/6 or C3H mice were housed and fed as described above.

Irradiation of mice: Age and sex matched wild type mice underwent local irradiation to the right hindlimb as described in Example 1. Forty-eight hours prior to irradiation, animals received the CD47 morpholino (SEQ ID NO: 4), a control morpholino (SEQ ID NO: 5) (both at 10 μM in 7500 μl PBS via intramuscular injection), vehicle, or no treatment to the hind limb. Under 1% isoflurane inhalation anesthesia, the animals were placed in customized Lucite jigs that allow for immobilization and selective irradiation of the right hindlimb. A single radiation dose of 25 Gy was delivered by a Therapax® DXT300 X-ray irradiator (Pantak, Inc., East Haven, Conn.) using 2.0-mm A1 filtration (300 kVp) at a dose rate of 2.53 Gy/min. Care was taken to avoid irradiation of other body parts by using lead shields specifically designed as a part of the jigs. After irradiation, the animals were placed in cages as indicated above and observed weekly. Skin reaction after hind limb irradiation was quantified every week after treatment for 8 weeks using a previously described grading system (Flanders et al., *Am J. Pathol* 163:2247-2257, 2003). Briefly, tissue necrosis grading system consists of 5 categories: normal, hair loss, erythema, dry desquamation, and moist desquamation/ulceration.

Laser Doppler Analysis: Hind limb blood flow was measured using laser Doppler imaging as described above. Animals received 25 Gy to right and left hind limbs. The right limb also received 500 μl of sterile PBS+10 μM CD47 morpholino via intramuscular injection 48 hours prior to radiation. Analysis of hind limb blood flow to vasoactive challenge was performed 8 weeks after treatment and radiation. Studies were performed under 1.5% isoflurane inhalation anesthesia and a core temperature of 36.5° C. The parameters of the scan area; 1.6×2.5 cm, scan speed; 4 ms per pixel, scan time; 1 minute 54 sec, override distance; 20 cm. After obtaining baseline analysis of limb blood flow, an NO challenge (10 μM DEA/NO, 100 nmol/g bodyweight) was administered via intra-rectal installation and flow analysis repeated.

Immunohistochemical Evaluation: Staining for the macrophage marker CD68 was done as previously described (Manso et al., *Cancer Res* 68:7090-7099, 2008) utilizing a rat anti-mouse CD68 antibody (AbD Serotec, Raleigh, N.C.). H&E staining of tissue hind limbs was prepared by American HistoLabs, Gaithersburg, Md.

Results

Tissue Protection from Radiation Injury by Antisense CD47 Suppression

Figure 16A:
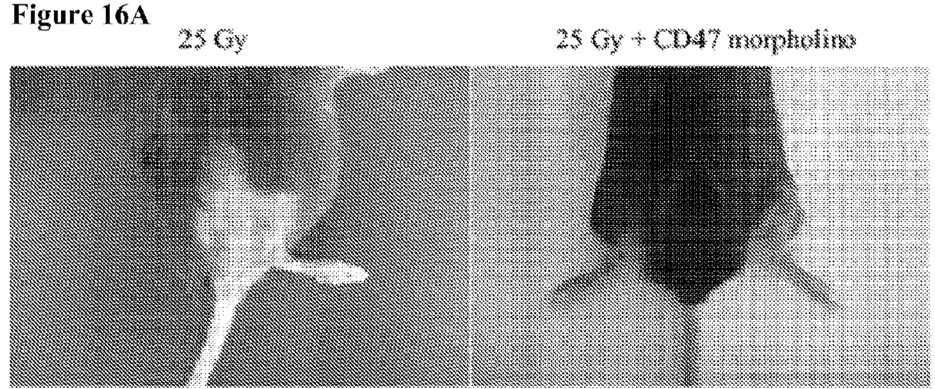
FIG. 16. CD47 suppression using an antisense morpholino minimizes tissue damage from radiation injury. Age and sex matched C57BL16 wild type mice underwent a one-time treatment of the right hindlimb with either a murine specific CD47 morpholino oligonucleotide (10 μM in 750 μl PBS) or 750 μl of PBS injected local-regionally to the muscle and soft tissues. Forty-eight hours later animals received 25 Gy irradiation to the treated hindlimb, and the animals were observed for a period of 8 weeks. At the end of 8 weeks, there was a considerable amount of alopecia, dry desquamation and early signs of fibrotic contractures within the irradiated hind limbs of mice receiving only PBS. In contrast, the mice receiving treatment with CD47 morpholino showed little to no alopecia, ulceration, or desquamation at the end of eight weeks (FIG. 16A). The tissue necrosis grading scores for 8 animals are presented as mean±SD (FIG. 16B) and show a similar trend throughout the 8-week observation period.
Figure 16B:
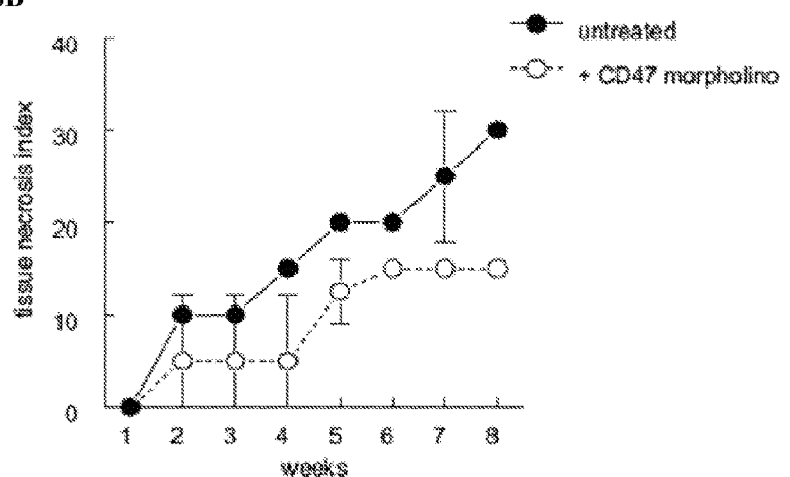

Age and sex matched C57BL16 wild type mice underwent a one-time treatment of the right hindlimb with the CD47 antisense morpholino oligonucleotide (10 μM in 750 μl PBS), a mismatched control morpholino, or vehicle (PBS) injected local-regionally to the muscle and soft tissues. Forty-eight hours later the animals received 25 Gy irradiation to the treated hindlimb and were observed for 8 weeks. At the end of 8 weeks, significant alopecia, dry and wet desquamation, and tissue ulceration with fibrous contracture of radiated hindlimbs was noted in mice pre-treated with the control morpholino or vehicle. In contrast, mice receiving the CD47 targeting morpholino showed minimal to no alopecia, ulceration, and desquamation at the end of 8 weeks (FIGS. 16A and B). These hindlimbs also showed minimal contracture due to fibrosis and remained flexible and supple.

Figure 17:
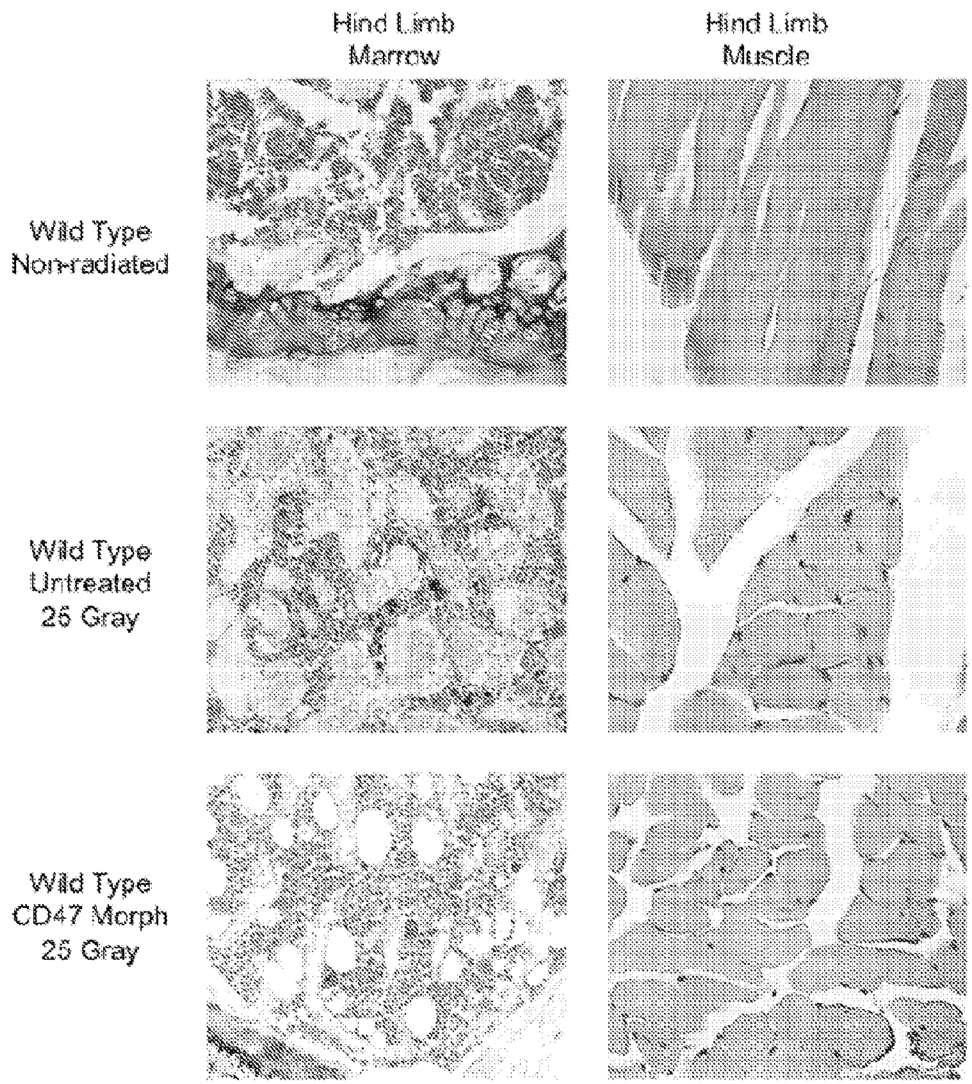
FIG. 17. Therapeutic suppression of CD47 prevents radiation-induced apoptosis in muscle and bone marrow. The presence of apoptosis was detected by the TUNEL method as brown nuclear staining. Non-irradiated control hindlimbs (upper panels) and hindlimbs irradiated for a total of 25 Gy all from age and sex matched C57BL/6 wild type mice were prepared for paraffin-embedded tissue sections 24 hours post-radiation and were examined for the presence of apoptotic nuclei. Mice hindlimbs injected with the CD47 morpholino (bottom panels) 48 hours prior to radiation were also prepared in the same manner 24 hours post-radiation. Apoptosis is inferred by intranuclear staining of muscle and bone marrow cells. Images were acquired using a 20× objective.

Decreased Apoptosis in Irradiated Bone Marrow and Skeletal Muscle Through CD47 Suppression Immunohistological analysis of programmed cell death via TUNEL labeling of irradiated hindlimbs from treated and control hindlimbs demonstrated minimum cell death (apoptosis) in the skeletal muscle of limbs that received the CD47 morpholino (FIG. 17). Although bone marrow cells are among the most sensitive to radiation-induced death, tissue protection extended to the bone marrow compartment. Routine H&E results of treated hindlimb skeletal muscle were comparable to results obtained in hindlimbs from CD47 null mice (see Example 1) with muscle cell survival and hypertrophy (results not shown). Control irradiated hindlimbs showed significant apoptosis in bone marrow and skeletal muscle cells.

Targeting CD47 Blocks Radiation-Induced Vasculopathy

Figure 18A:
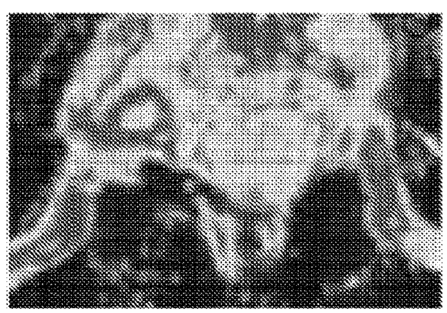
FIG. 18. Targeting CD47 Protects Composite Tissue From Radiation-Induced Vascular Damage. Age matched male C57BL/6 mice received 25 Gy to both hind limbs. Forty-eight hours prior to irradiation the right hind limb was treated by direct intra-muscular injection with the CD47 morpholino (750 μl at 10 μM concentration). The opposite (control) limb received nothing. Eight weeks post-radiation hind limb blood flow changes to a nitric oxide (NO) challenge (DEA/NO 100 nmol/g body weight via rectal instillation) was assessed via Laser Doppler imaging (FIG. 18A). In other experiments, the opposite (control) limb received injection of either missense oligonucleotide or sterile PBS with similar results (not shown). Laser Doppler was performed under 1.5% isoflurane inhalation anesthesia with animal core temperature held constant at 36.5° C. Results in the lower panel represent the mean±SD of 6 mice in each treatment group (FIG. 18B).
Figure 18A:
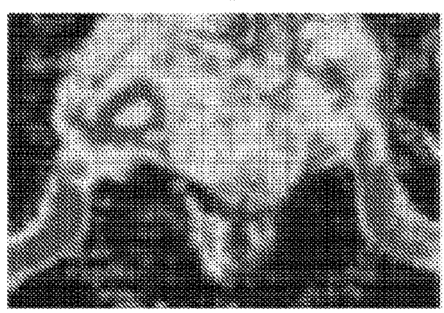
Figure 18B:
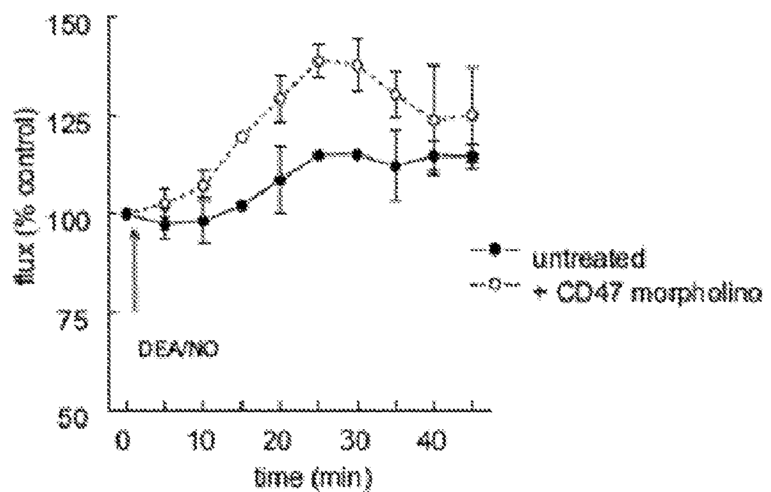

The vasculature, and in particular vascular endothelial cells, are very sensitive to radiation (Mouthon et al., *Radiat Res* 160:593-599, 2003; Milliat et al., *Am J. Pathol* 169:1484-1495, 2006; Garcia et al., *Science* 300:1155-1159, 2003). Following injury, vascular networks undergo a progressive fibrous obliteration, resulting in a loss of perfusion, ischemia, and tissue necrosis. Irradiated hindlimbs treated with the CD47 suppressing morpholino showed enhanced vascular perfusion in response to a DEA/NO challenge on laser Doppler 8 weeks post-injury (FIG. 18). In contrast, control irradiated hindlimbs demonstrated a substantial perfusion defect.

Example 4

TSP/CD47 Targeting is not Radioprotective for Cancer Cells in vitro and Increases Tumor Ablation in vivo This example describes the effects of TSP/CD47 targeting on an in vitro cancer cell line. Also described is the observation that tumor ablation is increased following CD47 knockdown in a subject undergoing radiotherapy. Although suppression of CD47 also confers a modest radioprotection to B16 melanoma cells in vitro, such radioprotection does not occur for B16 tumors in vivo. Rather, as described herein, suppression of CD47 dramatically enhances ablation of B16 melanoma and squamous cell carcinoma cells in tumor-bearing mice.

Methods

Unless otherwise noted, methods are as described above.

Tumor Establishment and Irradiation. C57 B16 mice were injected in the right hindlimb with $1\times10^6$ B16F10 melanoma cells, and tumors were allowed to establish for 1 week. After tumor incorporation, the hind limbs were treated with either the CD47 morpholino or sterile phosphate buffered saline (PBS). Forty-eight hours later, all mice were subjected to right hind limb irradiation (10 Gy). The mice were observed and tumor size determined twice a week by the same individual until lesion size necessitated animal euthanasia.

In other experiments, C3H mice were injected in the right hindlimb with either $1.5\times10^5$ SCC VII cells, and tumors were allowed to establish for 1 week. After tumor incorporation, the hindlimbs were treated with either the CD47 morpholino in sterile phosphate buffered saline (PBS) or an equal volume of PBS or the mice were treated intraperitoneally with the CD47 morpholino. Forty-eight hours later, all mice were subjected to right hind limb irradiation (10 Gy). The mice were observed and tumor size determined two to three times a week by the same individual until lesion size necessitated animal euthanasia.

Irradiation of cells. HUVEC and B16 mouse melanoma cells were plated in standard growth medium in 96- or 6-well culture plates (Nunc) and allowed to adhere. Irradiation was done on a Precision X-Ray X-Rad 320 (East Haven, Conn.) operating at 300 kV/10 mA with a 2 mm aluminum filter. The dose rate at 50 cm from the x-ray source was 242 cGy/minute, as determined by multiple thermo luminescent dosimeter readings.

Tissue Apoptosis: The ApopTag in situ detection kit (Chemicon, Millipore, Mass.) was used as described in Example 1. Additionally, animals were injected with $1\times10^6$ B16 melanoma cells and treated with either CD47 morpholino or sterile PBS as previously described. Mice were sacrificed 24 hours post irradiation (10 Gy), and hind limbs were embedded in paraffin blocks. Tissue sections incorporating the entire hind limb were examined for apoptosis employing 3'-hydroxy DNA strand breaks enzymatically labeled with digoxygenin nucleotide via TdT. Positive and negative control slides provided with the kit are used in each assay to ensure consistency.

Figure 19A:
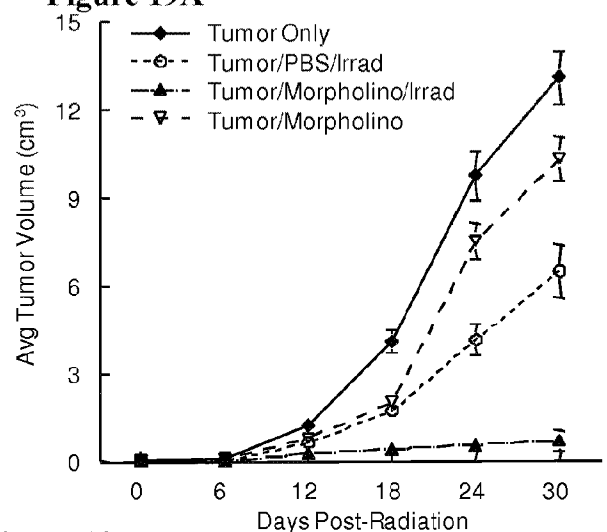
FIG. 19. CD47 suppression enhances re-growth delay in irradiated syngeneic B16 melanoma and squamous cell carcinoma tumors but increases radioresistance of B16 cells in vitro. C57BL/6 mice were injected with $1\times10^6$ B16 mouse melanoma cells into their right hindlimbs. Five days later, the mice were randomized into 4 groups (12 mice in each group) where they either received injections of CD47 morpholino (10 μM) in sterile PBS, PBS, or no injection. The two groups receiving injections were then subjected to radiation (10 Gy) to the effected hindlimb 48 hours later. The other two groups served as controls and consisted of tumor alone or tumor subjected to only the morpholino. Tumors were followed post-radiation for 30 days, measuring their volume every 6 days (FIG. 19A). Results are presented as the mean±SD of 12 mice in each treatment group and are representative of 3 independent studies. These same experimental treatment conditions were tested using another syngeneic tumor cell line (SCC VII) in C3H mice and followed for 15 days where similar results were found after injecting $1.5\times10^5$ cells (FIG. 19B). Results are presented as the mean±SD of 10 mice (C3II) in each treatment group and are representative of 3 independent studies. B16 mouse melanoma cells were plated on 96-well plates in standard growth medium. Cells were treated with peptide 7N3 or CD47 morpholino and received a radiation dose of 10 Gy (FIG. 19C; *p<0.05, #p<0.01). Cell (mitochondrial) viability was measured 48 hours post radiation using the MTT assay.

Radiation and CD47 Suppression Increases Tumor Ablation in a Syngeneic Murine Melanoma A major concern with any radioprotection strategy is that it will likewise enhance radio-resistance in tumors. As discussed above, syngeneic tumors implanted in TSP1 null mice demonstrated no loss in radiosensitivity in these tumors, but this does not address whether suppressing CD47 in the tumor would be radioprotective. Therefore, we implanted syngeneic B16F10 melanoma tumors into the thighs of C57BL/6 mice, treated them with the CD47 targeting morpholino or vehicle, and followed tumor growth rates after therapeutic irradiation (10 Gy). As expected, vehicle control and tumor only groups demonstrated rapid tumor growth, with animals succumbing within 3-4 weeks (FIG. 19A). Treatment with the morpholino in the absence of irradiation only slightly delayed tumor growth. In contrast, treatment of tumor-bearing limbs with the CD47 morpholino followed by irradiation dramatically increased tumor ablation thereby delaying tumor re-growth (FIG. 19A). Concurrent with an enhanced tumor response to radiation, the normal tissue areas of these limbs demonstrated minimal alopecia and no other morphologic or histologic evidence of tissue injury.

Figure 19B:
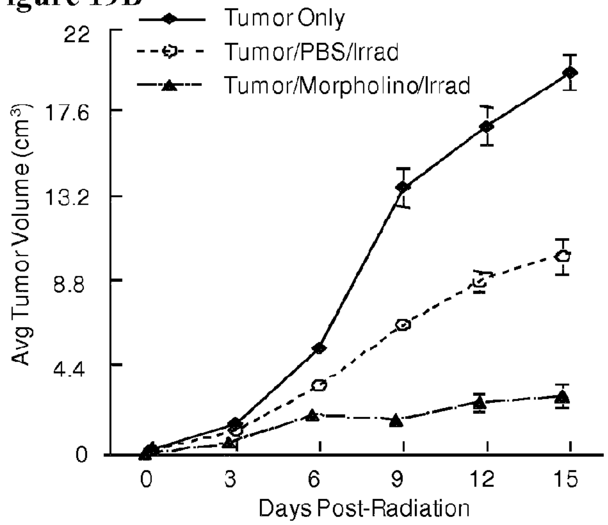

To determine whether this enhanced tumor response to IR was unique to the B16 melanoma or the C57BL/6 background, we conducted another study in C3H mice implanted into the hindlimb with a mouse squamous cell carcinoma (SCC VII). The same treatment and radiation schedules were used, and similar dramatic tumor growth delays relative to irradiation alone were seen in those mice treated with the CD47 morpholino (FIG. 19B).

Figure 19C:
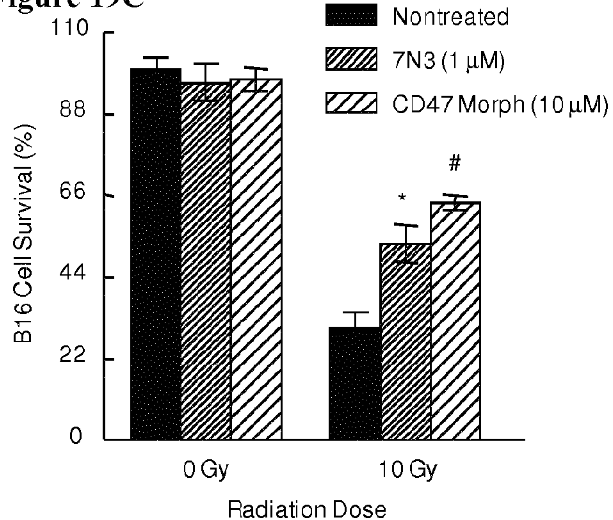

Analysis of isolated B16F10 melanoma cells exposed to irradiation (10 Gy) revealed a mild radioprotective effect for cell viability in vitro after treatment with either peptide 7N3 or CD47 morpholino when compared to untreated cells (FIG. 19C, *$p<0.05$. #$p<0.01$). These data demonstrate some cell autonomous effect of CD47 suppression on radio-resistance of this tumor cell line, but this cannot explain the dramatically increased tumor ablation as evidenced by the tumor growth delay effect seen in vivo. Therefore, other mechanisms were investigated by which CD47 suppression could increase the sensitivity of B16 tumors to radiation in vivo.

Systemic Suppression of CD47 Enhances Tumor Growth Delay Following Irradiation.

Figure 20:
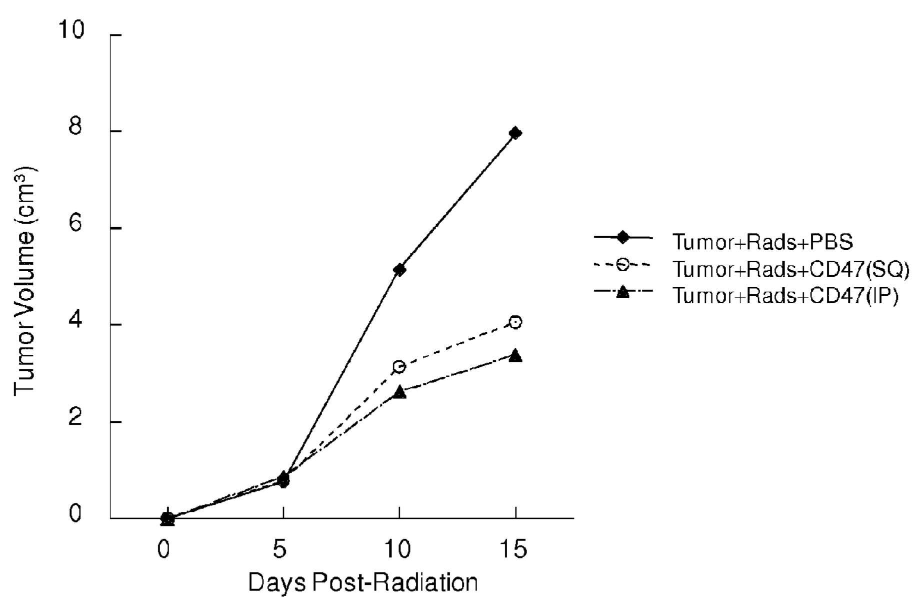
FIG. 20. Systemic delivery of CD47 morpholino is as effective as local delivery for enhancing tumor growth delay post-irradiation. Groups of 10 C3H mice were injected with SCC VII squamous cell carcinoma in the hindlimb as in FIG. 20. Mice were treated by local injection of PBS (closed circles) or CD47 morpholino (open circles) as above or by intraperitoneal injection of the morpholino (triangles) 48 prior to irradiation of the hindlimb at Gy. Tumor growth was assessed as above. Results are presented as the mean±SD of 10 mice (C3H) in each treatment group FIG. 21. Increased fibrotic response, viable immune reaction, and macrophage infiltration is seen in tumors with suppressed CD47 expression. C57BL/6 mice were injected with $1\times10^6$ B16 mouse melanoma cells into their hind limbs. Treatment consisted of two groups where the hind limbs were treated with either 150 μl of PBS or 150 μl of CD47 morpholino (10 μM) 48 hours prior to radiation (10 Gy). The control group consisted of just tumor without radiation. 24 hours post-radiation the mice were sacrificed, and their hindlimbs were prepared in paraffin embedded tissue sections for analysis. The top panels represent hind limbs and tumors in each group stained by standard H&E protocol (FIG. 21A). The middle panels demonstrate those cells undergoing apoptosis as detected by the TIJNEL method. Positive (apoptotic) cells are indicated by brown nuclear staining (FIG. 21B). Specific staining for macrophage surface marker CD68 was performed using a murine-specific antibody as seen in the bottom panels (FIG. 21C). Dark staining within the tumor indicates macrophage infiltration. Images were acquired using either a 4× or 10× objective.

For many tumors, local administration of radioprotectants is not feasible. Therefore, we determined whether systemic administration of the C47 morpholino was as effective as local administration. C3H mice were implanted with SCC VII cells, and after the tumors were established the mice were treated either locally or intraperitoneally with CD47 morpholino 48 hours prior to therapeutic irradiation. IP administration resulted in an equivalent delay in tumor growth (FIG. 20), indicating that the morpholino has adequate biodistribution for systemic use.

Increased Fibrosis, Inflammatory Response, and Macrophage Infiltration in Tumors where CD47 is Suppressed Tumor cells are often infiltrated with inflammatory cells such as lymphocytes, neutrophils, macrophages, and mast cells. Depending on their differentiation state, tumor-infiltrating macrophages can either limit or support tumor growth (Mantovani et al., *Eur J Immunol* 37:14-16, 2007; Pollard, J. W., *Nat Rev Cancer* 4:71-78, 2004; Nakakubo et al., *Br J Cancer* 89:1736-1742, 2003). Killing of tumor cells by M1 differentiated macrophages involves phagocytosis, which is inhibited when the target cells express CD47 (Matozaki et al., *Trends Cell Biol* 19:72-80, 2009; Okazawa et al., *J Immunol* 174:2004-2011, 2005), suggesting that suppression of CD47 on either the tumor or infiltrating cells could affect tumor regrowth. H&E staining of tumors from irradiated hind limbs treated with the CD47 morpholino revealed greater fibrosis and necrotic response within the tumor parenchyma post radiation compared to irradiated tumors without treatment (FIG. 21A). As expected, tumors in irradiated untreated hind limbs had increased numbers of inflammatory cells undergoing apoptosis (FIG. 21B). In contrast, tumors treated with the CD47 morpholino prior to irradiation showed minimal numbers of apoptotic cells associated with the tumor. Concurrently, tissue staining for the macrophage marker CD68 showed positive staining in the periphery of only those tumors subjected to CD47 suppression (FIG. 21C). Therefore, the increased regrowth delay in irradiated tumor-bearing limbs treated with the CD47 morpholino is associated with increased macrophage recruitment and/or survival, which may result in enhanced innate immune clearance of these irradiated tumors.

Example 5

Radioprotection by TSP1/CD47 Targeting is Largely NO-Independent

This example describes the characterization of the mechanism by which TSP1/CD47 targeting confers radioprotection.

Administration of the NO donor DETA/NO has been associated with increased survival in irradiated hamster fibroblasts (Wink et al., *Proc Natl Acad Sci USA* 90:9813-9817, 1993). TSP1, via CD47, is known to limit physiologic NO signaling in vascular cells and tissues of several mammalian species including mice and pigs (Isenberg et al., *Proc Natl Acad Sci USA* 102:13141-13146, 2005; Isenberg et al., *Ann Surg* 247:860-868, 2008; Isenberg et al., *Blood* 109:1945-1952, 2007), suggesting that the radioprotection obtained by suppressing CD47 expression results from enhanced NO signaling. However, treatment using a slow releasing exogenous NO donor (FIG. 22A) or a cell permeable cGMP analog (FIG. 22B) did not confer a significant survival advantage to irradiated HUVEC. Conversely, non-selective inhibition of endogenous NO production by NO synthases using L-NAME did not significantly increase cell death post-irradiation (FIG. 22C) and did not prevent treatment with the CD47 morpholino from enhancing cell survival (FIG. 22C). Therefore, the radioprotection afforded by TSP1/CD47 targeting occurs in a largely NO-independent manner.

It will be apparent that the precise details of the methods and compositions described herein may be varied or modified without departing from the spirit of the described invention. We claim all such modifications and variations that fall within the scope and spirit of the claims below, including all equivalents thereof.

The invention claimed is:

1. A method of protecting animal tissue from damage caused by ionizing radiation exposure, comprising contacting the tissue with a therapeutically effective amount of an agent that inhibits interaction between thrombospondin-1 (TSP1) and CD47, thereby protecting the tissue from radiation damage, wherein the agent is administered at a time within four days prior to the radiation exposure to within one day following the radiation exposure.

2. The method of claim 1, which is employed as a method of protecting a subject exposed to a radioactive substance or ionizing radiation, comprising contacting tissue of the subject with the therapeutically effective amount of the agent that inhibits the interaction of TSP1 and CD47.

3. The method of claim 1, wherein the radiation comprises an acute or chronic dose of ionizing radiation.

4. The method of claim 3, wherein the ionizing radiation results from nuclear fission or fusion.

5. The method of claim 3, wherein the ionizing radiation comprises X-rays.

6. The method of claim 3, wherein the ionizing radiation comprises radionuclides.

7. The method of claim 1, which is employed as a method of enhancing the therapeutic window for radiotherapy in a subject, comprising contacting tissue of the subject with the therapeutically effective amount of the agent that inhibits interaction between TSP1 and CD47 prior to the radiotherapy.

8. The method of claim 1, wherein the radiation exposure comprises diagnostic X-rays, radiation therapy, a CAT-scan, a mammogram, a radionuclide scan, or an interventional radiological procedure under CT or fluoroscopy guidance.

9. The method of claim 1, wherein the radiation exposure comprises tissue-incorporated radionuclides from inhalation, ingestion of contaminated food or water, non-medical or unintentional exposure to ionizing radiation from a nuclear weapon, non-medical or unintentional exposure to a radioactive spill, cosmic radiation, and/or space flight-associated radiation exposure.

10. The method of claim 1, wherein inhibiting interaction between TSP1 and CD47 comprises one or more of the following:

inhibiting expression of CD47;

inhibiting expression of TSP1; or blockading the interaction between endogenous TSP1 and CD47.

11. The method of claim 1, wherein the agent that inhibits the interaction between TSP1 and CD47 comprises:

an isolated or recombinant CD47 molecule or soluble fragment thereof;

an agent that decreases the expression of CD47;

an agent that decreases the expression of TSP1;

an anti-CD47 antibody;

an antibody that specifically binds TSP1;

TSP1 peptide 7N3 (SEQ ID NO:2);

TSP1 peptide C6d (SEQ ID NO:1); or a mixture or combination of two or more thereof.

12. The method of claim 1, wherein the agent that inhibits the interaction of TSP1 and CD47 is selected from the group consisting of peptide 7N3 (SEQ ID NO: 2) and peptide C6d (SEQ ID NO: 1).

13. The method of claim 11, wherein the agent that decreases the expression of CD47 or TSP1 is:

an oligonucleotide comprising at least 15 bases that hybridizes to the mRNA of CD47;

an oligonucleotide comprising at least 15 bases that hybridizes to the mRNA of TSP1;

an oligonucleotide comprising about 15 bases that hybridizes to the mRNA of CD47; or an oligonucleotide comprising about 15 bases that hybridizes to the mRNA of TSP1.

14. The method of claim 1, wherein the agent is:

an oligonucleotide comprising at least 15 bases and wherein the oligonucleotide hybridizes to the mRNA of CD47 or an oligonucleotide comprising about 15 bases and wherein the oligonucleotide hybridizes to the mRNA of CD47.

15. The method of claim 14, wherein the oligonucleotide is a morpholino.

16. The method of claim 15, wherein the morpholino comprises the sequence shown in SEQ ID NO: 4 (CGTCACAGGCAGGACCCACTGCCCA).

17. The method of claim 1, wherein the agent is an anti-CD47 antibody or a fragment thereof, or an antibody that specifically binds to TSP1 or a fragment thereof.

18. The method of claim 17, wherein the antibody is a humanized antibody.

19. The method of claim 1, wherein the agent is monoclonal antibody A6.1, monoclonal antibody C6.7, monoclonal antibody MIAP301, monoclonal antibody OX101, monoclonal antibody B6H12, an antibody that competes with A6.1, C6.7, MIAP301, OX101, or B6H12 for binding, a binding fragment of any one of these, or a humanized version of any one of these.

20. A method of increasing tumor ablation in a subject undergoing radiotherapy comprising contacting tissue of the subject with a therapeutically effective amount of an agent that inhibits interaction between TSP1 and CD47 prior to the radiotherapy, wherein the agent comprises:

an isolated or recombinant CD47 molecule or soluble fragment thereof;

an agent that decreases the expression of CD47;

an agent that decreases the expression of TSP1;

an anti-CD47 antibody;

an antibody that specifically binds TSP1;

TSP1 peptide 7N3 (SEQ ID NO:2);

TSP1 peptide C6d (SEQ ID NO:1); or a mixture or combination of two or more thereof, thereby increasing tumor ablation.

21. The method of claim 20, wherein the agent that decreases the expression of CD47 or TSP1 is:

an oligonucleotide comprising at least 15 bases that hybridizes to the mRNA of CD47;

an oligonucleotide comprising at least 15 bases that hybridizes to the mRNA of TSP1;

an oligonucleotide comprising about 15 bases that hybridizes to the mRNA of CD47; or an oligonucleotide comprising about 15 bases that hybridizes to the mRNA of TSP1.

* * * * *

SEQUENCE LISTING

```
<160> NUMBER OF SEQ ID NOS: 16

<210> SEQ ID NO 1
<211> LENGTH: 15
<212> TYPE: PRT
<213> ORGANISM: Artificial sequence
<220> FEATURE:
<223> OTHER INFORMATION: Synthetic Peptide

<400> SEQUENCE: 1

His Ile Gly Trp Lys Asp Phe Thr Ala Tyr Arg Trp Arg Leu Ser
1               5                   10                  15


<210> SEQ ID NO 2
<211> LENGTH: 11
<212> TYPE: PRT
```

<213> ORGANISM: Artificial sequence
<220> FEATURE:
<223> OTHER INFORMATION: Synthetic Peptide

<400> SEQUENCE: 2

Phe Ile Arg Val Val Met Tyr Glu Gly Lys Lys
1 5 10

<210> SEQ ID NO 3
<211> LENGTH: 11
<212> TYPE: PRT
<213> ORGANISM: Artificial sequence
<220> FEATURE:
<223> OTHER INFORMATION: Synthetic Peptide

<400> SEQUENCE: 3

Phe Ile Arg Gly Gly Met Tyr Glu Gly Lys Lys
1 5 10

<210> SEQ ID NO 4
<211> LENGTH: 25
<212> TYPE: DNA
<213> ORGANISM: Artificial sequence
<220> FEATURE:
<223> OTHER INFORMATION: Synthetic Oliogonucleotide

<400> SEQUENCE: 4
cgtcacaggc aggacccact gccca 25

<210> SEQ ID NO 5
<211> LENGTH: 25
<212> TYPE: DNA
<213> ORGANISM: Artificial sequence
<220> FEATURE:
<223> OTHER INFORMATION: Synthetic Oliogonucleotide

<400> SEQUENCE: 5
cgtgacagcc acgaccgact gcgca 25

<210> SEQ ID NO 6
<211> LENGTH: 21
<212> TYPE: DNA
<213> ORGANISM: Artificial sequence
<220> FEATURE:
<223> OTHER INFORMATION: Synthetic Oliogonucleotide

<400> SEQUENCE: 6
accgactcaa ccaggccaca g 21

<210> SEQ ID NO 7
<211> LENGTH: 21
<212> TYPE: DNA
<213> ORGANISM: Artificial sequence
<220> FEATURE:
<223> OTHER INFORMATION: Synthetic Oliogonucleotide

<400> SEQUENCE: 7
ggaggtccat tgtgcccatg g 21

<210> SEQ ID NO 8
<211> LENGTH: 21
<212> TYPE: DNA
<213> ORGANISM: Artificial sequence
<220> FEATURE:
<223> OTHER INFORMATION: Synthetic Oliogonucleotide

<400> SEQUENCE: 8

```
agggaccgcc tccacaagct g                                               21


<210> SEQ ID NO 9
<211> LENGTH: 21
<212> TYPE: DNA
<213> ORGANISM: Artificial sequence
<220> FEATURE:
<223> OTHER INFORMATION: Synthetic Oliogonucleotide

<400> SEQUENCE: 9

tctccgtgca ggaactggct g                                               21


<210> SEQ ID NO 10
<211> LENGTH: 15
<212> TYPE: DNA
<213> ORGANISM: Artificial sequence
<220> FEATURE:
<223> OTHER INFORMATION: Synthetic Oliogonucleotide

<400> SEQUENCE: 10

accctgcttg tgacg                                                      15


<210> SEQ ID NO 11
<211> LENGTH: 21
<212> TYPE: DNA
<213> ORGANISM: Artificial sequence
<220> FEATURE:
<223> OTHER INFORMATION: Synthetic Oliogonucleotide

<400> SEQUENCE: 11

gctttagggc agcacaggtc c                                               21


<210> SEQ ID NO 12
<211> LENGTH: 21
<212> TYPE: DNA
<213> ORGANISM: Artificial sequence
<220> FEATURE:
<223> OTHER INFORMATION: Synthetic Oliogonucleotide

<400> SEQUENCE: 12

ccgcaaacaa agatcaccca g                                               21


<210> SEQ ID NO 13
<211> LENGTH: 23
<212> TYPE: DNA
<213> ORGANISM: Artificial sequence
<220> FEATURE:
<223> OTHER INFORMATION: Synthetic Oliogonucleotide

<400> SEQUENCE: 13

gttggagtta tgttggaagg agg                                             23


<210> SEQ ID NO 14
<211> LENGTH: 21
<212> TYPE: DNA
<213> ORGANISM: Artificial sequence
<220> FEATURE:
<223> OTHER INFORMATION: Synthetic Oliogonucleotide

<400> SEQUENCE: 14

gcttggtgat agctggttac c                                               21


<210> SEQ ID NO 15
<211> LENGTH: 21
<212> TYPE: DNA
```

```
<213> ORGANISM: Artificial sequence
<220> FEATURE:
<223> OTHER INFORMATION: Synthetic Oliogonucleotide

<400> SEQUENCE: 15

tccgttccag aagagctgtc c                                    21


<210> SEQ ID NO 16
<211> LENGTH: 25
<212> TYPE: DNA
<213> ORGANISM: Artificial sequence
<220> FEATURE:
<223> OTHER INFORMATION: Synthetic Oliogonucleotide

<400> SEQUENCE: 16

atgggctgtg accggaactg tgggc                                25
```